United States Patent [19]

Rhodes et al.

[11] Patent Number: 5,717,065
[45] Date of Patent: Feb. 10, 1998

[54] SYNTHETIC POLYPEPTIDES AND ANTIBODIES RELATED TO EPSTEIN-BARR VIRUS NUCLEAR ANTIGEN

[75] Inventors: Gary Rhodes, Leucadia; Richard S. Smith, Del Mar, both of Calif.

[73] Assignee: The Scripps Research Institute, La Jolla, Calif.

[21] Appl. No.: 230,250

[22] Filed: Aug. 9, 1988

Related U.S. Application Data

[63] Continuation-in-part of Ser. No. 117,241, Nov. 4, 1987, Pat. No. 5,116,725, which is a continuation-in-part of Ser. No. 29,860, Mar. 24, 1987, abandoned, which is a continuation of Ser. No. 638,726, Aug. 8, 1984, Pat. No. 4,654,419.

[51] Int. Cl.⁶ .................. H11K 38/00; H11K 38/04; C12N 5/00; C12N 7/00
[52] U.S. Cl. .................. 530/326; 530/324; 530/325; 530/229
[58] Field of Search .................. 530/326, 329, 530/330, 324, 325

[56] References Cited

U.S. PATENT DOCUMENTS

| 4,628,045 | 12/1986 | Hahn | 530/330 |
|---|---|---|---|
| 4,654,419 | 3/1987 | Vaughn et al. | 530/326 |
| 4,686,282 | 8/1987 | Hahn | 530/329 |
| 5,116,725 | 5/1992 | Vaughn et al. | 435/5 |

OTHER PUBLICATIONS

Dillner et al. 1984. Antibodies against a synthetic peptide identify the Epstein–Barr . . . PNAS. 81:4652–4656.
Rhodes et al. 1985. Human Immune Responses to Synthetic peptides from . . . J. Immunol. 134(1):211–216.
Jahn et al. 1984. Predominant Immediate Early . . . J. Virol. 49(2):363–70.
Staprans et al. 1986. 2.2.-Kilobase Class of Early . . . J. Virol. 57(2):591–602.
Luka et al. 1984. Identification and Characterization . . . J. Virol. 52(3):833–38.

*Primary Examiner*—James C. Housel
*Assistant Examiner*—N. M. Minnifield
*Attorney, Agent, or Firm*—Thomas Fitting

[57] ABSTRACT

Antigens, immunogens, inocula, antibodies, and particularly diagnostic methods and systems relating to Epstein-Barr virus nuclear antigen (EBNA) are disclosed. The diagnostic methods and systems utilize a synthetic, random copolymer polypeptide containing about 6 to about 40 amino acid residues having a sequence corresponding to the sequence of a CMV-encoded polypeptide antigen. The diagnostic methods and systems are particularly useful in identifying infections mononucleosis during its acute phase.

2 Claims, 15 Drawing Sheets

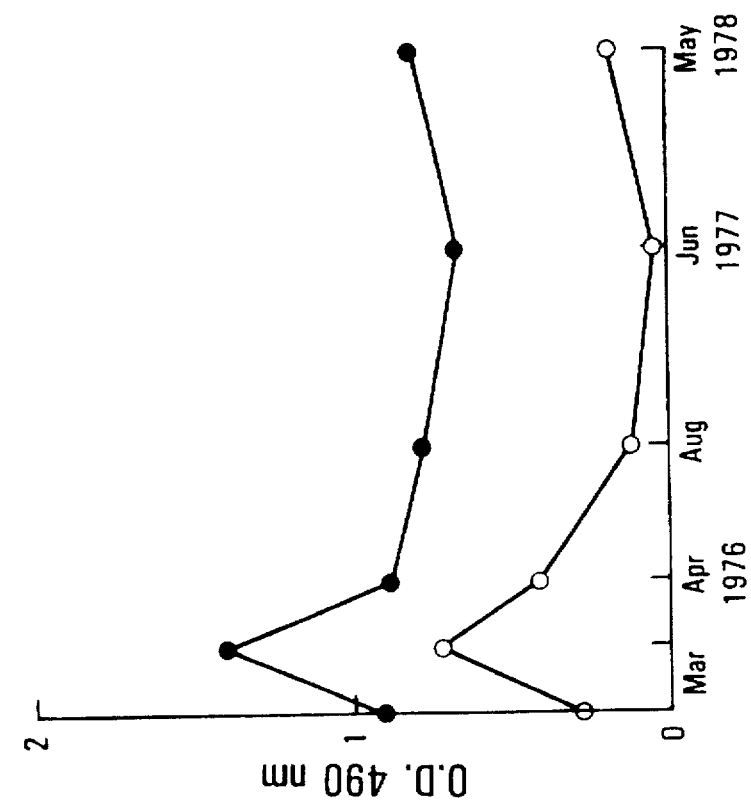
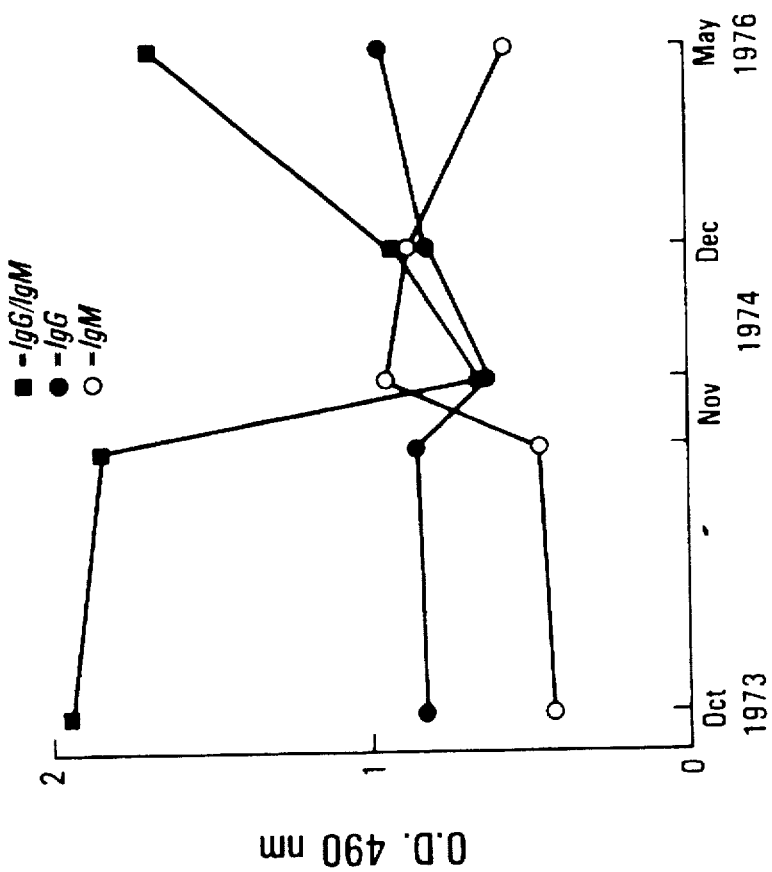
FIG. 10B
FIG. 10A

FIG. 13

SYNTHETIC POLYPEPTIDES AND ANTIBODIES RELATED TO EPSTEIN-BARR VIRUS NUCLEAR ANTIGEN

CROSS REFERENCE TO RELATED APPLICATIONS

This is a continuation-in-part of application Ser. No. 117,241 filed Nov. 4, 1987, now U.S. Pat. No. 5,116,725, that itself was a continuation-in-part of application Ser. No. 029,860 filed Mar. 24, 1987, now abandoned that itself was a continuation of application No. 638,726, filed Aug. 8, 1984 now U.S. Pat. No. 4,654,419, whose disclosures are incorporated herein by reference.

This invention was made with government support under Grant No. AM 21175 awarded by the National Institutes of Health.

TECHNICAL FIELD

The present invention relates to immunogens, antigens, inocula, antibodies, methods and systems useful in the treatment and diagnosis of diseases involving Epstein-Barr virus, its nuclear antigen, and cytomegalovirus.

BACKGROUND OF THE INVENTION

The Epstein-Barr virus (EBV) is a member of the herpes virus family and is the causative agent of infectious mononucleosis (IM) in humans. EBV has also been implicated in the pathogenesis of Burkitt's lymphoma, nasopharyngeal carcinoma, and B lymphocyte neoplasms arising in immunosuppressed patients. Circumstantial evidence has also indicated a possible role for this virus in human autoimmune disease such as rheumatoid arthritis and Sjogren's Syndrome.

EBV is an extremely common environmental agent infecting 80–100 percent of the individuals around the world. The initial or primary infection may be acute or sub-clinical. This is followed by a long period during which the EBV infection is latent in B lymphocytes present in the circulating blood, lymph nodes, and spleen.

Latency is the process by which a virus is present intracellularly in an unexpressed or partially expressed state. This latency can be reactivated. Although the host factors that control latency in vivo are poorly known, there is some evidence to suggest that failure of one or more immune mechanisms is an important factor.

Cytotoxic and suppressive T cell elements of the immune response to EBV are reported to be very important in suppressing acute infection by EBV in IM. They are also important in prohibiting the uncontrolled outgrowth of B lymphocytes latently infected with EBV.

Failure of T cell suppressor mechanisms is thought to be important in allowing the emergence of African Burkitt lymphoma, nasopharyngeal carcinoma, B cell lymphomas arising as a consequence of immunosuppressive therapy used to prevent rejection of organ transplantation, and lymphomas as arising during treatments of various auto immune disorders. Epstein and Achong eds., "The Epstein-Barr Virus.", Spring-Verleg, Berlin, Heidelberg (1970); and Crawford et al., Lancet, 1355 (1980). In addition, the failure of these T cell mechanisms and consequent overgrowth of EBV-infected lymphocytes is thought to play a role in rheumatoid arthritis. Slaughter et al., J. Exp. Med., 148:1429 (1978); Depper et al., J. Immunology, 127:1899 (1981) and Tosato et al., N. Engl. J. Med. 305:1238 (1981).

The serological and cell-mediated immune responses that follow primary infection by EBV are well documented and reflect the host's response to the viral antigens expressed during the course of infection. The profile of these responses as well as the detection of the antigens in tissues are becoming increasingly useful in the diagnosis of EBV-associated diseases.

Classically, the primary infection is detected by antibody to the viral capsid antigen (VCA) and the convalescent phase is noted by the rise of antibodies to the EBV-encoded nuclear antigens [EBNA] [Henle et al., Hum pathol., 5:551–565 (1974)]. EBNA-1, (also sometimes referred to herein as EBNA), the first nuclear antigen to be recognized, has been identified as a 65,000 to 85,000 kilodalton (kD) protein by the immunoblotting technique [Strand et al., J Virol., 38:990 (1981)]; Hennessey et al., Proc. Natl. Acad. Sci. USA, 80:5665–5669 (1983); and Billings et al., Proc. Natl. Acad. Sci. USA, 80:7104 (1983).

The size of the EBNA-I protein ranges from 65,000 to 85,000 in various B-cell lines, with about 77 kD being typical. The size of the molecule is correlated with the variation of the length of the IR-3 region of EBV-DNA [Hennessey et al., Proc. Natl. Acad. Sci. USA, 80:5665–5669 (1983)]. The IR-3 region encodes a repeating glycine-alanine sequence that has been characterized to be the major epitope of the EBNA-I protein [Billings et al., Proc. Natl. Acad. Sci. USA, 80:7104 (1983)].

Although the usually used assays probe VCA and then EBNA-1, EBNA-1 is the earliest EBV-associated antigen that can be detected after infection. EBNA has been detected in the nucleus of latently-infected growth-transformed B lymphocytes. EBNA has also been detected in the nuclei of African Burkitt tumor lymphoblasts and anaplastic nasopharyngeal carcinoma cells.

The concentration of EBNA in cell nuclei of EBV-infected B lymphocytes fluctuates during various phases of the cell's reproductive cycle. Thus, it is believed EBNA is cyclically being synthesized and degraded. As a result of such degradation, protein fragments (polypeptides) of EBNA traverse the cellular cytoplasm and are believed to exist or be expressed on the outer membrane. However, specific EBNA degradation polypeptides have not been identified to date.

It is believed that while in or on the outer cell membrane, EBNA degradation polypeptides constitute a significant stimulus to the host's T lymphocytes and initiate the immune response that results in the production of anti-EBNA antibodies. It is also believed that the specific T cell response to B cells expressing EBNA degradation polypeptides on their surfaces may contribute to the generation of cytotoxic and suppressive T cells important in restricting growth of EBNA-containing (EBV-infected) B lymphocytes.

Thus, assays for the presence of both EBNA and anti-EBNA antibodies are of importance in several common clinical situations. In addition, a vaccine against EBV-infected B lymphocytes would also be of clinical importance.

Anti-EBNA antibodies are typically assayed using the tedious anti-complement immunofluorescence technique (ACIF). Reedman et al., Int. J. Cancer, 11:499–520 (1973). This assay involves fixing EBV-transformed human B cells to a microscope slide. Various dilutions of a patient's serum are then added to the fixed cells. Because anticomplementary sera may yield false-negative reactions or prozones when they are mixed with the complement (a two-stage procedure), it is essential to charge the test cell smears consecutively with serum, complement, and the anticomplement-fluorescence conjugate (a three stage procedure).

There are several problems with this assay. These include the fact that the assay is relatively insensitive and requires amplification mediated through complement. In addition, this assay is not entirely specific and may not be interpreted in patients whose serum contains antibodies to mammalian cell nuclei. Still further, quantitative results obtained using an anti-complement immunofluorescence assay are difficult to reproduce. As a consequence of these and other reasons, assays for anti-EBNA antibodies have generally been confined to a few, specialized laboratories.

The above difficulties in assaying for anti-EBNA antibodies stem from the lack of relatively pure EBNA. Purification of EBNA from mammalian cell tissue cultures is complex because of the antigen's low concentration and polymorphology. Although it is easier and less costly to use whole cells expressing EBNA, as in the current technique, the problems of specificity and reproducibility are directly the result of using whole cells.

Synthetic peptides containing portions of the glycine-alanine EBNA-1 region have been shown to be reactive with sera from patients with EBV-IM [Rhodes et al., in *Herpesvirus*, R. Rapp ed., Alan R. Liss, New York; p. 487–496 (1984); Rhodes et al., *J. Immunology*, 134:211–216 (1985); Smith et al. *J. Infec. Dis.*, 154:885–889 (1986) and Geltosky et al. *J. Clin. Lab Analysis*, 1:153–162 (1987)]. As shown in U.S. Pat. No. 4,654,419 and subsequently elsewhere, the peptide denominated P62 can be used in an ELISA assay to distinguish serologically, the acute phase of EBV-IM from the convalescent phase and recovery phase of IM [Smith et al. *J. Infec. Dis.*, 154:885–889 (1986) and Geltosky et al. *J. Clin. Lab Analysis*, 1:153–162 (1987)].

The acute phase of the disease is detectable by the appearance of IgM antibodies to this peptide. During the convalescent phase, the IgM antibody titre falls and IgG antibody can be detected [Smith et al. *J. Infec. Dis.*, 154:885–889 (1986)]. Patients with a long past infection have IgG antibodies to the peptide as the predominant immunoglobulin class.

Antibody production against the EBNA-1 protein is highly unusual. IgM antibodies recognizing the glycine-alanine peptide P62 are detected within one day of the onset of the disease [Smith et al., *J. Infec. Dis.*, 154:885–889 (1986)]. When analyzed by immunoblotting, it was found that these IgM antibodies recognize the EBNA-1 protein as well as more than a dozen normal cellular proteins [Rhodes et al., *J. Exp. Med.*, 165:1026–1040 (1987)]. Antibody binding to EBNA-1 and to the autoantigens can be inhibited by the peptide P62. Thus, acute EBV infection induces the synthesis of autoantibodies that seem to share an epitope related to the glycine-alanine repeating region of EBNA-1.

In contrast, IgG antibodies to EBNA-1 do not appear until several months after onset of the disease. IgG anti-peptide P62 antibodies measured by the ELISA assay [Smith et al. *J. Infec. Dis.*, 154:885–889 (1986) and Geltosky et al. *J. Clin. Lab Analysis*, 1:153–162 (1987)], anti-EBNA-1 antibodies measured by the standard anti-complement immunofluorescence [Reedman et al., *Int. J. Cancer*, 11:499–520 (1973)] and IgG antibodies to the EBNA-1 protein measured by immunoblotting all appear concurrently. These IgG antibodies can also be inhibited by the peptide P62 but are specific for the EBNA-1 protein and no longer react with the cellular autoantigens [Rumpold et al., *J. Immunol.*, 138:593–599 (1987); Rhodes et al., *J. Exp. Med.*, 165:1026–1040 (1987); and Dillnet et al., *Proc. Natl. Acad. Sci. USA*, 82:4652–4656 (1984)].

Cytomegalovirus (CMV) is another member of the herpes virus family. CMV infections in immunocompetent persons are usually without significant complications and typically resemble EBV-caused mononucleosis.

Diagnosis of a CMV infection in a patient with IM-like symptoms can be established by virus isolation from vascular lesions. Antibodies produced in response to a CMV infection can be detected by neutralization (NT), complement fixation (CF), immunofluorescence and platelet-agglutination (PA) procedures. [See, Weller, *N. Engl. J. Med.*, 285:203 (1971).]

CMV infections are also latent, and the disease occurs in patients on immunosuppressive therapy and in those subject to opportunistic infections. CMV infection has become the most common infection in patients receiving allogenic bone marrow transplantation and is an important determinant of the success or failure of the transplant procedure [Neiman et al., *J. Infect. Dis.*, 136:754 (1977)].

Among adults undergoing immunosuppressive therapy after renal homotransplantation, over 90 percent develop active cytomegalovirus antibodies. Approximately one-half of the seronegative patients subsequently become infected on immunosuppressive therapy. Seronegative recipients receiving a kidney from a seropositive donor almost always develop a postoperative infection and are likely to develop symptoms of the infection.

For immunocompetent persons, i.e., persons not taking immunosuppressive drugs and those free from immunocompromising diseases such as ARC and AIDS, CMV mononucleosis (CMV-IM) infections are typically found in infants (from birth through about 2 years old) and in adults; i.e., persons older than about 30 to 35 years. Infectious mononucleosis caused by EBV (EBV-IM) is generally found in persons in their teens through about 25 years of age, and particularly in persons about 15 to about 25.

Patients with both diseases exhibit atypical lymphocytosis, pharyngeal symptoms, abnormal liver function tests, splenomegaly and fever. Sera from CMV-IM patients are heterophil-negative, whereas sera from most EBV-IM patients are heterophil-positive.

Genetic engineering and synthetic polypeptide technologies have recently provided solutions to the problem of manufacturing large quantities of protein and polypeptide antigens. However, both techniques are effective only if the amino acid residue sequence of the native protein is known.

The amino acid residue sequence of a natural protein can be determined from the protein itself, but this is often difficult. The gene nucleotide sequence that codes for the protein may also reveal the protein's amino acid residue sequence. However, all DNA sequences have three possible reading frames, each of which yields a different protein. Therefore, the correct reading frame must be known to deduce the correct amino acid residue sequence of a protein from its gene.

The correct reading frame of a DNA sequence coding for a protein, and therefore the protein's amino acid residue sequence, may be determined through the use of antibodies. This strategy involves manufacturing an array of protein fragments or polypeptides whose amino acid residue sequences correspond to the sequences obtained from the three possible gene products. The protein fragments or polypeptides that induce antibodies that immunoreact with the gene's natural protein product thereby identify the gene's correct reading frame. Conversely, if antibodies to the natural protein recognize the manufactured protein fragments or polypeptides, the relationship between gene and protein is also established.

Heller, et al., *J. Virol.*, 44:311–320 (1982), reported the DNA sequence for a portion of the EBV genome that was found to contain an internal region, designated IR3, consisting of direct repeats of a hexanucleotide and two nonanucleotide sequences. They cited evidence suggesting that the sequence surrounding and including IR3 contains the gene coding for EBNA. However, since it was not known which of the three possible DNA sequence reading frames was translated, Heller, et al., supra, were not able definitely to deduce the amino acid sequence for the possible EBNA protein.

In September 1983, Hennessy and Kieff, *Proc. Natl. Acad. Sci., U.S.A.*, 80:5665–5669 (1983), reported establishing the natural reading frame for the EBV DNA sequence reported by Heller, et al., supra. Essentially, they isolated IR3 DNA, cleaved it into small random pieces and inserted the pieces into the lacZ gene of an *E. coli* expression vector such that all three EBNA gene reading frames were expressed, each in a different clone. The lacZ gene codes for beta-galactosidase, a bacterial enzyme. The IR3-lacZ gene fusion product is expressed in *E. coli* as a fusion protein with the IR3 protein sequence inserted between amino acids 7 and 9 (8 being deleted in the construction process) of the beta-galactosidase protein molecule.

Hennessy and Kieff, identified an IR3-lacZ gene fusion that was expressing IR3 DNA in its natural reading frame by screening for fusion proteins that were recognized by anti-EBNA positive human sera. A plasmid so identified was designated pKH182-44.

To confirm that the protein expressed by pKH182-44 contained EBNA-specific antigenic determinants, Hennessy and Kieff, supra, raised antisera in rabbits against cyanogen bromide-cleaved (CNBr) IR3-galactosidase fusion protein. The CNBr fragment used an immunogen containing 53 amino acids' homologous to EBNA and 89 amino acids homologous to beta-galactosidase. These antisera recognized natural EBNA in EBV-infected cells using indirect immunofluorescence.

The results of Hennessy and Kieff appear to be dependent on the repetitive nature of the EBNA IR3 domain. The fusion protein produced by pKH182-44 contains a relatively long segment homologous with the IR3 domain (e.g. 53 amino acids). It is, therefore, not surprising that the fusion protein and CNBr fragment thereof contained antigenic determinants. Furthermore, Hennessy and Kieff did not identify which of the sequences repeated in their fragment were acting as antigenic determinants.

Although Hennessy and Keiff were able to genetically manufacture a material recognized by anti-EBNA antibodies in human serum, it would be cumbersome to use in a clinical setting because of its design. The 53 amino acid residue segment of their fusion protein that is homologous to EBNA is physically and chemically part of the beta-galactosidase protein. Its immunological properties are, therefore, influenced by those portions of the beta-galactosidase molecule from which it cannot be separated. In fact, all of the human sera used in their study reacted with beta-galactosidase, and required treatment with beta-galactosidase to adsorb and remove this reactivity before testing for specificity against the genetically manufactured protein.

Another approach to the interrelated problems of determining a gene's correct reading frame and manufacturing large quantities of pathogen-related antigens (immunogens) for clinical and diagnostic purposes is the use of synthetic polypeptide chemistry. This method of manufacturing antigens (immunogens) has an advantage over the genetic engineering methods described above. Synthetic polypeptide antigens do not contain natural protein by-products or fragments thereof, and thereby their use eliminates the possibility of unwanted cross reactivity and the need to pretreat serum samples as in the Hennessy and Kieff study.

While the general concept of preparing synthetic antigens (immunogens) and using them to induce antibodies of predetermined specificity has been described, there remains a large area of this technology that continues to defy predictability. There are at least two reasons for this. First, a synthetic antigen (immunogen) does not necessarily induce antibodies that immunoreact with the intact protein in its native environment. Second, a host's natural antibodies to a naturally occurring immunogen such as a viral protein rarely immunoreact with a polypeptide that corresponds to a short linear portion of the immunogen's amino acid residue sequence. This latter phenomenon is believed to be the result of short linear polypeptides lacking required secondary and tertiary conformational structures.

Much of the work on the binding of peptide by antibody made to proteins is summarized in a review by Benjamini, E., et al., *Current Topics in Microbiology and Immunology* 58:85–134 (1972). The role of peptide structure in antibody binding has been emphasized by Goodman, J. W., *Immunochem.* 6:139–149 (1969).

Most of the studies concerned with how changes in the sequence of peptides effect antibody binding have been interpreted as indicating that the structure of the antibody combining site plays a predominant role. The effect of sequence and structural changes in these studies is intermixed and difficult to segregate. Some of these studies can equally well be explained by structural changes in antigen effecting the binding.

Antibody response at the molecular level involves binding of an antigen of defined sequence (primary structure) and in a defined conformation (secondary and tertiary structure). Immune response to protein antigens has traditionally been interpreted as being directed against primary, secondary or tertiary structure of the protein.

This classification scheme may have some validity for proteins that have a well defined overall structure at physiological temperatures and solutions. However, its validity is in doubt for peptide antigens that have a more dynamic structure.

Several groups have reported structural studies of polymers of repeating sequence of glycine and alanine or glycine and serine that were synthesized as models of silk fibroins [Anderson et al., *J. Mol. Biol.* 67:459–468 (1972)] and collagen [Anderson et al., *BBRC* 39:802–808 (1970); Doyle et al., *J. Mol. Biol.* 51:47–59 (1970]. The most systematic study has been that of Bracket al., *Biopolymers* 11:563–586 (1972) who reported synthesis of a series of block homopolymeric polypeptides in which the homopolymeric block repeating units had the formula $(Ala_x—Gly_y)$ wherein when x=1, y=1, 2 and 3; when x=2, y=1, 2 and 3; and when x=3, y=3.

The results reported from this latter study were that in the solid state the block homopolymers composed mostly of alanine were alpha-helical, and those containing mostly glycine were disordered. In solution, polyalanine was reported to be alpha-helical, but poly-$(Ala_2—Gly_1)$ was reported to be in beta-antiparallel form. The more glycine-rich polymers were said to have another fixed structure that was reported as neither alpha-helix nor the beta-structure.

The homopolymerized blocks of glycine and alanine reported by Bracket al. were prepared by the condensation polymerization of the di- through hexapeptide repeating units having a carboxyl-terminal glycyl residue in active ester form. Degrees of polymerization from 2 through 68 were reported for poly(Ala—Gly$_2$).

Even though the solvents used in those studies were not physiologically acceptable, e.g., water or phosphate buffered saline, the results illustrate two points: (1) structural changes can occur as the sequence of a polypeptide changes, and (2) structural changes also occur during the transition from solution to solid state.

SUMMARY OF THE INVENTION

The present invention contemplates a CMV-homologous polypeptide. The polypeptide contains about 6 to about 40, preferably about 15 to about 40, amino acid residues having a sequence corresponding to the sequence of the CMV-encoded polypeptide shown in FIG. 1, said sequence including ka sequence defined by the formula:

$$-Gly-R^1-Gly-R^2-Gly-$$

wherein $R^1$ and $R^2$ designate amino acid residues which when taken individually are the same or different and are Ala, Asn, Arg, Gly, Leu, Pro, Ser and Thr, provided that $R^1$ and $R^2$ are not both Gly, pharmaceutically acceptable salts thereof and antigenically related variants thereof.

In another embodiment, the present invention contemplates a method of assaying for anti-EBNA antibodies in a body sample. The method comprises admixing a patient's body sample with a CMV-homologous peptide of this invention. The immunoreaction admixture thus formed is maintained for a predetermined time period sufficient for any anti-EBNA antibodies present in the sample to immunoreact with the peptide to form an immunoreaction product. The presence of any product formed is then determined, and thereby the presence of anti-EBNA antibodies in the sample. In preferred embodiment, the method is immunoglobulin class specific.

The present invention also provides a diagnostic system for assaying for the presence of anti-EBNA antibodies in a body sample. The system includes, in separate packages, (a) a CMV-homologous polypeptide, and (b) an indicating means for signaling the presence of an immunoreaction between the polypeptide and human anti-EBNA antibodies. Preferably, the indicating means is an enzyme-labeled human Ig class-specific antibody.

The present invention also contemplates a multimer containing a plurality of joined polypeptide repeating units wherein at least one of the repeating units is a polypeptide as described above. The polypeptide repeating units may be joined in a head-to-tail manner by amide bonds. Alternatively, the synthetic polypeptide monomers may be joined by other than amide bonds to form a polymeric multimer such as through the use of intramolecular, interpolypeptide cysteine disulfide bonds.

A method for assaying for the presence of anti-EBNA antibodies utilizing a before-described polypeptide or multimer as antigen is contemplated herein. In accordance with this method, a liquid human body sample is provided and is admixed with the before-described polypeptide. The resulting immunoreaction admixture is maintained for a predetermined time sufficient for any anti-EBNA antibodies present in the sample to immunoreact with the polypeptide and form an immunoreactant. The presence of the immunoreaction is then determined. In particularly preferred practice, the presence of an immunoreaction is determined by admixing anti-human heavy chain antibodies such as anti-IgG, -IgM or -IgA antibodies with the immunoreactant, maintaining that second immunoreaction admixture for a predetermined time sufficient for the anti-human antibodies to immunoreact with anti-EBNA antibodies present in the immunoreactant to form a second immunoreactant, and then determining the presence of the second immunoreactant, and of the particular human anti-EBNA heavy chain antibody species present.

Most preferably, the assay is carried out using the polypeptide or multimer affixed to a solid matrix to form a solid support. The body sample such as blood, serum, plasma, saliva or sputum is admixed with the solid support to form a solid/liquid phase immunoreaction admixture. That admixture is maintained as above, to form a solid phase-bound immunoreactant that contains the anti-EBNA antibodies, and the solid and liquid phases are thereafter separated. The presence of the solid phase-bound immunoreactant is then determined.

Further contemplated is a diagnostic system for assaying for the presence of antibody molecules to EBNA in a human body component. Such a system comprises a polypeptide of the present invention and an indicator means for signaling the immunoreaction of the polypeptide with the anti-EBNA antibody molecules. In a more preferred embodiment, this system also contains a solid support comprised of a solid matrix to which the polypeptide is affixed. A means for identifying the isotype of the immunoreacted antibody molecules may also be included in the system.

BRIEF DESCRIPTION OF THE DRAWINGS

In the Figures forming a portion of the disclosure of this invention.

Recognition of EBNA by anti-P60 serum was inhibited by incubating anti-P60 serum diluted 1:50 with 40 micrograms/milliliter (ug/ml) of polypeptide P60 for one hour prior to immunoblotting (lane 3). Similarly, recognition of EBNA by anti-P62 serum was inhibited by incubating anti-P62 serum diluted 1:10 with 40 ug/ml of polypeptide P62 for one hour prior to immunoblotting.

The antigenic relatedness of P60 and P62 is demonstrated in lanes 6 and 7. Lane 6 shows anti-P62 serum diluted 1:10 immunoreacting with the EBNA band. In lane 7, the immunoreactivity of anti-P62 serum with the EBNA band was inhibited by incubation with polypeptide P60 at 40 ug/ml for one hour prior to immunoblotting.

Figure 3:
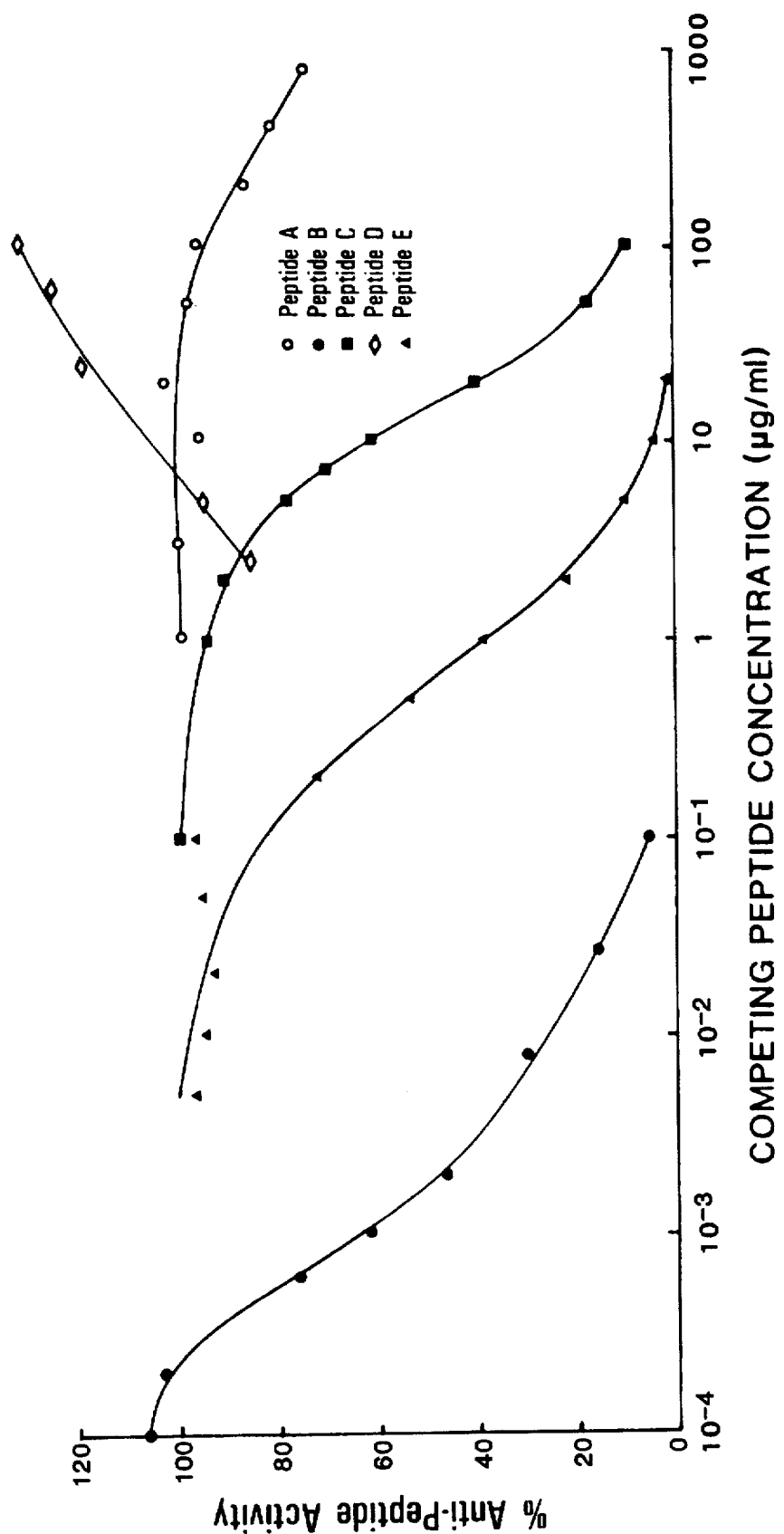

FIG. 3 is a graph illustrating the inhibition of anti-P62 serum activity in EBNA-positive serum of patient 1011 by a competing polypeptide in solution. An ELISA using polypeptide P62 as the solid phase target was performed using serum of patient 1011 pre-incubated for one hour with either of polypeptides P27, P62, P60, P89 or F16 before use in the ELISA. Polypeptides P27, P62, P60, P89 and P16 are also referred to herein as polypeptides A, B, C, D, and G, respectively. The percent anti-polypeptide activity is plotted as the ordinate versus the concentration of the competing polypeptide in micrograms per milliliter (ug/ml).

Figure 4:
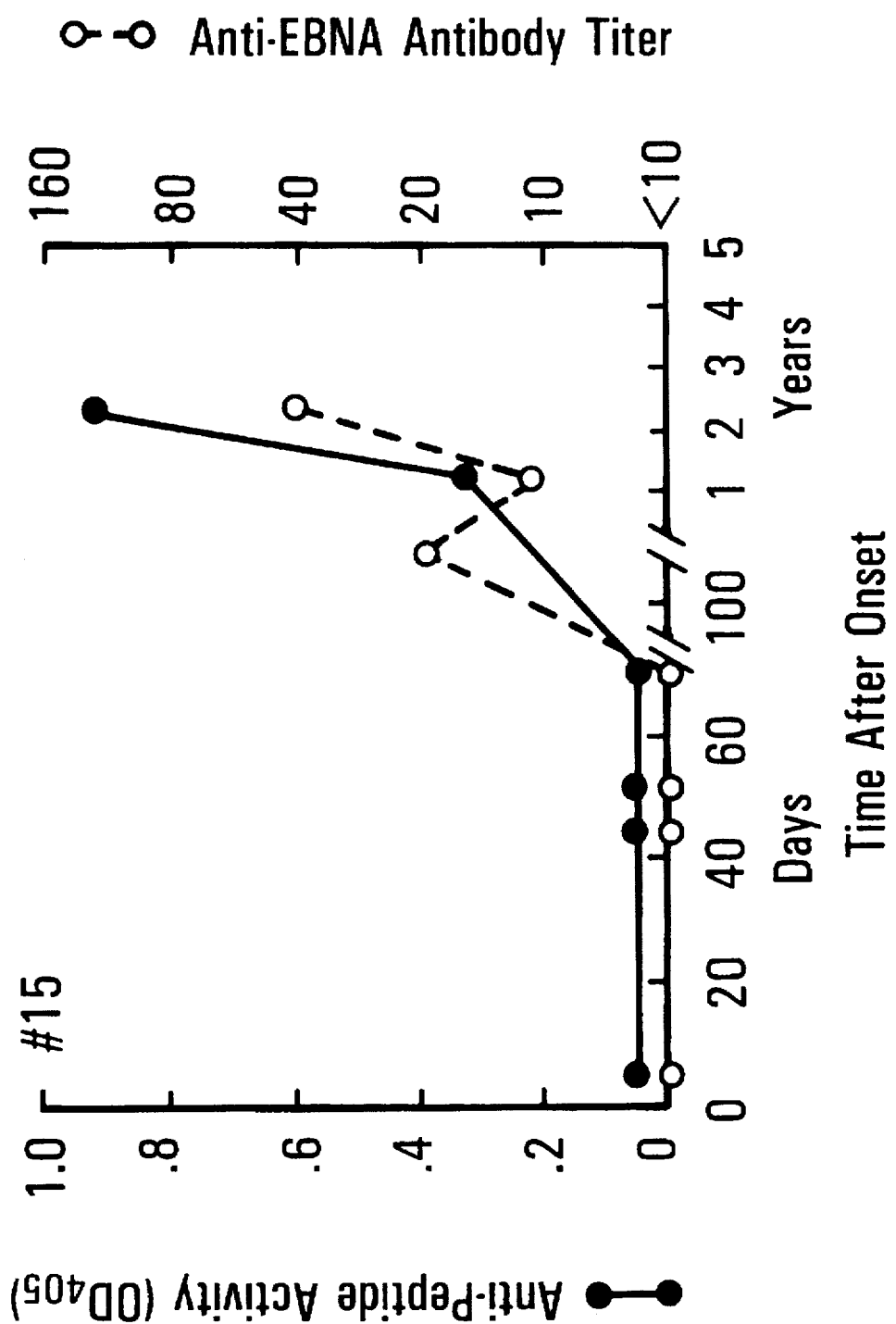

FIG. 4 is a graph that illustrates the parallel time course of appearance of antibodies to EBNA (dashed line, open circles) and polypeptide P62 (solid line, closed circles) in a case of documented EBV infectious mononucleosis (EBV-IM). Sequential sera were collected after clinical onset and were titered for anti-EBNA activity following the procedure reported in Catalano, et al., *J. Clin. Invest.*, 65:1238–1242 (1980) on the right-hand ordinate. The serum samples were also assayed in the ELISA of this invention using polypeptide P62 as the solid phase target as is shown on the left-hand ordinate wherein the optical density at 405 nanometers ($OD_{405}$) is plotted.

Figure 5A:
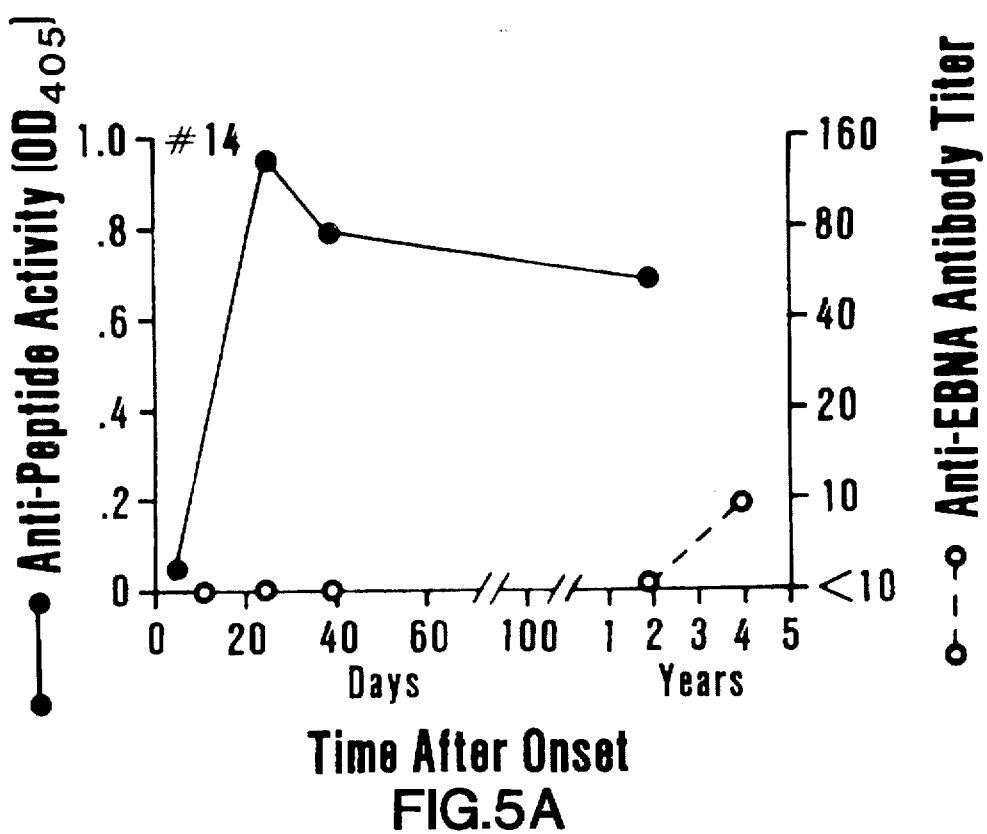
Figure 5B:
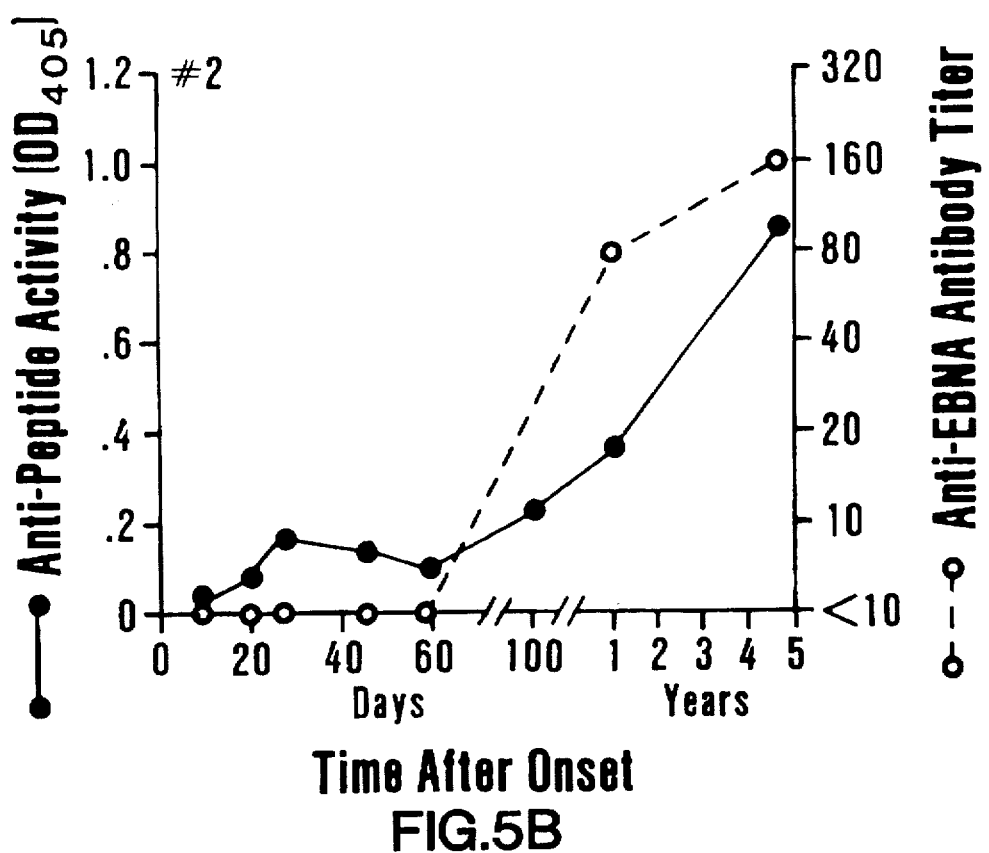

FIG. 5 is composed of two graphs that illustrate the early detection of antibodies to polypeptide P62 (solid line, closed circles) as compared to anti-EBNA (dashed line, open circles) using detection by the classical ACIF method described by Henle, G. et al., *J. Infect. Dis.*, 130:231 (1974). Sequential sera were collected from two patients (#14 top panel, #2 bottom panel) with clinically documented infectious mononucleosis. The sera were titered for anti-EBNA activity as reported in Catalano, et al., above. Anti-polypeptide activity was measured using the ELISA of this invention using polypeptide P62 as the solid phase target, with the activity being reported as in FIG. 4.

Figure 6:
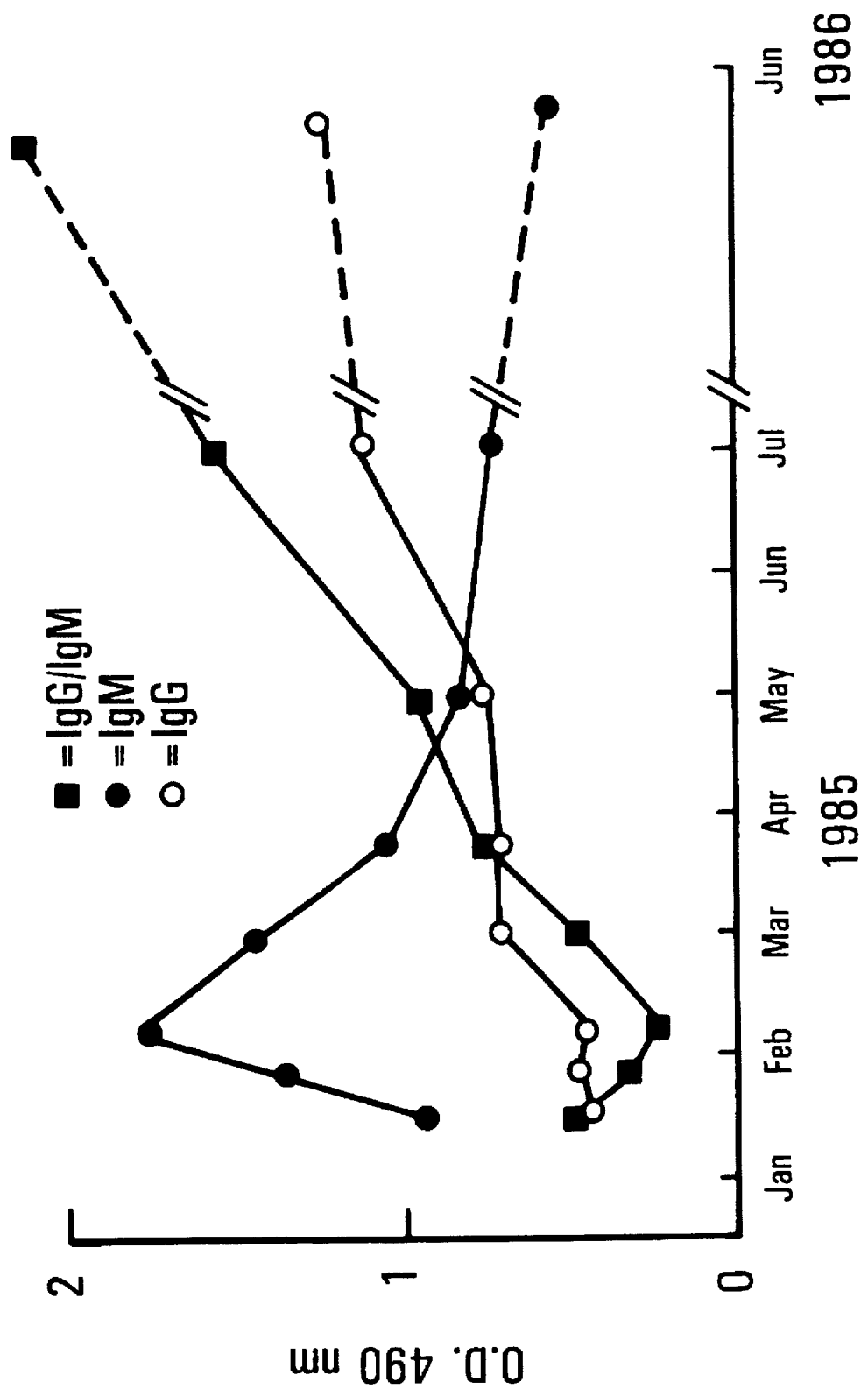

FIG. 6 is a graph showing an analysis of sequential sera from patient D.B. who had an acute EBV-IM infection, assayed by the EBNA P62 ELISA. The acute phase IgM response is shown by closed circles, the convalescent IgG response is indicated by open circles, and the ratio of IgG/IgM is denoted by open squares. The EBNA polypeptide P62 assay was performed as described in the Materials and Methods section.

Figure 7:
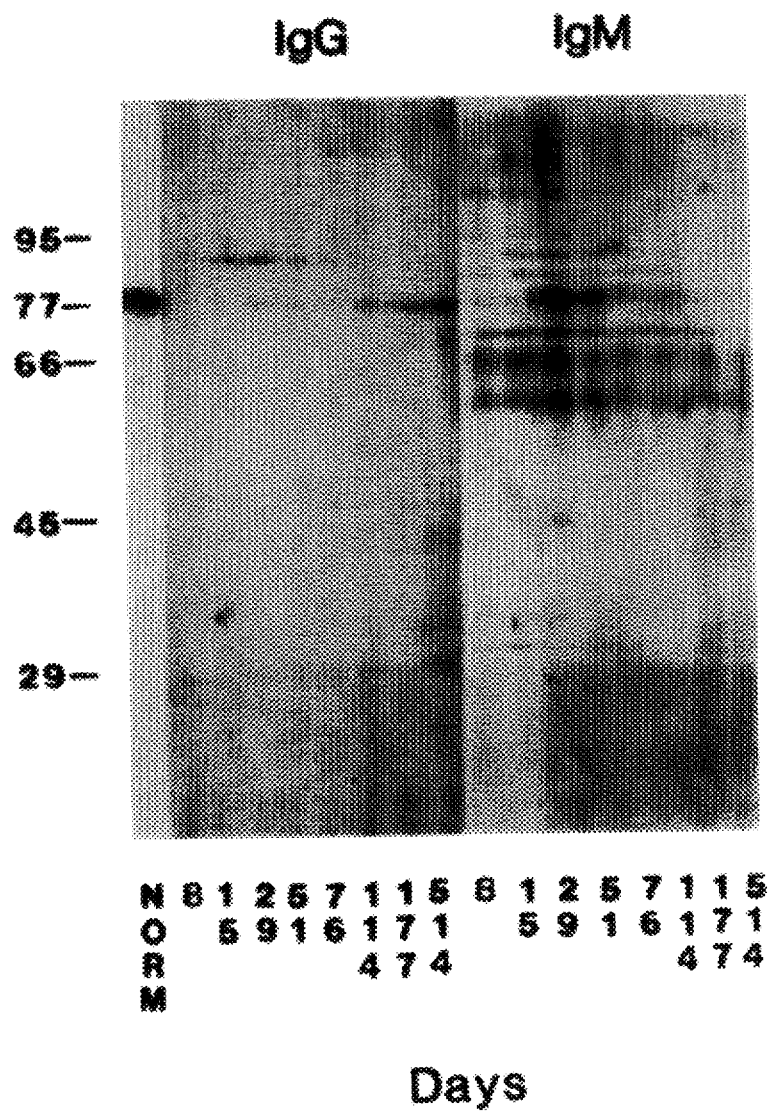

FIG. 7 is a photograph of immunoblots that illustrate an analysis of sequential sera from patient D.B. Lysates of EBV-immortalized Wi-L2 (also referred to as WI-L2) cells were used as the source of EBNA-1 proteins for the blots. On the left side of the blot, a normal (NORM), VCA positive sample was used as a control to indicate the 77 kD EBNA-1 protein. The blots show the delayed response (left side) of the IgG antibodies to the 77 kD EBNA proteins and the rapid rise of the IgM antibodies to these proteins in the acute phase of the illness (right side). Days after onset of disease are indicated by the numerals below each lane that are to be read vertically.

Figure 8:
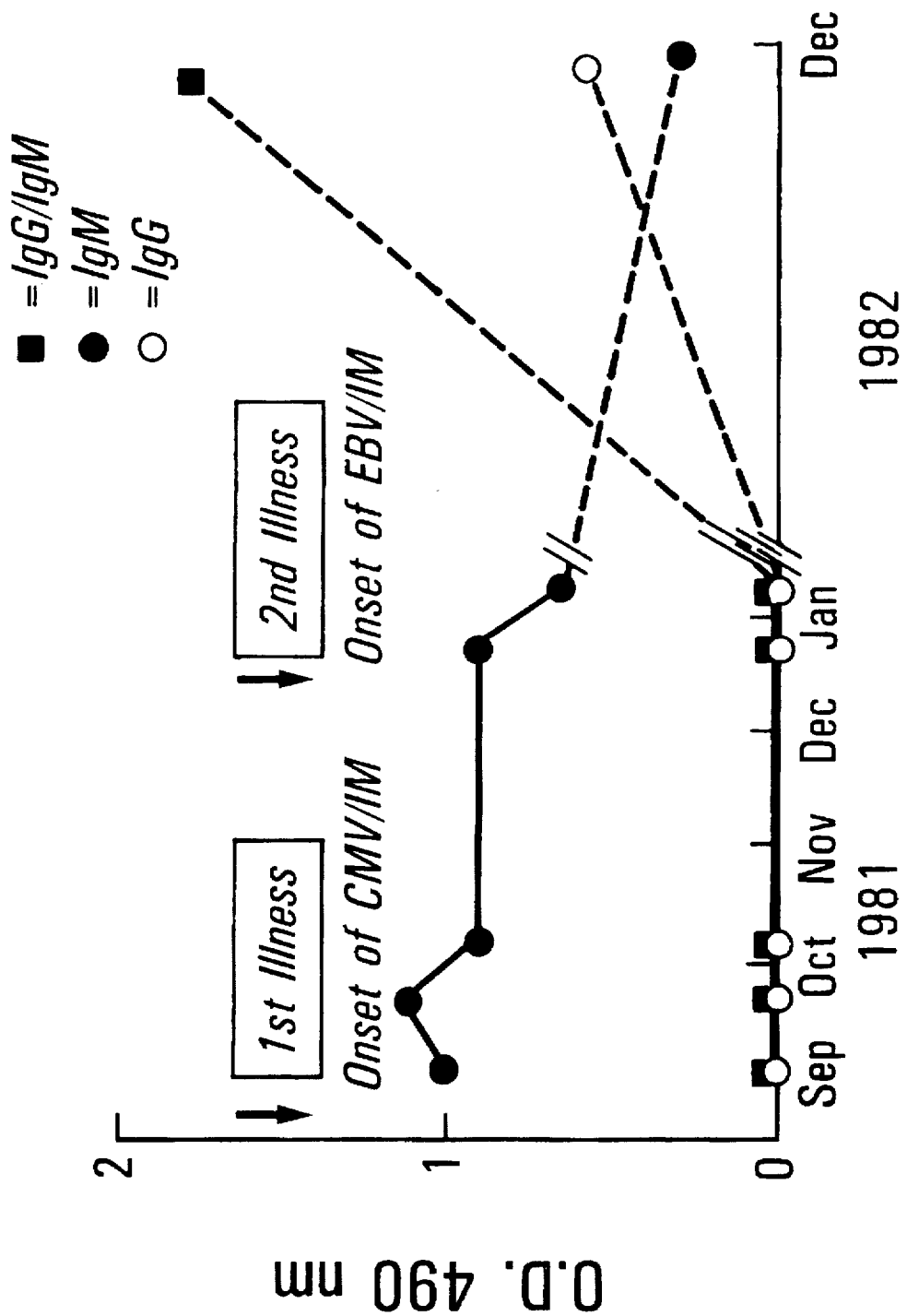

FIG. 8 is a graph that illustrates an analysis of sequential sera from patient D.S. with a first infection due to CMV-IM followed by a second infection due to EBV-IM. The acute phase IgM response is shown by closed circles, the convalescent IgG response is indicated by open circles, and the IgG/IgM ratio is shown as closed squares.

Figure 9:
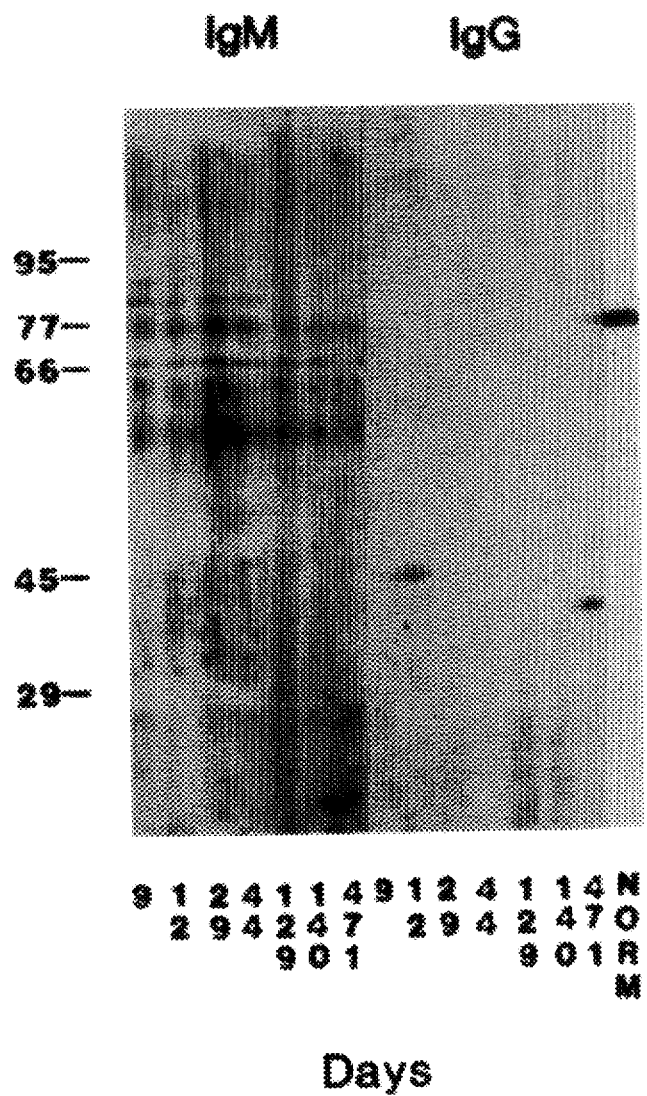

FIG. 9 is a photograph of an immunoblot study that illustrates an analysis of sequential sera from patient D.S. by the immunoblotting technique. The left side of the blot illustrates the acute phase IgM response to EBNA-1 proteins by the patient's sera. The right side of the blot illustrates the IgG response from the patient's sera. The numerals below each lane and the lane designated NORM are as in FIG. 7. The EBNA-1 proteins were prepared from Wi-L2 cell extracts as described in the Materials and Methods section.

FIG. 10 is a two-part graph (A and B) that illustrates a polypeptide P62 ELISA analysis of sequential serum samples from two patients with CMV-IM infections who had previous EBV infections. In FIG. 10 A for patient L.S., IgM antibody responses are shown as open circles, IgG responses are shown as closed circles, and the IgG/IgM ratios are shown as closed squares. In FIG. 10 B for patient S.G., the IgM responses are shown as open circles, whereas the IgG responses are shown as closed circles.

FIG. 11 contains two panels (A and B) that are photographs of immunoblot analysis of four sera from four patients with acute EBV-IM and six patients with acute CMV-IM. In panel A, the sera were immunoblotted on extracts from K562 cells (EBV⁻, CMV⁻), with IgM antibodies being specifically detected. In panel B, the sera were blotted on extracts from late CMV-infected human fibroblast cells, with IgG antibodies being detected. All sera were used at a 1:20 dilution. The letter designations "E" and "C" at the top of each lane designate the sera used in those lanes as being from patients with either EBV-IM or CMV-IM, respectively.

Figure 12:
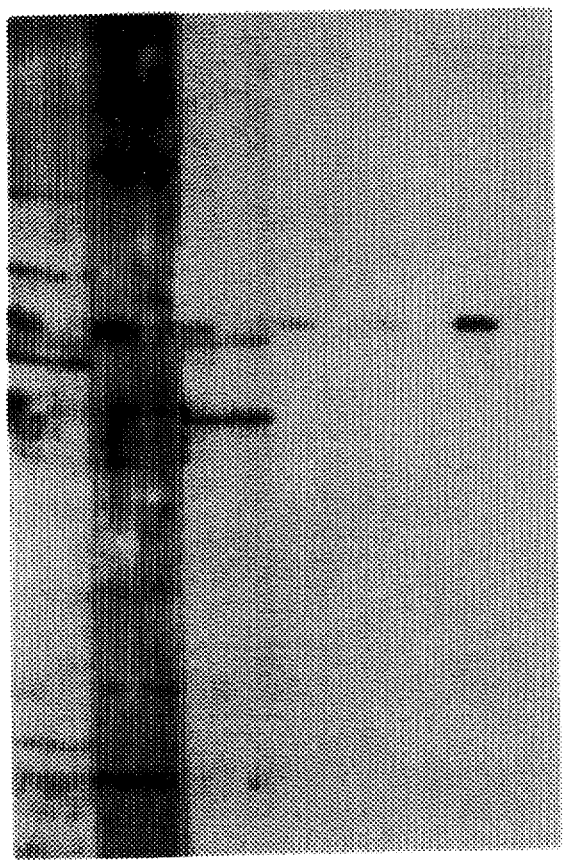

FIG. 12 is a photograph of an immunoblot that illustrates inhibition of binding of IgM and IgG from serum samples taken from patients D.B., D.S. and T.G. during acute and convalescent stages of their illness to extracts from Wi-L2 cells, an EBV⁺ B cell line. Patient G was a normal VCA⁺, EBNA-1⁺ donor. Lanes 1 and 2 contained serum samples from patient D.B. obtained 15 days post onset of disease (pod), lanes 3 and 4 were from patient D.S. 12 days pod, lanes 5 and 6 were from patient T. G. with acute IM taken 4 days pod, lanes 7 and 8 were from patient D.B. 514 days pod, lanes 10 and 11 were from patient D.S. 471 days pod, and lanes 11 and 12 were from the normal donor G. All serum samples were diluted 1:50. The odd numbered lanes contained only serum and are designated by minus signs (−), whereas the even numbered lanes contained serum plus polypeptide P62 and are designated by plus signs (+). The concentration of polypeptide P62 was 400 micrograms per milliliter (ug/ml) in lanes 2, 4 and 6, and was 50 ug/ml in lanes 8, 10 and 12. IgM antibodies were specifically detected in lanes 1–6, whereas IgG antibodies were specifically detected in lanes 7–12.

Figure 13:
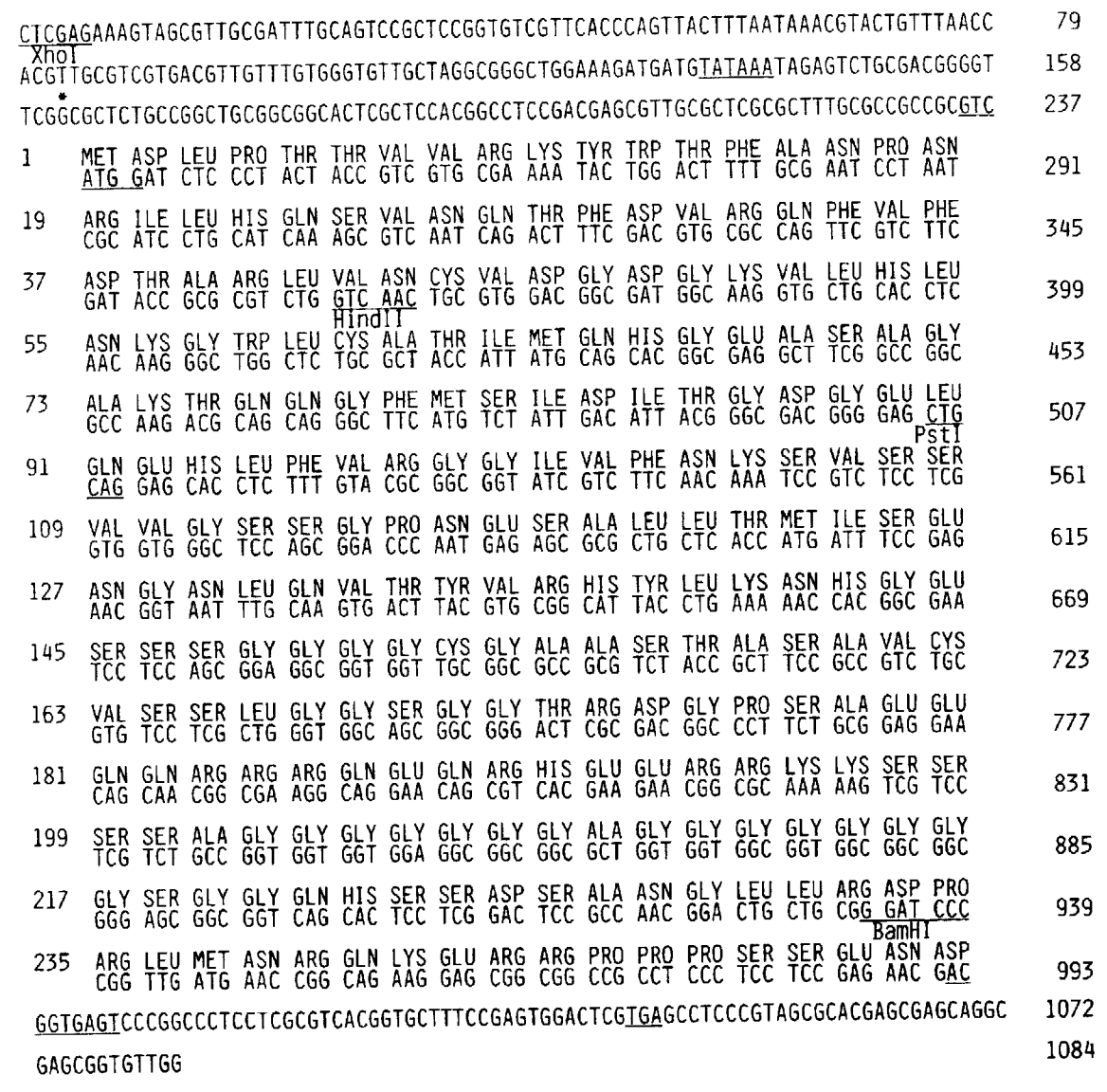

FIG. 13 illustrates the amino acid residue sequence of CMV-encoded polypeptide antigen, as described by Strapraus,et al., *J. Virol*, 57:591602 (1986). The numerical position of each residue in the sequence is indicated by the numbers in the left margin. Preferred CMV-homologous peptides of this invention include an amino acid residue sequence that corresponds to the sequence shown in the figure from about residue position 200 to about residue position 220.

Figure 14:
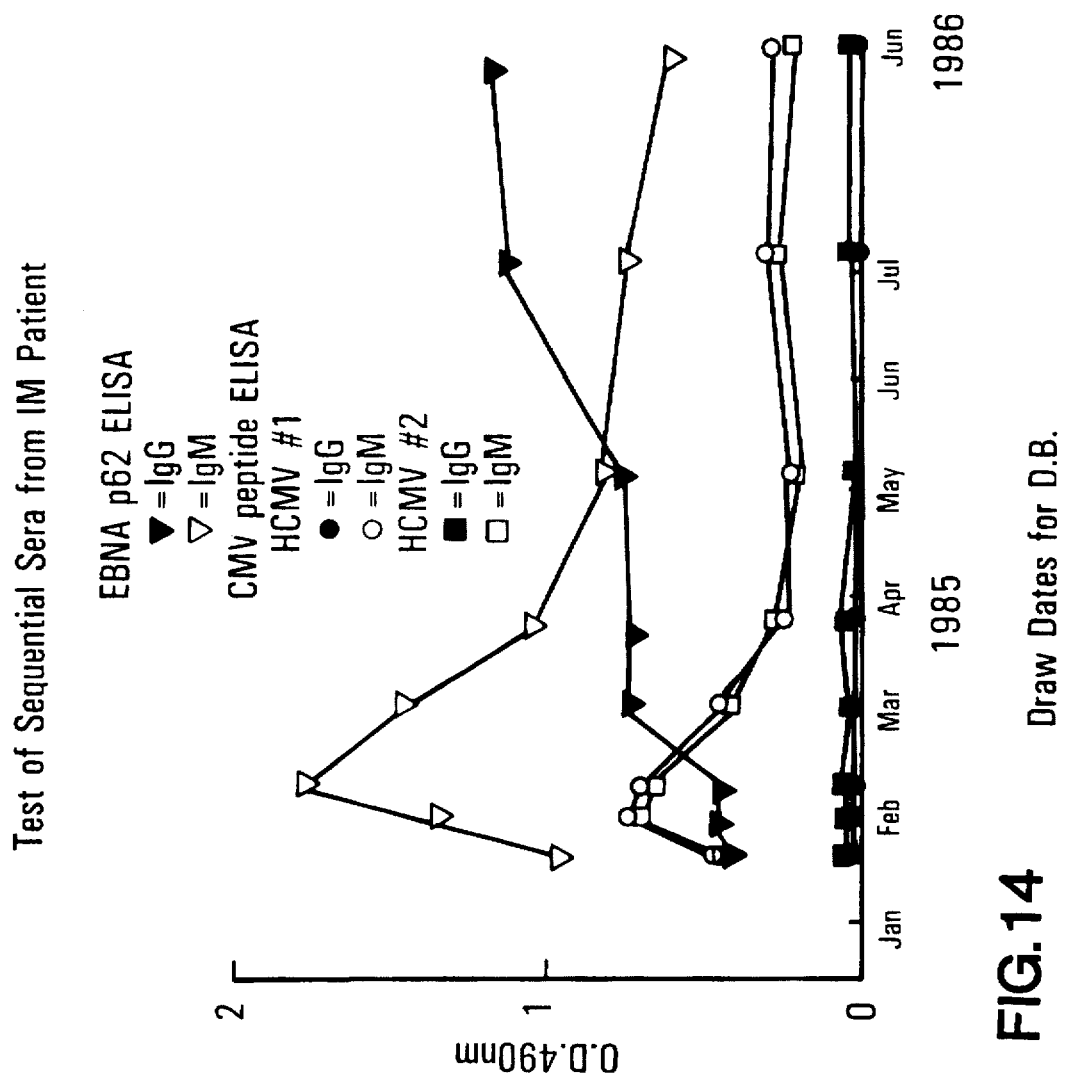

FIG. 14 is a graph illustrating the ability of EBV-homologous peptide P62 and CMV-homologous peptides C1 and C2 to detect anti-EBNA IgG (open symbols) or IgM (closed symbols) antibodies in the serum of patient DB over the course of an EBV infection. During the acute phase of the infection anti-EBNA IbM antibodies were detected using EB-homologous peptide P62 (triangles) CMV-homologous peptide C1 (circles) and CMV-homologous C2 (squares) ELISAs, confirming the presence of infectious mononucleosis. The onset of convalescence is indicated by the rise in anti-EBNA IgG, and concomitant fall in IgM, antibodies.

Figure 15:
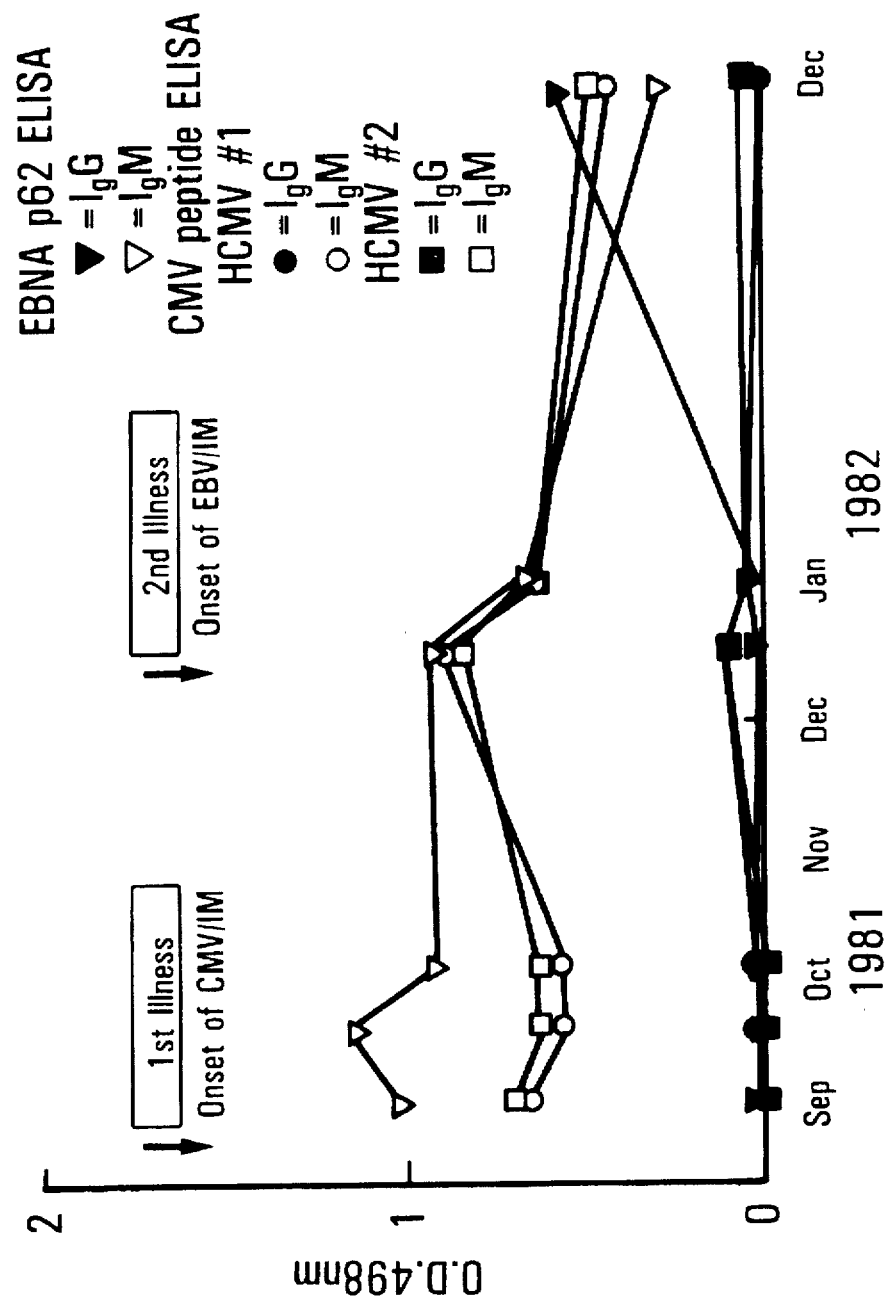

FIG. 15 is a graph illustrating the ability of EBV-homologous peptide P62 and CMV-homologous peptides C1 and C2 to detect anti-EBNA IgG (open symbols) or IgM (closed symbols) antibodies in the serum of patient DS over the course of the CMV infection followed by an EBV infection. During the acute phase of both illnesses, anti-EBNA IgM antibodies were detected using EBV-homologous peptide P62, CMV-homologous peptide C1 and CMV-homologous peptide C2 ELISAs, confirming the presence of infectious mononucleosis at the onset of each acute illness.

DETAILED DESCRIPTION OF THE INVENTION

I. Introduction

Humans infected with Epstein-Barr virus (EBV) develop antibodies against a viral nuclear antigen (EBNA) that is present in virally-transformed B lymphocytes. Traditional clinical techniques used to assay for EBNA and anti-EBNA antibodies in humans are cumbersome. In addition, current procedures for the purification of EBNA from cell culture are not readily adaptable to mass production.

The present invention contemplates the use of synthetic polypeptide technology to overcome some of the problems of the current methodologies. Short synthetic polypeptides may immunologically mimic antigenic determinants on a natural protein and may therefore be used to raise antibodies of predetermined specificity that recognize the natural protein.

The phrase "immunologically mimics" is used herein to mean that an immunogenic polypeptide of this invention induces production of antibodies that bind to the inducing polypeptide and also to the cognate sequence in the intact protein. This phenomenon may be used both experimentally and clinically.

Experimentally, antibodies to synthetic polypeptides may be used to establish the DNA reading frame, and therefore the amino acid residue sequence of a clinically important protein such as EBNA. Clinically, antibodies of predetermined specificity raised to synthetic polypeptides may be used for diagnostic and therapeutic purposes.

Heller et. al., *J. Virol.*, 44:311–320 (1982) reported a DNA nucleotide sequence with characteristics that indicated it might contain the gene coding for EBNA. They predicted that if the DNA was translated into protein, the three possible reading frames would code for an IR3 protein domain of more than 200 amino acid residues composed of only (i) serine, arginine, and glycine; (ii) glycine and alanine; or (iii) glutamine, glutamate, and glycine, depending upon the DNA reading frame expressed.

The reported chemical properties of the EBNA molecule, when taken together with the distribution of possible stop codons in the EBNA gene, indicated that the IR3 was composed primarily of glycine and alanine residues.

To assess that indication, short polypeptides were synthesized whose amino acid residue sequences substantially correspond to that of an EBNA protein whose IR3 is a glycine-alanine random copolymer.

As will be seen in the discussion that follows, those synthesized polypeptides, and one polypeptide in particular denominated P62, were found to immunologically mimic EBNA. In addition, a group of those particularly preferred polypeptides including polypeptide P62 were found to bind human anti-EBNA antibodies. The use of those polypeptides in various assay procedures is also discussed hereinafter.

More specifically in regard to such assays, an assay, preferably in the solid phase, that utilizes a particularly preferred polypeptide has been developed. That assay has been found to be clinically reliable in detecting infectious mononucleosis (IM) caused by EBV (EBV-IM) as well as IM induced by CMV (CMV-IM), and also in detecting nasopharyngeal carcinoma (NPC), another disease in which EBV has been implicated. Specific results with assays in each area are discussed as are the assay methods generally.

II. PREFERRED EMBODIMENTS

A. Synthetic Polypeptides

1. Sequences

The series of small synthetic polypeptides (5-21 amino acid residues in length) used in this study were synthesized using the solid phase method of Merrifield. Merrifield et. al., *J. Am. Chem. Soc.*, 85:2149–2154 (1963). The sequences were chosen to represent different areas from within and just outside the proposed IR3 region of the EBNA.

The term "synthetic" as used herein means that the polypeptide molecule or polypeptide repeating unit has been built up by chemical means; i.e., chemically synthesized, rather than being prepared by a biological means, as by genetic engineering techniques. Thus, the synthetic polypeptides embodying the present invention are free from naturally occurring proteins and fragments thereof.

The chemically synthesized polypeptides also therefore differ from degradation products of naturally occurring proteins as are prepared by the action of cyanogen bromide on the protein. The well-known solid phase chemical synthesis in which blocked amino acid residues are added in a serial manner to obtain the desired polypeptide is the preferred method of synthesis, and is discussed in greater detail hereinbelow.

All amino acid residues identified herein are in the natural or L-configuration. In keeping with standard polypeptide nomenclature, abbreviations for amino acid residues are as follows:

| SYMBOL | | |
|---|---|---|
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| Z | Glx | L-glutamic acid or L-glutamine |

| SYMBOL | | |
|---|---|---|
| 1-Letter | 3-Letter | AMINO ACID |
| W | Trp | L-tryptophan |
| R | Arg | L-arginine |
| D | Asp | L-aspartic acid |
| N | Asn | L-asparagine |
| B | Asx | L-aspartic acid or L-asparagine |
| C | Cys | L-cysteine |

One aspect of the invention contemplates a random copolymer polypeptide containing about 6 to about 40 amino acid residues, preferably about 15 to about 20 amino acid residues, and including the sequence defined by the formula written from left to right and in the direction of amino-terminus to carboxyl-terminus —Gly—R$^1$—Gly—R$^2$—Gly— wherein R$^1$ and R$^2$ designate amino acid residues which when taken individually are the same or different and are Ala, Asn, Arg, Gly, Leu, Pro, Ser and Thr, provided that R$^1$ and R$^2$ are not both Gly. The polypeptide also contains at least 25 mole percent glycine residues, and is capable, when linked to a carrier and introduced in an effective amount into a mammalian host, of inducing production of antibodies that immunoreact with EBNA.

In one preferred embodiment, R$^1$ and R$^2$ are both Arg so that the polypeptide includes the amino acid residue sequence: —Gly—Arg—Gly—Arg—G

TABLE I

SEQUENCES OF SYNTHETIC POLYPEPTIDES

| Peptide* | Sequence |
|---|---|
| P60(C) | H—Gly—Gly—Gly—Ala—Gly—Ala—Gly—Gly—Ala—Gly—Ala—Gly—Gly—Gly—Gly—Arg—OH; |
| P89 (D) | H—Arg—Ala—Arg—Gly—Arg—Gly—Arg—Gly—Arg—Gly—Glu—Lys—Arg—Pro—Met—OH; |
| F12 (E) | H—Ile—Met—Ser—Asp—Glu—Gly—Pro—Gly—Thr—Gly—Asn—Gly—Leu—Gly—Glu—OH; |
| F13 (F) | H—Pro—Gly—Ala—Pro—Gly—Gly—Ser—Gly—Ser—Gly—Pro—OH; |
| P27 (A) | H—Lys—Gly—Thr—His—Gly—Gly—Thr—Gly—Ala—Gly—Ala—Gly—Ala—Gly—Gly—Ala—Gly—Ala—Gly—OH; |
| P62 (B) | H—Ala—Gly—Ala—Gly—Gly—Gly—Ala—Gly—Gly—Ala—Gly—Ala—Gly—Gly—Ala—Gly—Gly—Ala—Gly—OH; |
| F14 | H—Gly—Gly—Ala—Gly—Gly—Ala—Gly—Gly—Ala—Gly—Ala—Gly—Gly—Gly—Ala—Gly—OH; |
| F15 | H—Gly—Ala—Gly—Gly—Ala—Gly—Ala—Gly—Gly—Gly—Ala—Gly—Gly—Ala—Gly—Gly—OH; |
| F16 (G) | H—Gly—Gly—Ala—Gly—Ala—Gly—Gly—Ala—Gly—Ala—Gly—Gly—Ala—Gly—Ala—Gly—Gly—Ala—Gly—Ala—Gly—OH; |
| C1 | H—Ala—Gly—Gly—Gly—Gly—Gly—Gly—Gly—Ala—Gly—Gly—Gly—Gly—Gly—Gly—Gly—Gly—Ser—Gly—Gly—OH |
| C2 | H—Ser—Ser—Ser—Ala—Gly—Gly—Gly—Gly—Gly—Gly—Gly—Ala—Gly—Gly—Gly—Gly—Gly—Gly—Gly—Gly—Ser—Gly—Gly—OH |
| C3 | H—Ser—Ser—Ser—Ser—Ala—Gly—Gly—Gly—Gly—Gly—Gly—Gly—Ala—Gly—Gly—Gly—Gly—Gly—Gly—Gly—Gly—Cys—OH |

*Parenthesized capital letters are used to designate the corresponding polypeptide in some of the Figures and Tables herein.

The results of polypeptide/anti-polypeptide receptor binding and binding inhibition studies are discussed hereinafter in section II D. Those results, illustrate cross-reactivities and cross-inhibitory effects that parallel the amount of sequence homology among the polypeptides. For example, polypeptide P60 contains a 10 amino acid segment homologous with P62. Polypeptide P27 contains an 8 amino acid segment homologous to polypeptides P60, P62 and D1 (Table 2). Polypeptide D2 (Table 2) contains a seven amino acid residue segment homologous to segments of polypeptides P27, P60, P62 and D1. Polypeptide P89 which did not significantly crossreact in the study, contains no sequence homology with polypeptides P27, P62, and P60.

More importantly, the 8 amino acid residue sequence shared by polypeptides P27, P62, P60 and D1 contains at least one antigenic determinant common to all three random copolymer polypeptides, thereby making those three polypeptides antigenically related variants. In addition, the shared segment includes the six amino acid residue sequence —Gly—Ala—Gly—Gly—Ala—Gly— and an overlapping sequence represented by the formula —Gly—R¹—Gly—R²—Gly— wherein R¹ and R² are both Ala; i.e., —Gly—Ala—Gly—Ala—Gly—.

By "overlapping", it is meant that the second-named sequence is contained in part of the first-named sequence. This overlapping of amino acid residue sequence is illustrated for polypeptide P62 by the overlapping, "boxed", sequence portions shown below in which the single letter amino acid residue code is used.

G—G—G—A—G—G—A—G—A—G—G—G—A—G—G

Random copolymer polypeptides that contain both the shared six amino acid residues-containing sequence and the overlapping five amino acid residue constitute a still more, particularly, preferred embodiment of this invention. In such particularly preferred embodiments, the random copolymer polypeptide of the present invention contains about 8 to about 40, and preferably about 15 to about 20, amino acid residues and includes, in addition to the before defined —Gly—R¹—Gly—R²—Gly— amino acid residue sequence, the sequence, written from left to right and in the direction of amino-terminus to carboxyl-terminus, represented by the formula, —Gly—Ala—Gly—Gly—Ala—Gly— contains at least about 50 mole percent Gly residues and is capable of both (a) inducing the production of antibodies that immunoreact with EBNA when linked to a carrier and introduced in an effective amount into a mammalian host, and (b) immunoreacting with human antibodies induced by natural EBNA.

Particularly preferred amino acid residue sequences include the sequences, taken from left to right and in the direction of amino-terminus to carboxyl-terminus, represented by the formulae:

| | |
|---|---|
| (i) | —Gly—Gly—Gly—Ala—Gly—Ala—Gly—Gly—Ala—Gly—Ala—Gly—Gly—Gly—Gly—Arg—; |
| (ii) | —Lys—Gly—Thr—His—Gly—Gly—Thr—Gly—Ala—Gly—Ala—Gly—Ala—Gly—Gly—Ala—Gly—Ala—Gly—; |
| (iii) | —Ala—Gly—Ala—Gly—Gly—Gly—Ala—Gly—Gly—Ala—Gly—Ala—Gly—Gly—Gly—Ala—Gly—Gly—Ala—Gly—; |
| (iv) | —Gly—Gly—Ala—Gly—Gly—Ala—Gly—Gly—Ala—Gly—Ala—Gly—Gly—Gly—Ala—Gly—; |
| (v) | —Gly—Ala—Gly—Gly—Ala—Gly—Ala—Gly—Gly—Gly—Ala—Gly—Gly—Ala—Gly—Gly—; |
| (vi) | —Gly—Gly—Ala—Gly—Ala—Gly—Gly—Ala—Gly—Ala—Gly—Gly—Ala—Gly—Ala—Gly—Gly—Ala—Gly—Ala—Gly—; |
| (vii) | —Gly—Gly—Gly—Ala—Gly—Gly—Ala—Gly—Ala—Gly—Gly—Gly—Ala—Gly—Ala—Gly—; |
| (viii) | —Ala—Gly—Gly—Ala—Gly—Ala—Gly—Gly—Gly—Ala—Gly—Ala—Gly—; | pharmaceutically acceptable salts thereof, and antigenically related variants thereof.

It is noted that a dash at the beginning or end of an amino acid residue sequence indicates a bond to a radical such as H and OH, at the amino- and carboxyl-termini, respectively, or a further sequence of one or more amino acid residues up to a total of forty amino acid residues in the polypeptide chain.

Also particularly preferred are the corresponding polypeptides themselves, that is, polypeptides P60, P27, P62, F14, F15, and F16 shown in Table 1 and D1 and D2 shown in Table 2, and the pharmaceutically acceptable salts thereof and antigenically related variants thereof. Polypeptide P62 is used illustratively herein as an example of the particularly preferred polypeptides. Polypetide P62 is also sometimes designated P62, peptide P62, EBNA P62, and the like, with the understanding that any designation that includes "P62" refers to that material. The words "peptide" and "polypeptide" are used interchangeably herein.

The phrase "pharmaceutically acceptable salts", as used herein, refers to non-toxic alkali metal, alkaline earth metal and ammonium salts used in the pharmaceutical industry, including the sodium, potassium, lithium, calcium, magnesium and ammonium salts and the like that are prepared by methods well-known in the art. The phrase also includes non-toxic acid addition salts that are generally prepared by reacting the compounds of this invention with a suitable organic or inorganic acid. Representative salts include the hydrochloride, hydrobromide, sulfate, bisulfate, acetate, oxalate, valerate, oleate, laurate, vorate, benzoate, lactate, phosphate, tosylate, citrate, maleate, fumarate, succinate, tartrate, and the like.

In another preferred embodiment, the present invention contemplates a polypeptide containing at least about 15 to no more than about 40 amino acid residues having a sequence homologous (corresponding) to the sequence of EBNA or the CMV encoded polypeptide shown in FIG. 13 and including the before described formula, —Gly—R$^{1-}$Gly—R$^2$—Gly$^-$. EBNA-homologous and CMV-homologous peptides of the present invention are further characterized as having the ability to immunoreact with anti-EBNA antibodies.

2. Size

The effect of changing the size of the synthetic polypeptide on its ability to be bound by anti-EBNA antibodies was studied. It was generally found that as polypeptide size is decreased, its ability to be bound by antibodies also decreased.

Polypeptide P62 consists of 20 amino acid residues of which the first nine residues from the amino-terminus are directly repeated, as shown in Table 2 using the single letter code for amino acid residues. A series of polypeptides homologous to P62 was synthesized in which amino acid residue triads were deleted from the amino-terminus of the preceding peptide to provide polypeptides D1, D2 and D3 as are shown in Table 2, below. Increasing portions of the sequence symmetry of P62 are therefore missing in polypeptides D1, D2 and D3.

TABLE 2

| Polypeptide Designation | Acid Residue Sequence# |
|---|---|
| P62: | A G A G G G A G G*A G A G G G A G G A G |
| D1: | G G G A G G A G A G G G A G G A G |
| D2: | A G G A G A G G G A G G A G |
| D3: | A G A G G G A G G A G |
| A5: | G G G A G |
| A6: | A G G G A G |
| A7: | G A G G G A G |
| A8: | A G A G G G A G |
| A9: | G A G A G G G A G |

Polypeptide sequences using the single letter code are shown in the direction from left to right and from amino-terminus to carboxyl-terminus.
*Junction of 9-mer direct repeat in polypeptide P62.

The ability of the D series of polypeptides to immunoreact with 3 human anti-EBNA sera and rabbit anti-P62 serum was studied using the polypeptides in the solid phase of the ELISA, described hereinafter. Antibody binding to D1 was nearly the same as that to the parent polypeptide P62 for all sera tested. In contrast, there was no binding to solid phase D3 for any serum except rabbit anti-P62. The results for D2 were intermediate and were dependent upon the serum tested. Thus, antibody recognition of this series of polypeptides was decreased as polypeptide length was shortened from 20 to 11 amino acid residues.

The fact that antibody binding fell off for all the antisera argues against the possibility that a specific antigenic determinant was being deleted by the sequential elimination of amino acid residues since the polypeptides contained two antigenic determinants, only one of which was affected by the sequence deletions. Also, the sequence symmetry of P62 assured that all sequences of four to eight amino acid residues that were present in P62 were also in D3, with the exception of those across the junction of the repeat.

Conformational changes in the polypeptides bound to the solid support in the ELISA may have contributed to the suppression of antibody recognition. This possibility was studied by inhibiting the binding (immunoreacting) of several sera to solid phase-bound P62 by use of varying concentrations of competing polypeptides in solution. The antisera were admixed and maintained (incubated) with polypeptide P62, D1, D2 or D3 in solution for a predetermined time sufficient for immunoreaction (binding) to occur before being added to a microtiter plate coated with P62. The results of this study with sera from five patients are summarized in Table 3 below.

TABLE 3

Concentration of Competing Polypeptides Providing 50% Inhibition of Antibody Binding to Peptide P62*

| | Competing Peptide (micrograms per milliliter) | | | |
|---|---|---|---|---|
| Sera | P62 | D1 | D2 | D3 |
| TJ | 0.05 | 0.05 | 0.1 | 200 |
| VM | 0.3 | 0.3 | 0.4 | 3 |
| CV | 0.1 | 0.1 | 0.1 | 10 |
| N6 | 0.6 | 0.6 | 0.6 | 3 |
| JC | 1 | 1 | 1 | 500 |

*The ELISA procedures used for these determinations are described hereinafter in sections II E(2) and III/D.

The inhibitory action of polypeptide D1 on antibody binding to P62 is considered indistinguishable from the inhibitory effect of P62 itself. This is true for all sera tested.

More interestingly, polypeptide D3 inhibited some of the sera, VM and N6, about as well as the larger polypeptides did. This strong inhibitory effect occurred despite the fact that neither of those sera showed any binding to D3 bound to the solid support in the ELISA. These data are believed to indicate that the polypeptide must be of a certain minimum length, at least about 15 amino acid residues, to maintain required secondary structure when bound to the plastic surface of a microtiter plate. Thus, for solid phase assays, a peptide length of about 15 to about 40 residues is preferred, with a length of about 15 to about 20 residues being more preferred.

The minimum antigen size necessary for recognition was further studied using polypeptides A5, A6, A7, A8 and A9. As shown in Table 2, polypeptide A5 has five amino acid residues, and each member of the series A6-A9 was increased in length by one amino acid residue over the 5 preceding polypeptide up to the nine residues present in A9. No antiserum tested immunoreacted with these polypeptides when they were bound to microtiter plates in the ELISA described hereinafter.

The data for ability of the A series polypeptides to inhibit binding of human anti-EBNA antibodies to solid phase P62 is shown in Table 4 below.

TABLE 4

Inhibition of Antibody Binding to Peptide
P62 By 100 micrograms per milliliter
Competing Peptide*

| Sera | Percent of Uninhibited Activity | | | | |
|------|-----|-----|-----|-----|-----|
|      | A5  | A6  | A7  | A8  | A9  |
| TJ   | 96  | 80  | 91  | 74  | 31  |
| VM   | 93  | 81  | 51  | 17  | 9   |
| CV   | 92  | 93  | 93  | 72  | 20  |
| JC   | 94  | 92  | 60  | 88  | 74  |
| S62  | 86  | 96  | 89  | 95  | 78  |
| S60  | 106 | 109 | 93  | 84  | 53  |

*These studies were carried out as described for Table 3.

Almost all sera tested were inhibited by A9 although very high concentrations were required (more than 100-fold higher than the concentrations of P62 or D1 needed for equivalent inhibition). In addition, three sera immunoreacted with and were inhibited by A8 and one by A7. None were inhibited by the shorter polypeptides A6 and A5.

Thus, the decrease in immunoreactivity that parallels a decrease in polypeptide size appears to be due to two effects: (1) the effect of deletion of the site on the antigen to which the antibody binds as shown by the A series polypeptides and, (2) the change in the conformation of the polypeptide as its size decreases as shown by the D series polypeptides.

3. Conformation

The conformational properties of the polypeptides of this invention were studied using circular dichroism (CD) spectroscopy. The CD spectra of polypeptides P27, P60, P62, F13, F15 and F16 were determined. The data, partially shown in FIG. 1, indicate that the polypeptides of this invention which include both of the preferred amino acid residue sequences; i.e.,

wherein $R^1$ and $R^2$ are as described before, and

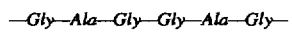

adopt a relatively stable secondary structure or conformation in a physiological solution at 20° C. Since the predominant conformation of those polypeptides is relatively stable, it is believed that human anti-EBNA antibody activity occurs in response to this particular conformation.

B. Multimers

The present invention also contemplates a multimeric polypeptide (multimer) containing a plurality of joined random copolymer polypeptide repeating units wherein at least one of the repeating units is a polypeptide as described herein.

The multimers of this invention, alone or linked to a carrier, when introduced in an effective amount into a mammalian host, are capable of inducing the production of antibodies that bind to EBNA. Particularly preferred multimers are those that contain a CMV-homologous polypeptide of this invention capable of binding human antibodies induced by EBNA.

Thus, the multimers of this invention, like their constituent polypeptides, are immunogenic, and are antigenic to human anti-EBNA antibodies. Those multimers may therefore be used to induce the production of anti-EBNA antibodies that are useful in the diagnostic methods and systems discussed hereinafter, and may also be used as an antigen in appropriate diagnostic methods and systems.

Multimers that contain fewer than about 35 amino acid residues in the total multimer are typically linked to a carrier for use as an immunogen. Those multimers that contain more than a total of about 35 amino acid residues are typically sufficiently immunogenic to be used without a carrier.

Polypeptide multimers may be prepared by bonding together the polypeptide monomers in a head-to-tail manner using the aforementioned solid phase method; i.e., one complete polypeptide sequence can be synthesized on the resin, followed by one or more of the same or different polypeptide sequences, with the entire multimeric unit thereafter being cleaved from the resin and used as described herein. Such head-to-tail polypeptide multimers preferably contain about 2 to about 4 polypeptide repeating units.

Alternatively, multimers can be prepared as a polymer of random copolymer polypeptides used as monomers. As used herein, the term "polymer" in its various grammatical forms is defined as a type of multimer that contains a plurality of random copolymer polypeptide repeating units that are joined together by other than peptide bonds.

An exemplary polymer of this invention can be synthesized using the polypeptide monomers of this invention that contain added cysteine residues at both the amino- and carboxyl-termini (diCys polypeptide). The diCys polypeptide monomers may be bonded together by intramolecular, interpolypeptide cysteine disulfide bonds utilizing an oxidation procedure to form an immunogenic, antigenic polymer. The polymer so prepared contains a plurality of the random copolymer polypeptides of this invention as repeating units. Those repeating units are bonded together by the above-discussed oxidized cysteine (cystine) residues.

The presence of one or two terminal Cys residues in a polypeptide of this invention for the purposes of binding the polypeptide to a carrier or for preparing a polymer is not to be construed as altering the amino acid sequence of polypeptide repeating units of this invention.

C. Inocula

In another embodiment, the polypeptides of this invention are used in a pharmaceutically acceptable diluent to form an inoculum or a vaccine that, when administered in an effective amount, is capable of inducing antibodies that immunoreact with EBNA.

The word "inoculum" in its various grammatical forms is used herein to describe a composition containing a polypeptide of this invention as an active ingredient used for the preparation of antibodies against EBNA. When a polypeptide is used to induce antibodies it is to be understood that the polypeptide may be used alone, linked to a carrier or as a multimer, but for ease of expression, these alternatives will not always be expressed hereinafter.

For polypeptides that contain fewer than about 35 amino acid residues, it is preferable to use a carrier for the purpose of inducing the production of antibodies. A polypeptide bound or linked to a carrier will be used illustratively herein where antibodies are being prepared.

The inoculum can be used to produce antibodies for use in a diagnostic assays that detect cells expressing EBNA. The antibodies produced by the inoculummay also be used in a preparation for inducing passive immunity against B lymphocytes expressing EBNA on their cell surfaces.

The word "vaccine" in its various grammatical forms is used herein to describe a type of inoculum containing a polypeptide of this invention as an active ingredient that is used to induce active immunity in a host mammal. Since active immunity involves the production of antibodies, a vaccine or inoculum may thus contain identical ingredients, but their uses are different. In most cases, the ingredients of a vaccine and of an inoculum are different because many adjuvants useful in animals may not be used in humans.

The present inoculum or vaccine contains an effective amount of a polypeptide of this invention, as a multimer such as a polymer of individual polypeptides linked together through oxidized, polypeptide terminal cysteine residues or as a conjugate linked to a carrier. However, for ease of expression, the various embodiments of the polypeptides of this invention are collectively referred to herein by the term "polypeptide," and its various grammatical forms.

The effective amount of polypeptide per unit dose depends, among other things, on the species of animal inoculated, the body weight of the animal and the chosen inoculation regimen as is well known in the art. Inocula and vaccines typically contain polypeptide concentrations of about 10 micrograms to about 500 milligrams per inoculation (dose). The stated amounts of polypeptide refer to the weight of polypeptide without the weight of a carrier, when a carrier is used. Specific, exemplary inocula are described hereinafter with weight of carrier plus polypeptide (conjugate) being given.

The term "unit dose" refers to physically discrete units suitable as unitary dosages for animals, each unit containing a predetermined quantity of active material calculated to produce the desired therapeutic effect in association with the required diluent; i.e., carrier, or vehicle. The specifications for the novel unit dose of this invention are dictated by and are directly dependent on (a) the unique characteristics of the active material and the particular therapeutic effect to be achieved, and (b) the limitations inherent in the art of compounding such active material for therapeutic use in animals, as disclosed in detail in the specification, these being features of the present invention.

Inocula are typically prepared from the dried solid polypeptide-conjugate or polypeptide polymer by suspending the polypeptide-conjugate or polypeptide polymer in a physiologically tolerable (acceptable) diluent such as water, saline or phosphate-buffered saline.

Inocula may also include an adjuvant. Adjuvants such as complete Freund's adjuvant (CFA), incomplete Freund's adjuvant (IFA) and alum are materials well known in the art, and are available commercially from several sources.

D. Receptors

Antibodies and substantially whole antibodies raised to (induced by) the polypeptides of this invention as well as antibody combining sites prepared from such antibodies constitute still another embodiment of this invention. These molecules are collectively referred to herein as receptors. Receptors are raised in mammalian hosts such as mice, rabbits, horses and the like by immunization using the inocula described hereinabove.

Suitable monoclonal receptors, typically whole antibodies, may also be prepared using hybridoma technology described by Niman et. al., *Proc. Natl. Sci., U.S.A.*, 80:4949-4953 (1983), which description is incorporated herein by reference. Briefly, to form the hybridoma from which the monoclonal receptor is produced, a myeloma or other self-perpetuating cell line is fused with lymphocytes obtained from the spleen of a mammal hyperimmunized with a polypeptide of this invention.

It is preferred that the myeloma cell line be from the same species as the lymphocytes. Typically, a mouse of the strain 129 GIX$^+$ is the preferred mammal. Suitable mouse myelomas for use in the present invention include the hypoxanthine-aminopterin-thymidine-sensitive (HAT) cell lines P3X63-Ag8.653 (ATCC CRL 1580), and Sp2/0-Ag14 (ATCC CRL 1581).

Splenocytes are typically fused with myeloma cells using polyethylene glycol (PEG) 1500. Fused hybrids are selected by their sensitivity to HAT. Hybridomas producing the receptor molecules of this invention are identified using the enzyme linked immunosorbent assay (ELISA) described in the Materials and Methods section III D hereinafter.

Monoclonal receptors need not only be obtained from hybridoma supernatants, but may also be obtained in generally more concentrated form from ascites fluid of mammals into which the desired hybridoma has been introduced. Production of monoclonal antibodies using ascites fluid is well known and will not be dealt with further herein.

A receptor of this invention binds both to the polypeptide to which it was raised and also binds to the corresponding EBNA antigenic determinant site the polypeptide of this invention immunologically mimics. Thus, a polypeptide of this invention may be both an immunogen and an antigen.

The receptors of this invention may be described as being oligoclonal as compared to naturally occurring polyclonal antibodies since they are raised to an immunogen having relatively few epitopes as compared to the epitopes of an intact EBNA molecule. Consequently, receptors of this invention bind to epitopes of the polypeptide while naturally occurring antibodies raised to EBNA bind to epitopes throughout the EBNA molecule.

Exemplary receptor molecules containing antibody combining sites of this invention raised in rabbits to the polypeptides shown in Table 1 were studied using the immunoblotting procedures of Towbin, et. al., *Proc. Natl. Acad. Sci., U.S.A.*, 76:4350-4354 (1979) and Billings, et. al., *Proc. Natl. Acad. Sci., U.S.A.*, 80:7104-7108 (1983). Further details are provided in the Materials and Methods section (III).

It was found that all the polypeptides of this study elicited rabbit anti-polypeptide antibodies when linked to a protein carrier as a conjugate and introduced in an effective amounts into rabbit hosts in an inoculum as described hereinafter. These receptor molecules recognized intact EBNA protein isolated from the EBV-transformed human B lymphoblast cell lines WI-L2, Raji and Daudi. Data from these studies are partially shown in FIG. 2. In control studies, protein extracts of B lymphocytes negative for EBV infection (BJAB cells; available at the Scripps Clinic and Research Foundation, La Jolla, Calif.) failed to yield reactive bands with the anti-polypeptide antisera. These data indicate that exemplary receptor molecules of this invention immunoreact with an EBV infection-specific protein.

Figure 2:
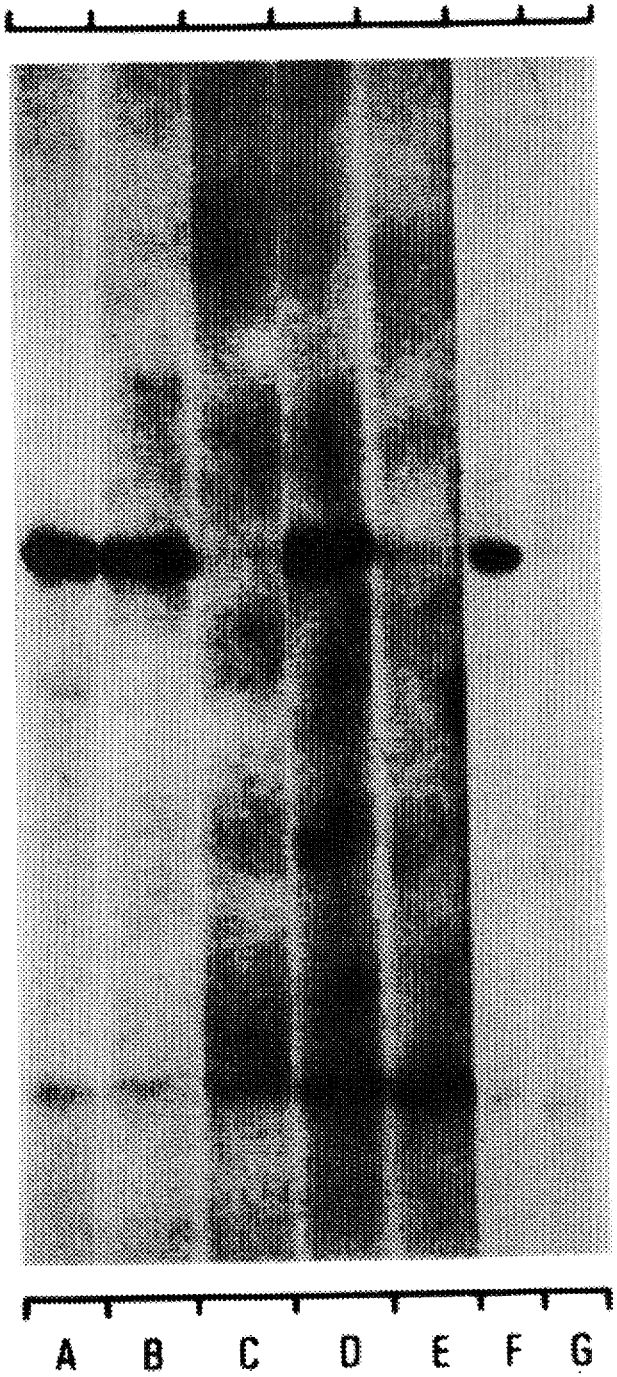
FIG. 2 is a photograph of nitrocellulose immunoblots of whole cell extracts of EBV-transformed WI-L2 cells using rabbit antipeptide antisera to synthetic polypeptides C (P60) and B (P62). A human serum (from patient TJ) previously defined as anti-EBNA positive; i.e., containing anti-EBNA antibodies, was used as a positive control in lane A at a 1:20 dilution. Rabbit anti-P60 (C) serum at a 1:50 dilution (lane B) and rabbit anti-P62 (B) serum at 1:10 (lane D) immunoreacted with the same band as the positive control indicating they recognize natural EBNA. Lanes A-G are identified at the bottom of the Figure.

In addition, it was found that the immunoreactivity of the rabbit anti-polypeptide antibodies for intact EBNA protein could be blocked by the inducing, immunogenic polypeptide used as an antigen, as is also shown in FIG. 2. These results demonstrate that the idiotypes (antibody-combining sites) of the anti-polypeptide antisera were specific for EBNA antigenic determinants.

The rabbit anti-polypeptide antibody to polypeptide P62 was used in a competition study to examine the antigenic relatedness of polypeptides P27, P62, P60 and P89. This antibody cross-reacted extensively with the conjugated and non-conjugated polypeptides in the ELISA described hereinafter. The binding of anti-polypeptide P62 to polypeptide P62 in the solid phase was inhibited 98 percent by first incubating the antibody with polypeptide P62. In the same manner, the binding of anti-polypeptide P62 to polypeptide P62 was inhibited 81% by polypeptide P60, and 36% by polypeptide P27. Polypeptide P89 did not inhibit anti-polypeptide P62 reactivity at all.

To determine whether or not the antibodies in human EBV-immune serum also recognized this antigenic determinant, a competition study was performed using the serum of an EBV-immune, rheumatoid arthritis patient (serum 1011). The results, shown in FIG. 3, were similar to those obtained when anti-polypeptide-P62 was used. This indicates that the antigenic determinant shared by polypeptides P27, P62 and P60 mimics a naturally occurring immunogenic determinant of EBNA.

E. Diagnostic Assays Systems and Methods

The polypeptides, antibodies and antibody combining sites (receptors) raised to the before described polypeptides, and methods of the present invention may also be used for diagnostic tests, such as immunoassays. Such diagnostic techniques include, for example, enzyme immune assay, enzyme multiplied immunoassay technique (EMIT), enzyme-linked immunosorbent (ELISA), radioimmunoassay (RIA), florescence immune assay, either single or double antibody techniques, and other techniques in which either the receptor or the antigen is labeled with some detectable tag or indicating means. See generally Maggio, *Enzyme Immunoassay*, CRC Press, Cleveland, Ohio (1981); and Goldman, M., *Fluorescent Antibody Methods*, Academic Press, New York, N.Y. (1980). Specific examples of such assay methods and systems useful in carrying out those methods are discussed hereinbelow.

1. Assays For EBNA

A method for assaying for the presence of EBNA in a body sample is also contemplated herein. In a general method, a body sample to be assayed is provided, and is admixed with receptor molecules that contain an antibody combining site raised to a random copolymer polypeptide of this invention. The admixture is maintained for a predetermined period of time sufficient for the receptor molecules to immunoreact with EBNA present in the body sample. The amount of that immunoreaction is then measured to determine whether EBNA molecules were present or absent in the assayed body sample.

An illustrative diagnostic system in kit form embodying one aspect the present invention that is useful for detecting EBNA present in an aliquot of a body sample contains receptor molecules of this invention such as antibodies, substantially whole antibodies, or antibody combining sites like Fab and F(ab')$_2$ antibody portions raised to a polypeptide of this invention in one package. This system also includes an indicating means for signaling the presence of an immunoreaction between the receptor and the antigen.

Typical indicating means include radioisotopes such as $^{125}$I and $^{131}$I, enzymes such as alkaline phosphatase, horseradish peroxidase, beta-D-galactosidase and glucose oxidase, and fluorochrome dyes such as fluorescein and 5 rhodamine. The indicating means may be linked directly to receptor of this invention. The indicating means may also be linked to a separate molecule such as to a second antibody, to an antibody combining site or to *Staphylococcus aureus* (*S. aureus*) protein A that reacts with (binds to), the receptor of this invention. A specific example of such a separate molecule indicating means is $^{125}$I-labeled *S. aureus* protein A.

The indicating means permits the immunoreaction product to be detected, and is packaged separately from the receptor when not linked directly to a receptor of this invention. When admixed with a body sample such as an acetone-fixed peripheral blood lymphocyte (PBL) smear, the receptor molecule immunoreacts with the EBNA to form an immunoreactant, and the indicating means present then signals the formation of immunoreaction product.

One embodiment of an EBNA diagnostic method is an immunofluorescent assay that includes an amplifying reagent. In such an assay a PBL smear is acetone-fixed to a plain microscope slide. An aliquot of antibodies raised in accordance with this invention, e.g., raised in rabbits, generally about 10 micrograms to about 500 micrograms, is contacted with the slide using well-known techniques.

After rinsing away any un-immunoreacted antibodies of this invention, any non-specific binding sites on the slide are typically blocked with a protein such as bovine serum albumin (BSA), if desired. A second reagent (amplifying reagent) such as complement, or anti-immunoglobulin antibodies, e.g., guinea pig complement, can then be incubated on the test slide.

After this second incubation, any unreacted amplifying reagent is removed as by rinsing leaving only that which is bound to the first-named antibodies on the assay slide. A third reagent (indicating means), e.g., antibody, like goat anti-guinea pig complement, is then incubated on the test slide. The third reagent is labeled by being linked to a fluorochrome dye such as fluorescein isothiocyanate (FITC), rhodamine B isothiocyanate (RITC), tetramethylrhodamine isothiocyanate (TRITC), 4,4'-diisothiocyanostilbene-2,2'-disulfonic acid (DIDS), and the like as are well known in the art.

Any unreacted third reagent is rinsed off after this third incubation, leaving any FITC labeled goat-antiguinea pig complement antibodies that bind to the complement on the test slide. The presence of the FITC labeled third reagent may be detected using florescence microscopy and thereby signal the presence of EBV infection.

B lymphocytes known to be infected with EBV were tested for the presence of EBNA using the immunofluorescence assay method described above and in more detail in the Materials and Methods section III. Rabbit antibodies raised to each of the polypeptides shown in Table 1 were able to detect EBNA in the EBV infected cell line WI-L2.

A preferred diagnostic system, preferably in kit form, useful for carrying out the above assay method includes, in separate packages, (a) receptors (antibodies) of this invention that immunoreact with EBNA, (b) a second, amplifying reagent such as complement, like guinea pig complement, anti-immunoglobulin antibodies or *S. aureus* protein A that reacts with the receptor, and (c) an indicating means that may be linked directly to the amplifying means or may be a portion of a separate molecule such as an antibody or antibody-portion that reacts with the amplifying reagent. The indicating means indirectly signals the immunoreaction of the receptor molecule and EBNA through the mediation of the amplifying reagent.

Receptor molecules and separate indicating means of any diagnostic system described herein, as well as the above-described amplifying reagent, may be provided in solution, as a liquid dispersion or as a substantially dry powder, e.g., in lyophilized form. Where the indicating means is a separate molecule from the amplifying reagent, it is preferred that the indicating means be packaged separately. Where the indicating means is an enzyme, the enzyme's substrate may also be provided in a separate package of the system. A solid support such as the before-described microscope slide, one or more buffers and acetone may also be included as separately packaged elements in this diagnostic assay system.

The packages discussed herein in relation to diagnostic systems are those customarily utilized in diagnostic systems.

Such packages include glass and plastic (e.g., polyethylene, polypropylene, polystyrene and polycarbonate) bottles, vials, plastic and plastic-foil laminated envelopes and the like.

The use of whole, intact, biologically active antibodies is not necessary in many diagnostic systems such as the immunofluorescent assay described above. Rather, only the immunologically active, idiotype-containing, antigen binding and recognition receptor site; i.e., the antibody combining site, of the antibody molecule may be used. Examples of such antibody combining sites are those known in the art as Fab and F(ab')$^2$ antibody portions that are prepared by proteolysis using papain and pepsin, respectively, as is well known in the art.

2. Assays For Anti-EBNA Antibodies (a) Assays Generally

Another diagnostic method of this invention is an assay such as an ELISA that detects anti-EBNA antibodies in an antibody-containing liquid body sample. Here, an EBV-homologous or CMV-homologous polypeptide of this invention such as polypeptide P62, C1, C2, C3 is used as an antigen, and is preferably bound on (adsorbed to) or otherwise linked or affixed to a solid matrix such as the cross-linked dextran available under the trademark SEPHADEX from Pharmacia Fine Chemicals (Piscataway, N.J.), agarose, beads of glass, polyvinyl chloride, polystyrene, cross-linked acrylamide, nitrocellulose, the wells of a microtiter plate or the surface of a dip stick or spoon, to form a solid support.

The EBV-or CMV-homologous polypeptide is admixed with the liquid body sample to be assayed. The immunoreaction admixture thus formed is maintained for a predetermined time sufficient for any anti-EBNA antibodies present in the body sample to immunoreact with the polypeptide. The presence of that immunoreaction is then determined as with an indicating means to signal the presence of anti-EBNA antibodies in the assayed body sample.

An exemplary ELISA utilizing the above method uses a solid support comprised of a EBV-or CMV-homologous polypeptide of this invention adsorbed (affixed) onto a solid matrix, each as the wells of a twelve or ninety-six well microtiter plate made of polystyrene or polyvinyl chloride, of an opaque double-welled plastic spoon as is described hereinafter in the Materials and Methods section, and the like. Non-specific binding sites on the solid matrix are thereafter typically blocked with a protein that does not include a sequence to which anti-EBNA antibodies bind or immunoreact such as bovine serum albumin (BSA). Unbound polypeptide and BSA are removed from the matrix as by rinsing.

A body sample aliquot such as human saliva, serum, blood or plasma is admixed with the above-described solid support to form immunoreaction admixture containing solid and liquid phases. The solid/liquid phase admixture is maintained for a time period (e.g., 2–60 minutes) sufficient for any anti-EBNA antibodies in the body sample to immunoreact with the polypeptide antigen and form a solid phase-bound immunoreactant. The solid and liquid phases are thereafter generally separated.

A solution of a second, labeled, indicating means-containing antibody, antibody combining site or S. aureus protein A that reacts with the first-named, anti-EBNA antibody is then admixed with the solid phase to form another or second solid/liquid phase immunoreaction admixture. An exemplary second antibody is a horseradish peroxidase (HRPO)-labeled goat anti-human Ig antibody where the first-named antibodies are from a human body sample. Additional, useful enzyme labels include alkaline phosphase, beta-D-galactosidase and glucose oxidase. The admixture formed from the solid phase and the second, labeled antibody solution is maintained (incubated) for a predetermined time period (e.g., 2–30 minutes) sufficient to form a second, solid phase-bound immunoreactant between the first-named antibody and the indicating means-containing entity such as an immunoreaction between the two antibodies. The solid and liquid phases are thereafter separated.

The second antibody described above may also be specific for and immunoreact with only one of the classes of immunoglobulin (e.g., IgG, IgM, IgE, IgA, or IgD) such as murine anti-IgG, anti-IgM or anti-IgA monoclonal antibodies or their combining site-containing portions. Such antibodies provide the ability to identify the immunoglobulin class of anti-EBNA antibody present in the body sample, as is shown in Tables 6–10, hereinafter. In addition, the second antibody or antibody combining site may be specific for and immunoreact with only one of the two types of immunoglobulin light chains (e.g., kappa or lambda). These antibodies provide the ability to identify the isotype of the immunoglobulin molecule present in the body sample.

A solution containing a substrate for the enzyme label such as hydrogen peroxide for peroxidase and a color-forming dye precursor such as o-phenylenediamine, or p-nitrophenyl phosphate for alkaline phosphatase is thereafter admixed with the solid phase, and that admixture is maintained for another preselected period of time. The optical density at a preselected wavelength (e.g., 490 or 405 nanometers, respectively) may then be determined after the predetermined time period has elapsed (e.g., 60 minutes), and compared to the optical density of a control to determine whether anti-EBNA antibodies were present in the body sample.

In another embodiment of the above assay, two solid supports are utilized. Each solid support comprises an EBV-homologous random copolymer polypeptide affixed to a solid matrix.

A first aliquot of a patient's liquid body sample such as blood, plasma or serum is admixed with the first solid support to form a solid/liquid phase admixture. The admixture is maintained for a predetermined time period (e.g. about 2 to 30 minutes) sufficient for any anti-EBNA antibodies present in the sample to immunoreact with the polypeptide and form a solid phase-bound immunoreactant containing the anti-EBNA antibodies. Analogous steps are carried out with a second aliquot of the patient's liquid body sample and the second solid support. Of course, the first and second aliquots can be admixed with their respective solid phase supports in any order or substantially simultaneously.

After separating the solid and liquid phases that result from the above admixing and maintaining steps, the first solid support and any solid phase-bound anti-EBNA antibodies present in its immunoreactant are admixed in an aqueous liquid medium with labeled anti-human IgG antibodies. That admixture is maintained for a period of time sufficient for the anti-IgG antibodies to immunoreact with any solid phase-bound human IgG antibodies present. The second solid support and any solid phase-bound antibodies present are similarly admixed and maintained with labeled anti-human IgM antibodies.

Thereafter, the relative amounts of labeled anti-IgG and anti-IgM antibodies are determined. As noted hereinafter in relation to Tables 6–10, the presence of a relatively greater amount of labeled anti-IgM than anti-IgG indicates that the patient is in the acute state of EBV-IM infection, whereas a relatively greater amount of labeled anti-IgG present than anti-IgM indicates that the patient is in a convalescent state of the disease. About equal amounts of anti-IgM and anti-IgG indicate that the patient is passing from the acute to the convalescent state.

Another embodiment of this invention comprises a diagnostic system in kit form that includes a solid support comprised of a solid matrix such as a polystyrene twelve-well microtiter strip or double-welled "spoon", and a EBV- or CMV-homologous polypeptide of this invention, absorbed (bound) or otherwise affixed to the solid matrix to form a solid matrix. This system preferably also includes separately packaged anti-human Ig antibodies having a linked indicating means such as peroxidase-labeled goat anti-human Ig antibodies, and may also include substrate for the linked indicating means such as hydrogen peroxide and a color forming dye precursor such as o-phenylenediamine, in further, separate packages. Those anti-human Ig antibodies can be antibodies that immunoreact specifically with human only IgM, IgG, IgA or IgE or with all human antibodies, as noted previously. Stabilized hydrogen peroxide can also be included in the kit, or can be supplied by the end user. Buffer salts useful in an assay utilizing this system can also be included in one or more separate packages in dry or liquid form. Separate packages containing human anti-EBNA antibodies and human antibodies free from anti-EBNA antibodies (normal human antibodies) may also be included as positive and negative controls, respectively. Amounts of the above-mentioned ingredients sufficient for carrying out at least one assay are included in the kit, and an assay for the presence of anti-EBNA antibodies in a body sample such as serum may be carried out with this diagnostic system using the above-described method.

(b) Assay for EBV-IM

An exemplary ELISA, similar to that described before and described in detail in the Materials and Methods section (III) hereinafter, was used to screen for the presence of anti-polypeptide immunoglobulin in the sera of 91 people with anti-EBNA positive serotypes established using the anti-complement immunofluorescence (ACIF) described hereinbefore. When the sera were assayed at a 1:20 dilution, all 91 were positive against (bound to) polypeptides P27, P62, P60 and F16, F14 and F15. Even at the higher dilution of 1:320, 83 of the 91 EBNA positive sera immunoreacted with polypeptide P62 in the ELISA. Thus, there appears to be an excellent correlation between the anti-EBNA antibody titer established by ACIF and the antipeptide activity of each serum.

In addition, the results illustrate an excellent correlation between the ACIF method and the present ELISA technique, which is simpler and easier to use. Still further, the results illustrate the usefulness of polypeptides of this invention for a diagnostic assay for anti-EBNA antibodies.

Table 5, below, shows the reactivities of sera obtained from two subjects (SB and MV) before and after contracting EBV-induced infectious mononucleosis (IM; i.e., EBV-IM). In both cases antibodies that bind to polypeptides P27, P62 and P60 were absent before infection, but appeared afterward. In contrast, no antibodies were produced by either of these individuals that bound to polypeptide P89.

In further study, stored sera from a previously reported panel of 27 EBV non-immune donors [Catalano et. al., J. Clin. Invest., 65:1238-1245 (1980)] were screened for binding to polypeptides P62 and P60 in the before-described ELISA. The EBV-immune status of the sera used was defined by the presence or absence of Epstein-Barr viral capsid antigen (VCA). Individuals who have no serum antibodies to VCA (VCA) have never been infected with EBV. VCA positive (VCA+) individuals have had EBV infections and typically carry a low level of anti-EBNA antibodies. None of the sera displayed significant reactivity to either polypeptide as is seen from Table 5, below.

TABLE 5

ANTIBODIES TO EBNA PEPTIDES IN HUMAN SERA[1]

| PATIENT | $OD_{405} \times 10^3$ obtained[2] with Patient Antibodies to: | | | |
|---|---|---|---|---|
|  | P27 | P62 | P60 | P89 |
| VCA+ Normal 1[3] | 155 | 958 | 154 | 23 |
| VCA+ Normal 2[3] | 516 | 819 | 145 | 16 |
| SB pre-mononucleosis | 11 | 13 | 51 | 9 |
| SB post-mononucleosis | 33 | 514 | 115 | 23 |
| MV pre-mononucleosis | 15 | 77 | 72 | 29 |
| MV post-mononucleosis | 107 | 631 | 162 | 25 |
| VCA− Normals (n = 27) | 67 ± 23[5] | ND[6] | 45 ± 18 | ND |

[1]All sera were tested at a dilution of 1:20.
[2]Optical density measured at 405 nanometer light wavelength after 30 minute substrate incubations.
[3]VCA+ sera from individuals showing no clinical signs of present EBV related disease.
[4]Sera from 27 individuals showing no clinical signs of EBV related disease, past or present, as indicated by the absence of antibodies to VCA.
[5]Average optical density ± one standard deviation.
[6]Not done.

To examine the correlation between the ELISA and the ACIF diagnostic technique through the course of infection, stored sera from 8 college-age students, collected sequentially after onset of infectious mononucleosis (IM), were examined in the before-described ELISA using polypeptide P62. All students developed anti-EBNA titers from 1 month to 1 year following infection as measured by the classical method; i.e., ACIF. Henle, et. al., J. Infect. Dis., 130:231-239 (1974).

In one-half of the subjects, anti-P62 antibodies rose in parallel with the corresponding anti-EBNA titer as is shown for patient 15 in FIG. 4. In the other half, antibodies against polypeptide P62 were detected in the first month after the onset of symptoms, whereas those antibodies were detected at later times using the ACIF technique. These results are shown for patients 14 and 2 in FIG. 5. Anti-P62 antibodies were therefore detectable using the ELISA of the present invention before anti-EBNA antibodies were detectable by the standard anti-complement immunofluorescence assay.

To differentiate the class of immunoglobulin predominantly responsible for an individual's immune response at a given time during the course of infectious mononucleosis, secondary (indicating) antibodies specific for human IgG or IgM were used in the ELISA as described in the Methods and Materials section (III). Table 6, below, shows the results of this study with the sera of two individuals from different points in time during EBV infection measured against polypeptide P62 in the ELISA.

TABLE 6

POLYPEPTIDE P62-BOUND ELISA-DETECTED APPEARANCE OF ANTIPEPTIDE ACTIVITY AFTER MONONUCLEOSIS INFECTION

| Time After Infection | Patient MV | | Patient 15 | |
|---|---|---|---|---|
|  | IgM[1] | IgG[2] | IgM[1] | IgG[2] |
| Pre Infection | 103[3] | 74 | ND[4] | ND |
| 1 Week | 245 | 80 | 152 | 113 |
| 1 Month | 87 | 37 | 225 | 118 |

TABLE 6-continued

POLYPEPTIDE P62-BOUND ELISA-DETECTED
APPEARANCE OF ANTIPEPTIDE ACTIVITY
AFTER MONONUCLEOSIS INFECTION

| Time After Infection | Patient MV | | Patient 15 | |
|---|---|---|---|---|
| | IgM[1] | IgG[2] | IgM[1] | IgG[2] |
| 3 Months | 136 | 60 | 208 | 118 |
| 12 Months | ND | ND | 249 | 375 |
| 21 Months | 145 | 600 | 185 | 994 |

[1]Patient IgM level detected using a second antibody specific for human IgM.
[2]Patient IgG level detected using a second antibody, specific for human IgG.
[3]Optical density measured at 405 nanometer light wavelength.
[4]Not done.

Using this ELISA method, the rise in IgM antibody values, although small, are repeatable and found in all sequential sera tested. The immune response measured by the ELISA assay is normal in that IgM classically appears before IgG during EBV infection. The appearance of IgM antibodies prior to IgG antibodies is particularly well shown for patient 15 in Table 6. The above results again show that infection with EBV causes the production of antibodies that react with at least one polypeptide of this invention.

In a larger anti-polypeptide ELISA study, the panel of 19 VCA⁻ sera described hereinbefore were screened against polypeptides P27, P62, P60, F12, F13, F14, F15 and F16. None of the VCA⁻ sera were found to react positively. Typical data are shown in Table 7, below. Sera from clinically normal individuals positive for VCA antibodies were tested at two dilutions. Typical results, shown in Table 7 below, indicate that all of the VCA⁺ individuals were positive for, i.e., had antibodies that bound to, each of the polypeptides.

The sera of a number of rheumatoid arthritis (RA) patients were also screened in the ELISA. These results are also summarized in Table 7.

TABLE 7

ELISA-DETERMINED
AVERAGE ANTIPEPTIDE LEVELS IN HUMAN SERA

| Patient Group | Number of Sera | Average Antibody Activity of Polypeptides[1] | | | | | |
|---|---|---|---|---|---|---|---|
| | | P27 | P62 | P60 | F12 | F13 | F16 |
| Nor⁻[2] | 1/20[3] | 19 | 22 | 17 | 77 | 34 | 41 | 47 |
| Nor⁺[4] | 1/20[3] | 26 | 521 | 854 | 394 | 128 | 70 | 733 |
| Nor⁺[4] | 1/320[3] | 48 | 90 | 223 | 70 | 37 | 37 | 166 |
| A⁺[5] | 1/20[3] | 28 | 597 | 999 | 564 | 118 | 113 | 843 |
| RA⁺[5] | 1/320[3] | 48 | 126 | 348 | 122 | 50 | 50 | 231 |

[1]Activity measured as optical density at 405 nanometers light wavelength after 30 minutes of serum incubation.
[2]VCA negative individuals.
[3]Dilution at which sera were tested.
[4]VCA positive individuals.
[5]Individuals diagnosed as having rheumatoid arthritis.

The difference between the normal, VCA positive (control) and RA patients can best be seen at the serum dilution 1:320. The antibody levels in RA patients were significantly higher for every polypeptide tested at this dilution when analyzed using the Wilcox Rank Sum method (significance level greater than 99%).

Patients with Sjogren's Syndrome, Systemic Lupus Erythematosus (SLE) and Progressive Systemic Sclerosis (PSS) were also screened at both high and low serum dilutions. The only differences found between these patient groups and normals was a relatively higher average titer of the PSS patients to polypeptides P27, P62, P60, F16, F14 and F15. These results are believed to possibly be due to a previous EBV related infection or the involvement of EBV in those autoimmune diseases. These data do not detract from the usefulness of the ELISA as a diagnostic method.

The relative amounts of IgM and IgG antibodies can thus be utilized to determine the relative stage of the disease in an individual. In view of the (1) before-illustrated phased response of IgM anti-EBNA antibody production that builds and then falls, that is overlapped and followed in time by the buildup of IgG anti-EBNA antibody production, and (2) the fact that that phased response follows the normal occurrence levels of IgM in an early stage of a disease followed by IgG in the recovery stage.

Thus, the data of Table 6 show that during the early, acute stage of the disease there is a greater amount of anti-EBNA IgM antibody present than anti-EBNA IgG antibody. The level of IgG thereafter begins to climb during recovery, while the level of IgM falls, with the levels of both crossing; i.e., the ratio of IgG to IgM being one at some point in time between the acute and recovery (convalescent) stages.

Those findings are consistent with the usual findings for primary immunizations and disease states generally [See, for example, Hood et al., *Immunology*, The Benjamin/Cummings Publishing Co., Inc., Menlo Park, Calif., (1978) pages 39–46; Mims and White, *Viral Pathogenesis and Immunology*, Blackwell Scientific Publications, Boston (1984) pages 105–106, and *Immunology*, second ed., Bach ed., John Wiley & Sons, New York (1982), pages 337–339]. Those findings are contrary to the situation for anti-VCA IgM and IgG antibodies, wherein those IgG antibodies are present in greater amounts early in the infection, e.g., after two days, with the IgM antibodies rising, peaking and falling at lesser levels over a period of about three months, disappearing several months after acute illness [Cecil, *Textbook of Medicine*, Beeson et al., eds., W. B. Saunders Co., Philadelphia, (1979), pages264–268].

Those findings are also in some respects contrary to the findings of Henle et al., *J, Infect. Dis.*, 130:231–239 (1974). Those workers reported the appearance of low titer anti-EBNA antibodies about 2–4 weeks post onset of disease for a few sera, with low, but relatively higher titers appearing from the second month post onset through the end of their study at 12 months past onset for more and more of the sera as the time from onset increase. The techniques used by those authors were relatively insensitive and probably only measured IgG antibodies. Thus, the detectable appearance of antibodies during the recovery stage could be expected. More recently, Adniman et al., Chapter 33 in *Concepts in Viral Pathogenesis II*, Notkins and Oldstone eds., Springer-Verlag, New York (1986) page 326, reported, without identifying the antibody class, that anti-EBNA antibodies usually begin to appear one to two months after infection.

The results shown in Table 6 have been augmented to further show the efficacy of comparing the relative amounts of IgG and IgM anti-EBNA antibodies to provide a diagnostic for the stage of the EBV-IM; i.e., acute or recovery, using a polypeptide of this invention as an antigen for those antibodies. Some of those results are shown in Smith et al., *J. Infect. Dis.*, 154:885–889 (1986, November), whose disclosures are incorporated by reference. Some exemplary data from that paper are shown below in Table 8.

TABLE 8

Serological Data From Patients With Acute Infectious Mononucleosis

| Days Post Onset | OD 490[1] IgG | OD 490[1] IgM | Ratio IgG/IgM |
|---|---|---|---|
| Patient 1[2] | | | |
| 1 | 0.011 | 0.189 | 0.058 |
| 29 | 0.023 | 0.527 | 0.043 |
| 95 | 0.162 | 0.329 | 0.492 |
| 184 | 0.552 | 0.245 | 2.253 |
| 373 | 0.858 | 0.152 | 5.644 |
| Patient 2[2] | | | |
| 17 | 0.125 | 0.682 | 0.183 |
| 28 | 0.167 | 0.674 | 0.247 |
| 68 | 0.112 | 0.459 | 0.244 |
| 194 | 0.233 | 0.596 | 0.390 |
| 404 | 0.674 | 0.665 | 1.013 |
| Patient 8[2] | | | |
| 8 | 0.319 | 1.046 | 0.305 |
| 38 | 0.165 | 0.696 | 0.237 |
| 109 | 0.141 | 0.603 | 0.234 |
| 404 | 1.304 | 0.562 | 2.320 |
| Patient 11[3] | | | |
| 2 | 0.005 | 0.055 | 0.091 |
| 23 | 0.016 | 0.702 | 0.023 |
| 372 | 0.878 | 0.643 | 1.365 |
| 1,519 | 1.079 | 0.199 | 5.422 |

[1]OD 490 optical density at 490 nanometers measured as discussed in the Materials and Methods Section III K.
[2]Sera from heterophil-negative donors.
[3]Serum from a heterophil-positive donor.

The results in Table 8 again illustrate the rise and fall over time of IgM anti-polypeptide antibodies, and whose IgM fall corresponds with the rise of IgG anti-polypeptide antibodies for patients that were both heterophil negative and positive at the beginning of the assay period. Antibodies (IgM and/or IgG) to the viral capsid antigen of EBV (VCA) were present in all but one of the serum samples examined for the total of 13 patients of the study.

Sera from one of the heterophil-negative patients and two of the three heterophil-positive patients had relatively higher IgG anti-EBNA polypeptide antibodies shortly after the onset of the disease. However, the ratio of IgG to IgM, although initially greater than one, increased with time course for each patient; and the serum samples showed a general lowering of the IgM anti-polypeptide antibody level coupled with a delayed, overlapping rise in IgG anti-peptide antibody level. Thus, in all of the patients' sera studied, an increasing ratio of IgG anti-polypeptide antibody to IgM anti-polypeptide antibody present heralded the recovery phase of the illness when maximum IgG responses were observed.

Serum samples were obtained from nineteen individuals who were either clinically diagnosed as having IM, or, when clinical data were unavailable, were determined to contain heterophil antibodies in their sera. Those samples were assayed using an ELISA assay of this invention in which polypeptide P62 was used as the solid phase-bound antigen. The IgG, IgM and IgA levels in those sera were determined, and the levels of anti-EBNA IgG and IgM were compared as a ratio. The IgA levels showed no discernable correlation. The results of that assay for IgG and IgM are shown in Table 9, below.

TABLE 9

Anti-EBNA Antibody Levels in Heterophil-Positive Sera

| Sample Number | OD 490[1] IgG | OD 490[1] IgM | Ratio IgG/IgM |
|---|---|---|---|
| 1 | 0.018 | 0.609 | 0.029 |
| 2[2] | 0.055 | 1.074 | 0.051 |
| 3 | 0.133 | 0.412 | 0.322 |
| 4 | 0.035 | 0.545 | 0.064 |
| 5 | 0.087 | 0.491 | 0.177 |
| 6[2] | 0.319 | 1.046 | 0.305 |
| 7 | 0.016 | 0.388 | 0.041 |
| 8 | 0.315 | 1.245 | 0.253 |
| 9 | 0.118 | 1.255 | 0.094 |
| 10 | 0.300 | 0.753 | 0.039 |
| 11[3] | 0.019 | 0.918 | 0.020 |
| 12 | 0.002 | 0.415 | 0.005 |
| 13 | 0.282 | 0.928 | 0.300 |
| 14 | 0.004 | 0.572 | 0.007 |
| 15 | 0.007 | 0.779 | 0.009 |
| 16 | 0.609 | 0.396 | 0.023 |
| 17 | 0.005 | 0.446 | 0.011 |
| 18 | 0.002 | 0.404 | 0.005 |
| 19 | 0.002 | 0.730 | 0.003 |

[1]OD 490 = optical density at 490 nanometers measured as discussed in the Materials and Methods Section III K.
[2]Sera had relatively elevated IgA levels; i.e., greater than an OD 490 of 0.300.

The data in Table 9 again show that sera from patients with the active, acute disease contained relatively elevated levels of IgM anti-EBNA antibodies that bound to the polypeptide antigen as compared to levels of IgG. Those data also show enhanced levels of anti-EBNA antibodies as compared to sera from VCA⁻ patients as shown in Table 5. The presence of negligible levels of IgG anti-polypeptide antibodies is consistent with the observations of Henle et al., J. Infect. Dis., 130:231–239 (1974).

Sera from approximately 10 percent of acute EBV-induced cases of IM lack the heterophil antibody, as determined by conventional serology. Since the heterophil antibody and anti-EBNA antibodies should be unrelated, a number of additional sera from heterophil-negative IM patients were analyzed in the assay used in Table 9. The results are shown in Table 10, below. These patients were either confirmed clinically or by conventional EBV serology to have acute IM. Each serum had positive VCA-IgM and EBV early antigen-diffuse (EA-D) titers, which in conjunction with negative EBNA titers (by ACIF), are usually considered hallmarks for acute IM, irrespective of the presence of heterophil antibody.

TABLE 10

Anti-Polypeptide EBNA Levels In Heterophil-Negative Sera From Patients With Acute Disease

| Serum Number[2] | OD 490 IgG | OD 490 IgM | Ratio IgG/IgM |
|---|---|---|---|
| 1 | 0.706 | 1.449 | 0.49 |
| 2 | 0.836 | 1.232 | 0.68 |
| 3 | 0.182 | 0.713 | 0.255 |
| 4 | 0.013 | 0.694 | 0.018 |
| 5 | 0.351 | 0.736 | 0.476 |
| 6 | 0.033 | 0.841 | 0.039 |
| 7 | 0.029 | 0.758 | 0.038 |
| 8 | 0.011 | 0.456 | 0.024 |

TABLE 10-continued

Anti-Polypeptide EBNA Levels
In Heterophil-Negative Sera
From Patients With Acute Disease

| Serum | OD 490 | | Ratio |
|---|---|---|---|
| Number[2] | IgG | IgM | IgG/IgM |
| 9 | 0.014 | 0.538 | 0.026 |
| 10 | 0.163 | 0.757 | 0.215 |

[1]See Note 1 of Table 8.
[2]Each serum sample was assayed and found positive for VCA-IgM and EA-D, and negative for EBNA antibodies by ACIF.

In all cases shown, the ratio of IgG to IgM in the anti-EBNA polypeptide ELISA was less than 1.0 and also less than 0.7. It is apparent from these data that the anti-EBNA polypeptide P62 ELISA is capable of detecting IM in heterophil-negative individuals when the IgG/IgM anti-polypeptide ratio discriminator is applied to the ELISA data.

A further illustration of the uncoupling of the presence of heterophil antibodies and IgM anti-polypeptide antibodies, and the early detection of anti-polypeptides afforded by an assay of the present invention is shown by the data of Table 11, below. These data also complement the data shown in FIG. 5 regarding the early detection of these antibodies using an assay of the present invention compared to ACIF.

Here, eight sets of paired sera were assayed by a conventional commercial assay for heterophil antibodies and by the anti-polypeptide P62 ELISA. In each case, the first serum draw was negative by the former test, while positive by the latter. The individuals showed symptoms of IM at the time of that first bleed. Hence, in these individuals, IgM anti-polypeptide P62 antibodies appeared in sera in advance of the heterophil antibodies, as ascertained by conventional serology. In the first two cases in the Table, the times between the bleed dates were 14 and 8 days, respectively.

TABLE 11

Anti-Polypeptide P62 Antibodies Are
Detected Prior To Heterophil
Antibodies In Acute IM

| Patient | OD 490 | | Ratio | Hetero- |
|---|---|---|---|---|
| Number[2] | IgG | IgM | IgG/IgM | phil[3] |
| 1 | 0.122 | 0.489 | 0.25 | − |
|  | 0.399 | 0.940 | 0.42 | + |
| 2 | 0.064 | 0.512 | 0.125 | − |
|  | 0.749 | 1.10 | 0.68 | + |
| 3 | 0.013 | 0.364 | 0.036 | − |
|  | 0.04 | 0.592 | 0.068 | + |
| 4 | 0.009 | 0.597 | 0.015 | − |
|  | 0.038 | 0.696 | 0.055 | + |
| 5 | 0.007 | 0.472 | 0.015 | − |
|  | 0.079 | 0.624 | 0.13 | + |
| 6 | 0.014 | 0.363 | 0.04 | − |
|  | 0.086 | 0.937 | 0.09 | + |
| 7 | 0.009 | 0.447 | 0.02 | − |
|  | 0.021 | 0.584 | 0.04 | + |
| 8 | 0.023 | 0.466 | 0.05 | − |
|  | 0.951 | 0.50 | 1.9 | + |

[1]See Note 1 of Table 8.
[2]The first serum draw was obtained at presentation of symptoms of acute IM. The second draw was obtained from the same individual a short time later. Acute IM was confirmed in each case by the ultimate presence of heterophil antibodies.
[3]The presence of heterophil antibodies was determined by use of a commercial kit.

The before-described ratio assays, while having a qualitative aspect in that the presence of anti-P62 antibodies is determined, are primarily utilized quantitatively to ascertain relative amounts of anti-P62 IgM and IgG antibodies were present in the human body sample. That primarily quantitative assay normally requires about 2.5 hours to perform after the solid phase supports are prepared.

A more qualitative ratio that requires slightly more than about six minutes to perform, after preparation of the solid phase support, has also been developed. This assay utilizes similar methodology and chemistry to the assays described before, but relies upon a visual comparison of color intensities produced by a previously discussed indicating means and substrate to assess the relative amounts of anti-peptide P62 IgG and IgM antibodies present in the assayed sample, and thus whether the state of the disease is acute, convalescent or passing from acute to convalescent.

In preferred embodiments, the solid phase support is comprised of a white opaque polystyrene "spoon" matrix. The solid phase "spoon" matrix is constructed to contain two adjacent wells to which polypeptide P62 is affixed. The wells are separated by a raised dam that acts to prohibit liquid from one well entering the other.

Assays for anti-IgM and anti-IgG antibodies are separately carried out as generally described before, but are here preferably carried out side by side (one analysis for each of the antibody types in each well) and substantially simultaneously. In addition, rather than determining optical density values or other labeling indicia mechanically, the user merely compares the color intensities of each well by eye.

This assay, while requiring less than about one-tenth the time of the previously described assay, exhibits an extremely high specificity and sensitivity. In addition, it is readily adapted for use in a physician's office so that doctor and patient can know the results of the assay while the patient is in the office.

Further details of this assay are provided in the Materials and Methods section III D.

(c) Assays for EBV-IM and CMV-IM

The Epstein-Barr nuclear antigen contains a unique sequence of over 200 amino acids that contain only the amino acids glycine and alanine. Peptides made from these sequences are immunoreactive with sera from VCA positive individuals, as shown before. Furthermore, a peptide from this sequence, P62, is the most immunoreactive with sera from patients with acute EBV infectious [Rhodes et al., in *Herpesvirus*, R. Rapp ed. Alan R. Liss, New York p. 487–496 (1984); Rhodes et al., *J Immunology*, 134:211–216 (1985); Smith et al., *J Infect Dis.* 154:885–889 (1986); Geltosky et al., *J. Clin Lab Analysis* 1:153:162 (1987)]. Patients with acute EBV-IM have IgM antibodies to EBNA proteins in several EBV positive cell lines [Geltosky et al., *J. Clin Lab Analysis* 1:153:162 (1987); Rhodes et al., *J Exp Med* 165:1026–1040] detected by immunoblotting.

The results discussed hereinafter illustrate that sequential sera not only from EBV-IM but also from cytomegalovirus (CMV)-induced mononucleosis-like illnesses (CMV-IM) have IgM antibodies directed to the EBNA P62 epitopes in the acute phase of the illness. Sequential serum samples taken from eight patients with acute CMV infection all show a sharp rise of IgM anti-P62 antibodies during the acute illness. This same response is seen both in patients with a past EBV infection as well as one individual who was infected with CMV before EBV. Immunoblotting of the serum from both acute EBV- and acute CMV-infected IM patients showed that the same set of IgM antibodies is induced by both viruses and that the antibodies react with a number of normal cellular proteins present in uninfected cells. Thus, the presence of these IgM antibodies is diagnostic of acute infection with either EBV or CMV.

(i) Sequential Sera From A Patient With EBV-IM Have IgM Antibodies To P62 And EBNA-1 In The Acute Illness Phase IgM antibodies that recognize peptide EBNA P62 are detected in an ELISA assay during the acute phase of EBV-IM [Rhodes et al., in *Herpesvirus*, R. Rapp ed., Alan R. Liss, New York; p. 487–496 (1984); Rhodes et al., *J. Immunology*, 134:211–216 (1985); Smith et al., *J. Infect Dis.*, 154:885–889 (1986); and Geltosky et al., *J. Clin. Lab Analysis*, 1:153–162 (1987)]. These observations were confirmed when sequential sera from D.B., a patient with EBV-IM, were analyzed for immunoreactivity by the EBNA P62 ELISA (FIG. 6).

These data demonstrate an early rise of IgM antibodies in the acute phase of the illness (Jan-March 1985) that corresponds to the early rise of VCA IgM and IgG antibodies (1:2) without anti-EBNA by the traditional IFA method. Sera from this patient had a slow rise of IgG antibodies to P62 that peaked in the March-April 1985 specimens after the acute phase of the illness. The IgG/IgM ratio exceeded 0.7 in the May 1985 specimen when the patient was in the late convalescent phase of the illness. At this time, anti-EBNA titers were evolving and VCA-IgM titers were barely detectable by conventional EBV serology.

The dramatic rise of IgM class-specific antibodies during the acute phase of illness were confirmed by the immunoblotting technique (FIG. 7). The same serum samples used for the ELISA were used in immunoblotting studies to detect antigens present in an EBV-transformed B cell line.

As can be seen from FIG. 7, the IgM antibodies present in the patient serum recognize a series of 8 major and more minor bands in the extract. The IgM antibodies to most of these proteins rise in the first two serum samples, peak at the third sample, and decline thereafter. This is the same temporal sequence that is observed in the peptide ELISA.

The proteins recognized by the IgM antibodies include EBNA-1 at 77 kD as well as a series of normal cellular proteins (bands at 92, 82, 80, 69, 62 and 58 kD) that contain epitopes related to the glycine-alanine region of EBNA-1 [Rhodes et al., *J. Exp. Med.*, 165:1026–1040 (1987)]. Antibodies to the proteins at 120 and 29 kD, which have no sequences in common with EBNA-1 [Rhodes et al., *J. Exp. Med.*, 165:1026–1040 (1987)], seem to peak earlier. Thus, there is a good correlation between the IgM antibodies to the synthetic peptide P62 and the majority of IgM antibodies detected by Western blotting.

The IgG antibodies to EBNA-1 (77 kD) in patient D.B. appeared late on the immunoblots (FIG. 7), an observation consistent with the EBNA P62 ELISA data. On the left side of the blot in FIG. 7, the strong IgG response to the 77 kD EBNA band from a VCA positive (VCA+), EBNA-1 positive (EBNA-1$^+$) individual is shown as a control. IgG anti-EBNA-1 antibodies were first detected in the blots at 51 days after onset of the disease (fourth time point), the same time that IgG antibodies to the peptide started to rise.

(ii) Sequential Sera From A Patient with CMV-IM who Subsequently Developed EBV-IM Sequential serum samples from patient D.S. were also analyzed by EBNA P62 ELISA and Western blotting. The clinical/serological data on this patient have been published, and by classic serology it was shown that he had an acute CMV infection followed three months later by an acute EBV illness.

The results of the anti-peptide ELISA studies using sequentially-taken sera from patient D.S. are shown in FIG. 8. Sera from patient D.S. in the acute CMV phase of the illness had a pronounced IgM response to the P62 peptide detected by ELISA, just as patient D.B. had during his acute EBV infection. The IgM anti-peptide signal was high for the three serum samples obtained during the first illness and was also elevated in the initial sample of the second illness. It is not known if the antibody level decreased between the two diseases. The IgG antibodies to polypeptide P62 were not detected until the last serum sample obtained one year after the second illness.

Samples from this patient were also analyzed by immunoblotting (FIG. 9). IgM antibodies to proteins of molecular weights 82, 80-77, 69, 62 and 58 kD were found during both infections. It should be noted that the IgM antibodies recognize the same antigens during both diseases. The IgM antibody levels measured in the blots were at their highest levels during the first and the initial part of the second infection and declined thereafter, a finding similar to that seen in the anti-peptide P62 ELISA. IgG antibody to EBNA-1 appeared only at the last time point (weak band next to a normal VCA$^+$ EBNA-1$^+$ control in the right lane)

Both patients showed an early IgM anti-peptide P62 response that correlated with IgM antibodies to a number of bands seen in the Western blots. The IgG anti-peptide P62 response occurred much later and was correlated with the appearance of IgG antibodies that are specific for the EBNA-1 protein. This is consistent with what has been previously reported [Rhodes et al., in *Herpesvirus*, R. Rapp ed., Alan R. Liss, New York, p. 487–496 (1984); Rhodes et al., *J. Immunology*, 134:211–216 (1985); Smith et al., *J. Infect Dis.*, 154:885–889 (1986); Geltosky et al., *J. Clin. Lab Analysis*, 1:153–162; and Rhodes et al., *J. Exp. Med.*, 165:1026–1040 (1987)].

The surprising finding is that CMV infection induces IgM antibodies with these same properties. That is, IgM antibodies that appear during CMV infections react with a series of antigens of apparently identical size to those which occur during EBV infection.

(iii) Sera From Ten Patients With Acute CMV-IM

Sera from ten patients with CMV-IM were studied in the ELISA and by immunoblots to determine if the IgM antibodies detected in the sera of patient D.S. to EBNA p62 and those of the immunoblots were unique to this patient or if this response could be detected in sera from other patients with CMV-IM. All of these patients had had a previous EBV infection as indicated by positive IgG VCA titers and positive EBNA-1 titers by IFA.

Representative anti-peptide P62 data from two of these patients are shown in FIGS. 10 A and 10 B. All 10 patients showed a pronounced increase in IgM anti-peptide P62 antibodies during the acute phase of the CMV disease. The IgM antibodies persisted for one to two months, and then returned to background levels.

In contrast, IgG anti-peptide P62 antibodies started at a positive value (since the patients were EBV$^+$, VCA$^+$, EBNA-1$^+$), and showed little change during the course of the disease. In fact, out of seven patients with sequential serum samples, four showed slight increases in the IgG anti-peptide P62 antibody levels (e.g., FIG. 10 B), 1 showed a decrease (FIG. 10A), and two showed no change.

The same sera were also analyzed by immunoblotting. All of the patients showed a transient rise of IgM antibodies to a number of antigens during the acute phase of the disease similar to those seen in FIGS. 7 and 9. Little, if any, change could be detected in the IgG anti-EBNA-1 antibody levels.

Thus, all of the patients examined with acute CMV infections showed a pronounced transient increase in IgM anti-peptide P62 antibodies with a smaller and variable change in the igG anti-peptide level.

The ratio of IgG to IgM is a convenient way to express the anti-peptide P62 data from EBV-IM patients. As illustrated previously, this ratio is less than 1 during the acute phase of the illness and increases during convalescence to a value greater than 1 where it remains for the remainder of the individual's life [Rhodes et al., *J. Exp. Med.*, 165:1026–1040 (1987)]. The advantage of this ratio method of analysis is that it avoids having to define background and cutoff values [Geltosky et al., *J. Clin Lab Analysis*, 1:153–162 (1987) ].

When analyzed by the ratio method, this study revealed two general types of immune responses to the polypeptide P62 epitope. For example, sera from patient L.S. (FIG. 10A) demonstrated the predominant response. Here, a ratio of nearly 2 in the pre-illness samples was observed. This ratio fell below 1 (to 0.661) during the acute illness then rose again during convalescence. A total of eight of ten patients with an acute CMV-IM infection scored positive in the EBNA P62 ELISA by the ratio analysis.

Patients S.G. and G.S. presented another type of response to P62. Although both exhibited an increase in IgM antibodies during the acute illness, the maximum value remained below the IgG levels. These sera are scored negative by the ratio analysis. In both cases, the false negative result was due to large initial IgG signal. Thus, although a prior CMV infection is relatively rare in the age group of individuals that contract EBV-IM, some false negative results may occur using the IgG/IgM ratio method.

(iv) Direct Comparison Of The Antigens Recognized By EBV IM And CMV IM Sera

A very similar pattern of antigens is recognized by IgM antibodies during acute EBV and CMV infections (compare FIGS. 7 and 9). In order to directly compare these antigens, sera from patients with either disease were immunoblotted side by side with the same cell extract. The cells used for the extract were the K562 cell line. It is important to note that these cells contain no EBV or CMV sequences. Thus, any antigens detected are normal cellular proteins.

Figure 11A:
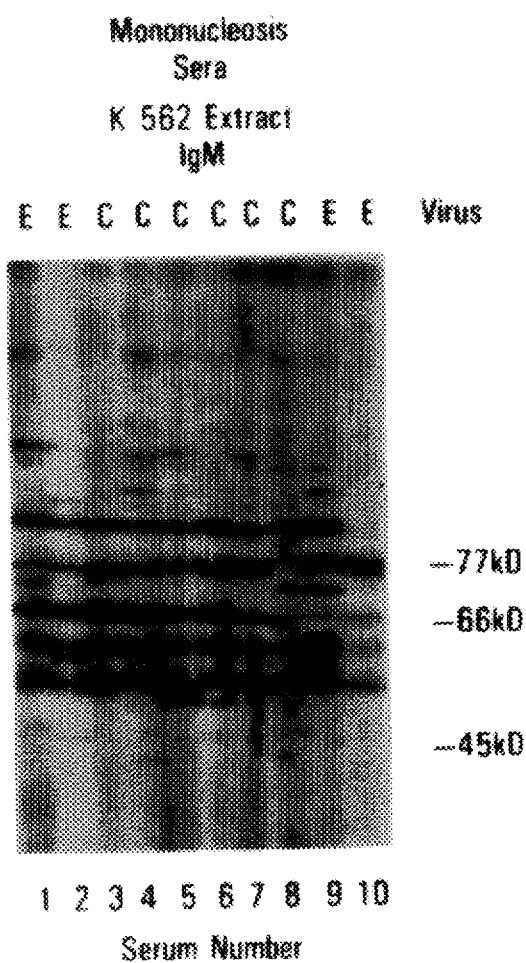
Figure 11B:
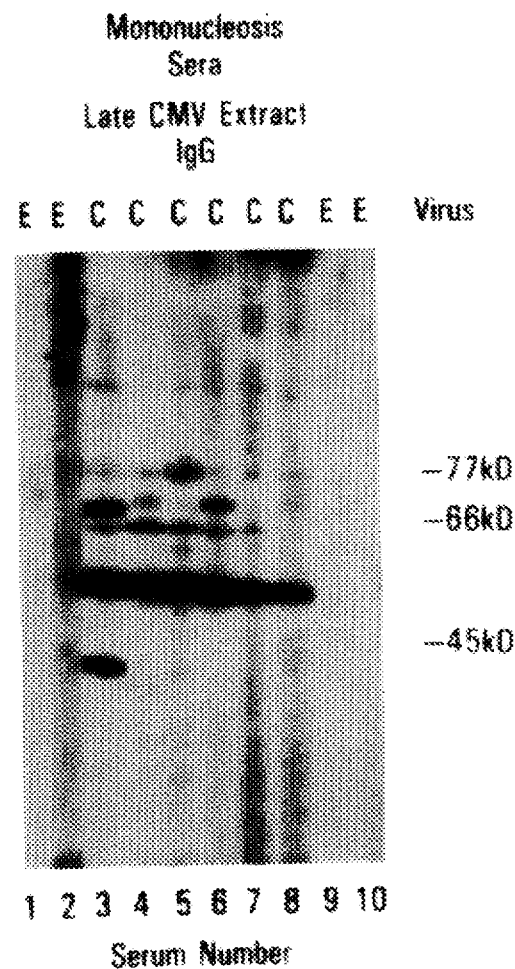

The data from this study related to binding by IgM antibodies are shown in FIG. 11A. Lanes 1, 2, 9 and 10 were probed with sera from EBV-IM patients, whereas the remaining lanes were probed with sera from patients with acute CMV-IM infections.

As can be seen from that Figure, the major antigen bands at 92, 82–77, 69, 62 and 58 kD have identical reactivities with the sera of patients infected with either virus. Some less intense bands were also seen in both patient groups. There was a band around 50 kD that seems to be found in only the CMV patients, but this is an exception. All other bands were either found in one or few sera or are common to all sera. Thus, infection by either virus induced IgM autoantibodies to the same set of proteins.

The same set of sera were also blotted using an extract of CMV-infected fibroblasts. IgG antibody was detected in the studies shown in FIG. 11B.

In that Figure, it can be seen that all CMV patients had IgG antibodies to a prominent antigen of 50 kD, another at 64 kD, and others that were present in only a few of the CMV patients. Little, if any reaction was seen in the EBV infected patients. Work in progress indicates that all of the bands seen in this study are due to virally encoded CMV proteins.

It is concluded that acute infection by CMV or EBV induces a common set of IgM autoantibodies. In contrast, the IgG antibodies are specific for proteins from the virus that cause the disease and those IgG antibodies have no reactivity with host components [Rhodes et al., *J. Exp. Med.*, 165:1026–1040 (1987)].

(v) Inhibition Of Antibody Binding With Peptide P62

Peptide P62 has previously been shown to inhibit antibody binding to a number of IgM antibodies induced by EBV [Rhodes et al., *J. Exp. Med.*, 165:1026"1040 (1987)]. This is again demonstrated in FIG. 12 where two EBV$^+$ sera were blotted on an extract of EBV$^+$ B cells.

In FIG. 12, lane 1 contained serum from patient D.B. 15 days post onset of disease and lane 5 contained another acute EBV-IM serum. Lanes 2 and 6 had the respective sera further containing 400 ug/ml of peptide P62. These studies were done at a higher serum dilutions than those shown in FIG. 7 so that only the most strongly reactive bands would be easily visible.

As can be seen from FIG. 12, the polypeptide inhibited IgM antibody binding to several protein bands, the easiest to see are the bands at 82 to 77 kD. Work in progress indicates that this area contains EBNA-1 and one or more cellular proteins.

Lane 3 contained serum from patient D.S. 12 days after the onset of his CMV illness, whereas lane 4 was the same serum plus peptide P62, as before. Again, IgM reactivities with the 82-77 kD bands as well as some in the range 58 to 62 kD were inhibited by the EBV peptide.

Inhibition studies of the IgG antibodies seen in blotting experiments were also performed. Lane 7 contained serum from patient D.B. 514 days after disease onset, lane 9 contained serum from patient D.S. 417 days after onset of his CMV illness, and lane 11 was from a normal adult with a long past EBV infection. Lanes 8, 10 and 12 contained the respective sera with 50 ug/ml of P62.

The only protein detected was the EBNA-1 band at 77 kD. Binding to this protein was inhibited by the peptide in all cases.

It is concluded from these studies that CMV infection produces IgM autoantibodies that recognize a peptide from the EBNA-1 region of EBV. These IgM antibodies recognize a series of cellular autoantigens that are identical in mobility and share an epitope specificity with those produced during EBV infection.

(d) Assay for Nasopharyngeal Carcinoma (NPC)

As noted earlier, EBV has been implicated as the causative agent of nasopharyngeal carcinoma (NPC). Nasopharyngeal carcinoma is a major form of cancer in China, with an incidence rate as high as 100 per 100,000 persons per year.

Western blot analyses using EBV-infected Wi-L2 cell extracts with sera from a normal VCA$^+$ person, a patient with IM and six patients with NPC showed an immunoreaction with the EBNA protein, IgM and IgG responses to the EBNA protein with the serum from the IM patient, and IgG, IgM and IgA reactions to the EBNA protein from the NPC patients.

Recent studies have shown that serum levels of IgG and IgA antibodies to a variety of EBV antigens are significantly elevated in NPC patients. [Henle et al., *Int. J. Cancer*, 17:1–7 (1976). Desgranges et al., Int. *J. Cancer*, 19:627–633 (1977); and Pearson et al., *Cancer*, 51:260–268 (1983).] More specifically, Henle et al., reported high IgA serum titers to the VCA and D\(diffuse) antigens that occasionally matched the IgG titers to those antigens. Desgranges et al. utilized saliva and reported finding neutralizing IgA and IgG antibodies to VCA and EA (early antigen). Pearson et al. reported the diagnostic efficacy of an IgA anti-VCA assay coupled with an IgG anti-EA assay. Those studies did not report on the presence of IgA anti-EBNA antibodies in the samples they examined.

A number of sera from patients known to have NPC were assayed using a solid phase ELISA with polypeptide P62 affixed to a solid matrix to form a solid support as discussed previously. Those sera were also assayed by standard serological assays. The results are illustrated in Table 12, below.

TABLE 12

ELISA Values on Sera From NPC Patients

| Samples | Anti-EBV Titers[1] | | | Anti-P62 Titers[2] | | |
|---------|------|-----|-----|----------|-------|-------|
|         | VCA  | EA  | IgA | IgA      | IgM   | IgG   |
| 1  | 320  | 120 | 60  | 0.617(+) | 0.642 | 1.686 |
| 2  | 960  | 40  | 60  | 0.376(−) | 0.541 | 1.570 |
| 3  | 640  | 126 | 15  | 0.737(+) | 0.247 | 1.143 |
| 4  | 320  | NT  | 30  | 0.289(−) | 0.173 | 0.958 |
| 5  | 1920 | 320 | 240 | 0.871(+) | 0.303 | 2.000 |
| 6  | 960  | 80  | 80  | 0.738(+) | 0.334 | 0.915 |
| 7  | 640  | 320 | 10  | 0.675(+) | 0.216 | 0.993 |
| 8  | 960  | 640 | 320 | 0.667(+) | 0.478 | 1.160 |
| 9  | 480  | NT  | 15  | 0.701(+) | 0.417 | 1.324 |
| 10 | 640  | 60  | 20  | 0.024(−) | 0.159 | 0.207 |
| 11 | 1280 | 240 | 80  | 0.466(+) | 0.142 | 1.139 |
| 12 | 240  | 40  | 80  | 0.651(+) | 0.725 | 1.360 |
| 13 | 128 0 | | 120 | 160 | 0.421(+) | 0.190 | 1.566 |

NT = Not Tested
[1] Anti-EBV polypeptide P62 ELISA was carried out on these sera as described in the Materials and Methods Section. Plus signs (+) indicate optical density values considered positive for NPC, whereas minus signs indicate optical values considered negative for NPC.

As can be seen from the above data, the serological assays for VCA, EA and IgA correlated well with a relatively increased IgA anti-peptide P62 titer. The IgA anti-peptide P62 titer was not inhibited by the presence of IgM or IgG antibodies present in the serum. In addition, the IgM to IgG ratio can be seen to show that the patients did not have acute IM. Still further, anti-EBNA titers, as determined by ACIF, were found to be unrelated to disease.

In studying the sera of normal persons who do not have NPC, an O.D. $_{490}$ value of 0.3 was found as the control value for this IgA assay. In this particular assay format, an O.D. $_{490}$ value significantly above 0.3 was taken as a positive indicator of NPC. Thus, in the above Table, 10 of 13 sera were positive for NPC and are so indicated by a plus sign (+).

The previously discussed general assay method for detection of anti-EBNA antibodies is also seen to be effective in detecting the presence of NPC in a person. An antibody-containing body sample such as serum, plasma, saliva, sputum or a throat washing is used. The body sample is admixed with the solid phase support in an aqueous medium as previously described. Here, the amount of IgA antibodies is assayed, with a relatively increased amount above a control indicating the presence of NPC.

(e) Immunologic Crossreactivity of EBV and CMV Related Peptides

The herpes virus Human Bytomegalovirus (CMV) has been implicated as an important pathogen that may cause birth defects and opportunistic infection in immunosuppressed individuals. CMV virus also causes a "mononucleosis-like" illness (CMV-IM) similar to infectious mononucleosis caused by EBV (EBV-IM).

During clinical studies on the use of a polypeptide P62-base ELISA to detect the presence of anti-EBNA antibodies in patients with acute phase EBV-IM, it was noted that approximately 60–70% of the heterophile negative cases of CMV-IM scored positive in the P62-based ELISA. The presence of antibodies in the CMV-IM patients capable of immunoreacting with P62 was thought to be the result of either a reactivation of the latent EBV infection by the current CMV infection or the result of the production of an CMV protein that is immunologically crossreactive with EBNA.

To investigate the possibility that the serum of CMV infected individuals contained P62 crossreactive antibodies induced by a CMV-encoded antigen, three CMV-related polypeptides, shown in Table 13, were synthesized.

TABLE 13

| Peptide Designation | Amino Acid residue Sequence |
|---|---|
| C1 | AGGGGGGGAGGGGGGGGSGG |
| C2 | SSSSAGGGGGGGAGGGGGGGGSGG |
| C3 | SSSSAGGGGGGGAGGGGGGGGSGGC |

1. The amino acid residue sequence of peptides C1, C2 and C3 each corresponds to a portion of a polypeptide predicted to be expressed by a coding region of exon 1 of the 2.2 kilobase CMV RNA reported by Stapraus et al., J. Virol., 57:591–602 (1986).

Serum samples obtained over the course of IM from selected patients were assayed for IgG and IgM immunoreactivity to polypeptides P62, C1 and C2 using an ELISA similar to that described in Methods and Materials section IIID. FIG. 14 illustrates the results of this study using the serum samples obtained from a patient (DB) having an EBV infection resulting in the development of acute IM followed by the convalescent phase of the illness. Those results illustrate the before described pattern of detecting anti-P62 IgM antibodies during the acute phase of EBV-IM and the rise of anti-P62 IgG (and concomitant fall of anti-P62 IgM) antibodies during convalescence.

FIG. 14 also illustrates that when CMV-related peptides C1 and C2 were used as solid phase (target) antigen in the ELISA, the same sequential specimens obtained from patient DB were found to contain anti-C1 and anti-C2 IgM antibodies during the acute phase of the illness. However, while the IgM anti-C1 and anti-C2 antibody response fell off with the onset of convalescence, there was no concomitant rise in anti-C1 or anti-C2 IgG antibody detected.

Sequential serum samples from a second patient (DS) having a primary CMV infection resulting in acute CMV-IM followed by a secondary EBV infection resulting in Acute EBV-IM were assayed in the P62, C1 and C2 ELISAs as described above. As illustrated in FIG. 15, each of the ELISAs detected IgM anti-peptide antibodies during the acute phases of the CMV and EBV infections.

The immunologic activity of the CMV-related peptides was further examined by studying the ability of antibodies induced by C1, C2 and C3 to immunoreact with EBNA. Rabbit anti-peptide antisera to C1, C2 and C3 were each immunoreacted with extracts of cells expressing EBNA using an immunoblotting procedure similar to that described in Methods and Materials section IIIG. The results of the immunoblotting study indicate that anti-C1, anti-C2 and anti-C3 rabbit antibodies immunoreact with EBNA.

Furthermore, when the anti-C1 and anti-C2 rabbit antibodies were maintained with their respective peptides prior to immunoblotting, the immunoreaction with EBNA protein was blocked.

Therefore, it should be noted that while the amino acid residue sequences of polypeptides C1, C2 and C3 correspond to a sequence encoded by the CMV genome, those polypeptides are polypeptides of the present invention because they contain an amino acid residue sequence represented by the formula:

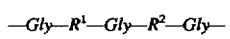

wherein $R^1$ and $R^2$ designate amino acid residues which taken individually are the same or different and are selected from the group consisting of Ala, Arg, Gly, Leu, Pro, Ser and Thr with the provision that the $R^1$ and $R^2$ are both not Gly. In addition, the above results indicate that polypeptides C1, C2 and C3 can immunoreact with IgM antibodies induced by EBNA and that antibodies induce by those peptides immunoreact with EBNA.

Both EBV and CMV produce a non-malignant lymphoproliferative disease whose acute phase is characterized by the product of IgM antibodies that immunoreact with a polypeptide of this invention. Because anti-EBNA antibodies are typically not found in association with malignant lymphoproliferative, the present invention therefore provides a diagnostic system and method for distinguishing between virally-induced, non-malignant and malignant lymphoproliferative disease.

3. Preparation For Passive Immunization

A patient with latently infected B lymphocytes that express EBNA on their cell surfaces can be treated with receptors of this invention, preferably as whole antibodies, raised to the synthetic polypeptides of the present invention that immunoreact with EBNA. The receptors are administered in a unit dose having an effective amount of receptors dispersed in a pharmaceutically acceptable diluent.

An effective amount of such antibodies varies depending on the reactivity and type of the antibodies. Generally, about 0.5 milligrams to about 25.0 milligrams of antibody per kilogram patient body weight is considered effective. The antibodies can be administered intravenously, intramuscularly, or intraperitoneally, with several administrations given at 3 to 20 day intervals. The antibodies can also be given in conjunction with surgical or chemical treatment.

The antibodies can be obtained from the sera or plasma of an animal species different from the patient to be treated by raising antibodies to the polypeptide of this invention using the before-described inocula. The antibodies can also be obtained from monoclonal sources such as ascites fluid by preparing a hybridoma cell line using techniques known in the art. Whole antibodies are preferred as the combining site since they are capable of activating the complement system when an immune complex is formed.

III. METHODS AND MATERIALS

A. Synthesis of Polypeptides

The polypeptides of this invention were chemically synthesized by solid-phase methods as described in Merrifield et. al., *J. Am. Chem. Soc.*, 85:2149–2154 (1963) and Houghten et. al., *Int. J. Pept. Prot. Res.* 16:311–320 (1980). The solid phase method of polypeptide synthesis was practiced utilizing a Beckman Model 990B Polypeptide Synthesizer, available commercially from Beckman Instrument Co., Berkeley, Calif., U.S.A.

For polypeptides having fewer than 35 residues that were used in inocula, a cysteine residue was added to the amino-terminus or to the carboxyl-terminus to assist in coupling to a protein carrier as described below. The compositions of all polypeptides were confirmed by amino acid analysis.

In preparing a synthetic polypeptide of this invention by the above solid phase method, the amino acid residues are linked to a resin (solid phase) through an ester linkage from the carboxy-terminal residue. When the polypeptide is to be linked to a carrier via a Cys residue or polymerized via terminal Cys residues, it is convenient to utilize that Cys residue as the carboxy-terminal residue that is ester-bonded to the resin.

The alpha-amino group of each added amino acid is typically protected by a tertiary-butoxycarbonyl (t-BOC) group prior to the amino acid being added into the growing polypeptide chain. The t-BOC group is then removed prior to addition of the next amino acid to the growing polypeptide chain.

Reactive amino acid side chains were also protected during synthesis of the polypeptides. Usual side-chain protecting groups were used for the remaining amino acid residues as follows:

O-(p-bromobenzyloxycarbonyl) for tyrosine; O-benzyl for threonine, serine, aspartic acid and glutamic acid; S-methoxybenzyl for cysteine, dinitrophenyl for histidine; 2-chlorobenzoxycarbonyl for lysine and tosyl for arginine.

Protected amino acids were recrystallized from appropriate solvents to give single spots by thin layer chromatography. Couplings were typically carried out using a ten-fold molar excess of both protected amino acid and dicyclohexyl carbodiimide over the number of milliequivalents of initial N-terminal amino acid. A two molar excess of both reagents may also be used. For asparagine, an equal molar amount of N-hydroxy-benzotriazole was added to the protected amino acid and dimethyl formamide was used as the solvent. All coupling reactions were more than 99% complete by the picric acid test of Gisin, *Anal. Chem. Acta.* 58:248–249 (1972).

After preparation of a desired polypeptide, a portion of the resulting, protected polypeptide (about 1 gram) was treated with two milliliters of anisole, and anhydrous hydrogen fluoride, about 20 milliliters, was condensed into the reaction vessel at dry ice temperature. The resulting mixture was stirred at about 4 degrees C. for about one hour to cleave the protecting groups and to remove the polypeptide from the resin. After evaporating the hydrogen flouride at a temperature of 4 degrees C. with a stream of $N_2$, the residue was extracted with anhydrous diethyl ether three times to remove the anisole, and the residue was dried in vacuo.

The vacuum dried material was extracted with 5% aqueous acetic acid (3 times 50 milliliters) to separate the free polypeptide from the resin. The extract-containing solution was lyophilized to provide a monomeric unoxidized polypeptide.

The produced synthetic polypeptide may be used as a reagent in an enzyme-linked immunosorbent assay (ELISA) to detect anti-EBNA antibodies. The synthetic polypeptide may also be used to produce an inoculum, usually by linking it to a carrier to form conjugate and then dispersing an effective amount of the conjugate in a physiologically tolerable diluent, as is discussed hereinafter.

It is also to be noted that a synthetic multimer of this invention can be prepared by the solid phase synthesis of a plurality of the polypeptides of this invention linked together end-to-end (head-to-tail) by an amide bond between the carboxyl-terminal residue of one polypeptide and the amino-terminal residue of a second polypeptide. Such synthetic multimers are preferably synthesized as a single long polypeptide multimer, but can also be prepared as individual polypeptides that are linked together subsequent to their individual syntheses, using a carbodiimide reagent such as 1-(3-dimethylaminopropyl)-3-ethyl-carbodiimide hydrochloride in water. The total number of amino acid residues contained in a multimer prepared as a single polypeptide chain is preferably less than about 50, so that up to about eight polypeptides of this invention can be incorporated into a single head-to-tail multimer chain that is synthesized as a single polypeptide. A synthetic head-to-tail multimer more preferably contains two to about four blocks of linked, synthetic, random copolymer polypeptides of this invention, and a total of less than about 40 amino acid residues.

B. Preparation of Polymers

The polypeptides of the present invention may be connected together to form an antigenic and/or immunogenic polymer (synthetic multimer) comprising a plurality of the polypeptide repeating units. Such a polymer typically has the advantage of increased immunogenicity and antigenicity. In addition, a carrier is typically not needed when a polymeric immunogen is utilized. Where different polypeptide monomers are used to make up the polymer, the ability to immunoreact with antibodies to several EBNA antigenic determinants is obtained. A still further advantage is the ability of such a polymer when used in an inoculum to induce antibodies that immunoreact with several antigenic determinants of EBNA.

A polymer of this invention may be prepared by synthesizing the polypeptides as discussed above and including cysteine residues at both the amino- and carboxy-termini to form a "diCys-terminated" polypeptide. For example, each of the polypeptides of Table 1 and polypeptides D1 and D2 of Table 2 may be synthesized to contain an additional Cys residue at each of the amino- and carboxy-termini to provide diCys-terminated polypeptides in their reduced forms. After synthesis, in a typical laboratory preparation, 10 milligrams of the diCys polypeptide (containing cysteine residues in un-oxidized form) are dissolved in 250 milliliters (ml) of 0.1 molar (M) ammonium bicarbonate buffer. The dissolved diCys-terminated polypeptide is then air oxidized by stirring the resulting solution gently for a period of about 18 hours in the air, or until there is no detectable free mercaptan by the Ellman test. [See Ellman, *Arch. Biochem. Biophys.*, 82:70–77 (1959).]

The polymer (synthetic multimet) so prepared contains a plurality of the synthetic, random copolymer polypeptide repeating units that are bonded together by oxidizing cysteine (cystine) residues. Such polymers typically contain their polypeptide repeating units bonded together in a head-to-tail manner as well as in head-to-head and tail-to-tail manners; i.e., the amino-termini of two polypeptide repeating units may be bonded together through a single cystine residue as may two carboxyl-termini since the linking groups at both polypeptide termini are identical.

C. Coupling To Carriers

The synthetic polypeptides were coupled to keyhole limpet hemocyanin (KLH) as carrier by the method described in Liu et al., *Biochem.*, 80:690 (1979). Briefly, 4 milligrams (mg) of the carrier were activated with 0.51 mg of m-maleimidobenzoyl-N-hydroxysuccinimide ester, and were subsequently reacted with 5 mg of the polypeptide through an amino- or carboxy-terminal cysteine to provide a conjugate containing about 10 to about 35 percent by weight polypeptide.

One or more additional amino acid residues may be added to the amino- or carboxy-termini of the synthetic polypeptide to assist in binding the polypeptide to a carrier. As discussed before, cysteine residues added at the amino- or carboxy-termini of the synthetic polypeptide have been found to be particularly useful for forming polymers via disulfide bonds. However, other methods well known in the art for preparing conjugates can also be used. Exemplary additional linking procedures include the use of Michael addition reaction products, dialdehydes such as glutaraldehyde, Klipstein et al., *J.Infect. Dis.*, 147:318–326 (1983) and the like, or the use of carbodiimide technology as in the use of a water-soluble carbodiimide to form amide links to the carrier, as discussed before for linking a plurality of polypeptides together to form a synthetic multimer.

Useful carriers are well known in the art, and are generally proteins themselves. Exemplary of such carriers are keyhole hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine:D-glutamic acid), and the like.

As is also well known in the art, it is often beneficial to bind a synthetic polypeptide to its carrier by means of an intermediate, linking group. As noted above, glutaraldehyde is one such linking group. However, when cysteine is used, the intermediate linking group is preferably an m-maleimidobenxoyl N-hydroxy succinimide (MBS), as was used herein.

Additionally, MBS may be first added to the carrier by an ester-amide interchange reaction as disclosed by Liu et al., supra. Thereafter, the addition can be followed by addition of a blocked mercapto group such as thiolacetic acid ($CH_3COSH$) across the maleimido-double bond. After cleavage of the acyl blocking group, a disulfide bond is formed between the deblocked linking group mercaptan and the mercaptan of the added cysteine residue of the synthetic polypeptide.

The choice of carrier is more dependent upon the ultimate use of the immunogen than upon the determinant portion of the immunogen, and is based upon criteria not particularly involved in the present invention. For example, if a inoculum is to be used in animals, a carrier that does not generate an untoward reaction in the particular animal should be selected.

D. ELISA

Anti-peptide antibody binding and inhibition studies were carried out by an enzyme-linked immunosorbent assay (ELISA) as described below.

Briefly, microtiter wells (Costar, #3590, Cambridge, Mass.) were typically coated with individual polypeptides as antigens by adding 100 microliters (ul) of BBS [10 millimoler (mM) sodium borate (pH 8.3), 150 mMNaCl] containing polypeptide at a concentration of 10 micrograms per milliliter (ug/ml). Contact between the wells and antigen-containing solution was maintained for a predetermined time, typically 15 minutes, and at 20 degrees C., to form an antigen-coated solid phase. The solid and liquid phases were separated and the wells were washed three times with BBS.

Non-specific binding sites were blocked by admixing 200 microliters of 1% bovine serum albumin (BSA) in each well to form another solid/liquid phase admixture, and maintaining that solid/liquid phase admixture for 30 minutes, at 20 degrees C. The phases were separated and excess, unbound BSA was removed by washing three times with BBS.

Rabbit and human sera (body sample aliquots) were assayed for anti-polypeptide activity by adding 100 microliters of a serum diluted 1:20 in BBS per well to form a solid/liquid phase composition. Contact between the diluted sera and the antigen-coated solid phase was maintained for a predetermined time such as i hour, and at 20 degress C., for an immunoreactant to form. The solid and liquid phases were separated, and the solid phase; i.e., antigen-coated, immunoreactant-containing wells, was then washed three times with BBS.

The antibodies in human sera that immunoreacted with an adsorbed polypeptide were detected using an indicating means comprising alkaline phosphatase-conjugated goat anti-human Ig antibody (Tago, Burlington, Calif.). The antibodies in rabbit sera that immunoreacted with an adsorbed polypeptide were detected using an indicating means comprising alkaline phosphatase-conjugated goat anti-rabbit Ig antibody (Kirkegard & Perry Laboratories, Inc., Gaithersburg, Md.). In either instance, 100 microliters of the indicating antibody diluted 1:300 in BBS were added per well to form a further solid/liquid phase composition. This solid- liquid phase composition was maintained for a predetermined time, one hour, for the formation of a reaction product between the human antibodies bound to the solid phase and the indicating means, and at 20 degrees C. The phases were separated, and the solid phase was washed 3 times with BBS.

Alkaline phosphatase-conjugated antibody bound to polypeptide specific antibody was detected by spectrophotometrically measuring the enzymatic hydrolysis of p-nitrophenyl phosphate to p-nitrophenol. Briefly, 100 microliters of p-nitrophenyl phosphate [1 milligram per milliliter in 2 mM $MgCl_2$, (pH 9.8), 50 mM sodium carbonate] were added to each well. The enzymatic reaction was allowed to proceed 1 hour and then the optical density at 405 nm was determined in a TITERTEK spectrophotometer available from Flow Laboratories, Inglewood, Calif.

Additional assays utilized in these studies wherein IgG to IgM ratios were determined to assess the state of EBV-induced disease were carried out as described in Smith et al., *J. Infect. Dis.*, 154:885–889 (1986) and Geltosky et al., *J. Clin. Lab Analysis*, 1:153–162 (1987). Briefly, microtiter wells as solid phase matrix were coated with 50 ul of 20 micrograms (ug) of polypeptide P62/ml in borate-buffered saline [BBS; 0.5 M sodium borate, 0.15 M MAC1, and 0.001 M $MgCl_2$, pH 8.3] for 12 hours at 4 degrees C. to form a solid support containing the peptide affixed to the solid phase matrix.

The solution was thereafter discarded and the plates were blocked with 300 ul of 10 percent normal goat serum in phosphate-buffered saline (PBS) at pH 7.3. After 90 minutes of maintenance (incubation) at 37 degrees C., the wells were emptied and dried for 60 minutes at 37 degrees C.

At this time, 200 ul of 10 percent goat serum in PBS were added to the wells. A volume of 10 ul of patient specimen serum was admixed to each goat serum-containing well to form a solid/liquid phase admixture. That admixture Was maintained for a time period of one hour at room temperature to permit binding of any antibodies present to the solid support and form a solid phase-bound immunoreactant containing those antibodies.

After washing five times with 350 ul of 0.05% Tween-20 [polyoxyethylene (20) sorbitan monolaurate] in PBS to effect separation of the solid and liquid phases, a solution of 200 ul of horseradish peroxidase-(HRPO-) conjugated mouse monoclonal antibody to human IgG or IgM (Ortho Diagnostic Systems, Raritan, N.J.) was admixed to each well to form a second solid/liquid phase admixture. This second solid/liquid admixture was maintained for another one hour time period to permit the enzyme-linked antibodies to bind to any solid phase-bound antibodies formed in the first solid/liquid phase admixture.

After separation of the solid and liquid phases, and washing of the solid phase five times using the Tween-20/PBS solution, above, color was developed by admixture of o-phenylenediamine (OPD; 2 mg of a citrate-buffered tablet dissolved in 3 ml of water; Pitman-Moore, Washington Crossing, N.J.) and hydrogen peroxide. The resulting solution was maintained for 30 minutes at room temperature. The reaction was stopped by admixture of 50 ul of 2N HCl, and the absorbance was determined at 490 nanometers (nm).

The results of the ELISA with polypeptide P62 as antigen were normalized by multiplying the absorbance values by a positive control ratio:

positive control ratio=reference absorbance value/mean absorbance of positive control.

The positive control was assigned a reference absorbance value (O.D.) of 1.0. The reference absorbance value was divided by the observed mean absorbance value of the positive control. The absorbance value for the controls and for each test specimen were multiplied by the positive control ratio to achieve a standardized ELISA value. Cutoff values (mean OD+SD) have been previously described [Geltosky et al. *J. Clin. Lab. Analysis*, 1:153–162 (1987)]. With these standardized conditions, the ratios of ELISA values of IgG to IgM greater than 0.7 were determined in a healthy, asymptomatic population. Absorbance values less than 0.7 were considered to represent an acute infection due to EBV [Smith et al., *J Infect Dis.*, 154:885–889 (1986)].

Still another, similar but much faster assay has also been developed and utilized herein. Here the solid phase matrix utilized was a so-called "spoon".

The particular spoons utilized were opaque, white polystyrene devices having a generally flattened upper portion (as normally used) that extends for about one-half the length of the spoon and is adapted for being held by a user's fingers. About two-thirds of the length of the lower portion (lower one-half) is narrower than the upper portion and is cylindrically shaped.

The lowest about one-third of the spoon contains a second flattened portion that is about the width of the upper portion and defines two dish-shaped depressions (wells) that are slightly smaller in diameter than the width of this flattened portion. The two dish-shaped depressions are separated by a dam that extends at approximately right angles to the flattened surface that defines the depressions. The top surface of the dam, looking downwardly toward the depressions, bears indicia such as "M" for IgM and "G" for IgG, and the vertical walls of the dam adjacent each depression are shaped into points that face one or the other depression. The points and their corresponding indicia on the top of the dam combine to indicate what is being assayed in each depression, IgM or IgG.

The before-mentioned flattened portions are of substantially the same width, and that width and the length of the spoon are proportioned to fit readily into and extend from a test tube such as a 13×100 or a 16×160 millimeter (mm) test tube, beaker or other liquid-containing device. Typically dimensions for such a spoon are a width of about 10–12 mm, a thickness of about 2–4 mm and an overall length of about 130–160 mm, with depressions that can hold about 200–250 ul of liquid.

A preferred spoon further includes a still wider portion at the upper-most about one-third of the upper, generally flattened portion whose width is greater than the diameter of a test tube to be used, e.g. wider than about 16 mm, so that the spoon can be suspended in the test tube without touching the bottom of the spoon to the bottom of the tube, and can be better adapted for holding. Still further, projecting legs, about the length of the thickness of the spoon are included on the side of the spoon opposite the depressions to provide a substantially stable, horizontal base on which a spoon can rest on a laboratory bench.

A series of the depressions of such spoons were coated with polypeptide P62, by admixing a solution containing 100 ug/ml of polypeptide in BBS at a pH value of 8.3–8.5. The solutions were maintained within the depressions for a time period of about 18–24 hours to affix the polypeptide to the matrix provided by the spoon depressions, and thereby form solid phase supports, and the solid and liquid phases were separated.

The non-specific binding sites on the solid phase supports so formed were blocked by admixture with a solution of 10 percent BSA or other non-human protein in PBS at a pH value of 7.4 for a time period of 90 minutes at 37 degrees C. When a spoon was not to be used immediately, 20 percent glycerol (v/v) was included in the blocking solution to aid with storage. The solid and liquid phases were thereafter separated and the spoons were dried at a temperature 37 degrees C. for one hour.

When used, 100 ul of the liquid body sample such as blood, plasma, serum or saliva were added to each depression of the spoon. Aliquots of the sample from one individual were used in each depression of a single spoon. The resulting solid/liquid admixtures were maintained for a time period of two minutes to form respective solid phase-bound immunoreactants.

The solid and liquid phases were separated and washed in two separate 13×100 mm test tubes, each containing 5 ml of PBS containing 0.05% Tween-20. A tap water rinse has also been used effectively for this step.

Thereafter, 100 ul of HRPO-conjugated anti-human IgG antibody were admixed with the solid support of the depression indicated by the before-mentioned "G", and 100 ul of HRPO-conjugated anti-human IgM antibody were admixed with the solid support of the depression indicated by the before-mentioned "M" to form two second solid/liquid phase admixtures. The resulting admixtures were maintained at room temperature for a two minute time period.

The solid and liquid phases were separated. The solid phase was thereafter washed twice with the PBS/Tween-20 solution described before.

After that washing step, 100 ul of a color developing solution such as that containing OPD, described before, or ABTS and 3 percent hydrogen peroxide (v/v) in the before-described buffer was admixed with the solid supports. The spoons were placed horizontally on their legs on a laboratory bench for this step. The color-forming solid/liquid admixture so formed was maintained for a further two minute time period at room temperature, and the color-forming reactions were stopped by admixture of 50 ul of a 1 percent solution of sodium dodecyl sulfate, or a 2 N HCl solution, as described before.

The above-described assay takes a little more than six minutes once the solid supports are prepared. The resulting assay is completed by a visual examination of the color intensity in each depression. Thus, where the color is more intense in the IgG assay, the patient is in convalescence; where the color is more intense in the IgM assay, the patient is in the acute phase of IM; and where the colors are of about the same intensity, acute phase IM is passing into convalescence.

Results using the above, approximately six minute assay were compared to results obtained in a microtiter plate calculated ratio assay as described previously that required about 2.5 hours to complete. Thirty serum samples each were compared from panels having (a) acute primary EBV-IM infections, (b) normal laboratory subjects that had experienced the virus and were serologically VCA$^+$, and (c) samples submitted to a clinical laboratory from patients with an IM-like illness.

Twenty-eight of the thirty sera from patients clinically identified as being in the acute stage were scored as acute in both assays. Two sera scored as having no result in the longer assay due to an IgM level below the minimum required were also scored as being acute phase sera in the shorter assay.

General agreement was noted with the other groups of sera with further examples of a result being scored for a serum in the shorter, visual assay where no result was recorded for the longer, quantititative assay. In addition, there were also a few instances where results were different.

In a subsequent clinical study, the approximately six minute assay was found to have a specificity and sensitivity for acute phase EBV-IM of about 94–95 percent.

E. Cell Cultures

The ability of the receptor molecules of this invention to immunoreact with EBNA produced in cells was studied as described hereinabove using the WI-L2, Raji, Daudi and BJAB cell lines. WI-L2 cells (ATCC CRL 8155 W1L2-NS, American Type Culture Collection, Bethesda, Md.) are an EBV genome-positive non-producer B-lymphoblast line, derived from a human patient with hereditary spherocytic anemia. Levy, et al., *Cancer* 22:517–524 (1968).

Raji cells (ATCC CCL 86, American Type Culture Collection, Bethesda, Md.) are an EBV genome-positive, EBNA producing lymphoblast-like cell line from a Burkitt lymphoma. Epstein, *J. Nat. Cancer Inst.* 34:231 (1965). Daudi cells (ATCC CCL 213, American Type Culture Collection, Bethesda, Md.) are also an EBNA producing cell line. BJAB cells are a non-EBNA producing lymphocyte cell line available at the Scripps Clinic and Research Foundation, La Jolla, Calif.

The above cell lines were cultured in RPMI 1640 medium [Moore, *J. Am. Med. Assoc.* 199:519–524 (1967); and Morton, In Vitro 6:89–100 (1970)] supplemented with 2 mM L-glutamine and 10% fetal calf serum.

The CMV strain AD-169 cells were a gift from Dr. D. Richman of the University of California, San Diego. The virus was propagated in human fibrolastics line GM-2504 obtained from the Human Genetic Mutant Cell Repository (Camden, N.J.). The cells were grown in DMEM medium containing 10 percent fetal calf serum and were infected just before confluency at a multiplicity of 3. Cells were harvested after nine days by washing twice with PBS, and extracts were prepared by adding 10 ml of DEM [2 percent SDS, 2 percent 2-mercaptoethanol, 0.0004 percent bromphenol blue, 40 millimolar (mM) Tris-HCl, pH 6.8 and 15 percent glycerol)] containing 10 ug/ml phenylmethysulfonyl fluoride directly to a 150 cm$^2$ tissue culture flask containing the adherent infected cells. The flask was scraped with a cell scraper and the solution was removed, boiled for two minutes and stored at –20° C.

F. Whole Cell Extracts

Extracts of EBNA producing and non-producing (control) cells were prepared to determine if receptor molecules of this invention were useful for diagnosing EBNA expression. Cells from cultures described hereinabove were washed in phosphate-buffered saline (PBS; 150 mMNaCl, 10 mM sodium phosphate, pH 7.4) containing 0.2 mM phenylmethylsulfonyl fluoride, swollen for 5 minutes in reticulocyte standard buffer (RSB; 10 mM MACl, 10 mM Tris-HCl, pH 7.4, 1.5 mM MgCl$_2$, 0.2 mM phenylmethylsulfonyl fluoride), and lysed by sonication in 3–5 volumes of RBS adjusted to 0.2–0.35 molar (M) NaCl. After 30 minutes on ice, the sonicate was centrifuged at 10,000×g for 15 minutes to remove cellular debris.

G. Immunoblotting Procedures

Cell extracts obtained above were assayed for EBNA using human sera known to contain anti-EBNA antibodies or exemplary receptor molecules of this invention. The extracts were either concentrated by precipitation with 2 volumes of ethanol at –20 degrees C. for about 18 hours, and were then dissolved in sample buffer [SB; 10% glycerol, 2% 2-mercaptoethanol, 1% sodium dodecyl sulfate (SDS), 0.002% bromphenol blue, 40 mM Tris-HCl (pH 7.4)] or diluted 1:6 in sample buffer for SDS-polyacrylamide gel electrophoresis (SDS-PAGE). 7.5% Polyacrylamide gels were cast and run according to the procedure of Laemmli, Nature, 277:680–685 (1970), applying 50 to 200 micrograms of total protein per lane.

After electrophoresis, the protein bands from the SDS polyacrylamide gels were transferred electrophoretically to a solid support in the form of nitrocellulose sheets (Schleicher and Schuell, Detroit, Mich.) by the procedure of Towbin et al., *Proc. Natl. Acad. Sci., U.S.A.*, 76:4350–5354 (1979). This was accomplished using a Bio-Rad Trans-Blot apparatus (Bio-Rad, Richmond, Calif.) at 70 volts for 2–3 hours in 12.5 mM Tris hydroxide, 96 mM glycine and 20% methanol.

Following transfer, the nitrocellulose filters or blots were saturated for one hour in either 2% BSA (w/v) in PBS or 2% powdered milk (w/v) in PBS to reduce non-specific binding. The blots were than immunoreacted with 0.1 ml of either EBNA positive human serum or rabbit anti-polypeptide antibodies in 2 ml of PBS or 2% milk for 1 hour at 37 degrees C.

Anti-peptide antibodies bound to EBNA protein were detected by reacting the blots with an indicating means. In this instance, 20 ml of $^{125}$I-labeled [200,000 counts per minute per milliliter (cpm/ml), 106 counts per minute per milligram (cpm/mg)] *S. aureus* protein A (Calbiochem, La Jolla, Calif.) were contacted with the immunoreaction product for 30 minutes at 37 degrees C. The blots were washed with PBS and exposed to Kodak XARx-ray film overnight at −70 degrees C.

In an alternative procedure, the cellular protein-containing extracts were loaded onto one 13-cm-wide slot of a 7.5 percent acrylamide gel and electrophoresed. The contents of the electrophoresed gel were transferred to nitrocellulose as previously described [Billings et al., *Proc. Natl. Acad. Sci. USA*, 80:7104–7108 (1983); Rumpold et al., *J. Immunol.*, 138:593–599 (1987); Rhodes et al., *J. Exp. Med.*, 165:1026–1040 (1987)]. Sera were diluted 1:20 or 1:50 in a powdered milk (PM) buffer (3 percent powered milk in 0.05 M borate, 0.15 M NaCl, pH 8.3), and contacted with the strip for 1 hour at room temperature to immunoreact antibodies in the sera with the proteins. The strips were then washed, and immunoreactivity was determined by incubation with a solution of 0.6 ug/ml (in PM) of affinity-purified rabbit anti-human IgM (Jackson Laboratories, Avondale, Pa.) or affinity-purified rabbit anti-human IgG antibodies from the same source.

After washing, the strips were reacted with a detecting solution of $^{125}$I-goat anti-rabbit IgG antibody as previously described [[Rumpold et al., *J. Immunol.* 128:593–599 (1987); Rhodes et al., in *Herpesvirus*, R. Rapp ed., Alan R. Liss, New York; p.,1487–496 (1984); Rhodes et al., *J. Immunology* 134:211–216 (1985); Smith et al., *J. Infect Dis.* 154:885–889 (1986); Geltosky et al., *J. Clin. Lab Analysis*, 1:153–162 (1987); and Rhodes et al., *J. Exp. Med.*, 165:1026–1040 (1987)] and bands were detected by autoradiography as described before.

Synthetic peptide inhibitions were performed by diluting the sera 1:50 in PM and adding free peptide to a final concentration of 400 ug/ml to inhibit IgM antibody and 20 to 50 ug/ml to inhibit IgG antibody. This solution was maintained (incubated) overnight at 4 degrees C. and then used to blot as described above.

H. Immunizations

The receptor molecules of this invention include whole antibodies raised in mammals by immunizing them with inocula including a polypeptide and/or multimer as described hereinabove. Both polypeptides and multimers may be used included in inocula alone or conjugated to a carrier protein such as keyhole limpet hemocyanin (KLH). However, polypeptides are preferably used as a conjugate and multimers are preferably used alone.

Rabbits were immunized with inocula containing 1.0 mg of conjugate in complete Freund's adjuvant (CFA), and boosted one month later with 1.0 mg of conjugate in incomplete Freund's adjuvant (IFA). Each immunization consisted of one subcutaneous injection, on the back hip. Rabbits were bled 1 and 2 months subsequent to the boost.

Sera containing immunologically active antibodies were then produced from the bleeds by methods well known in the art. These antibodies immunoreacted with one or more of the polypeptides of this invention, and an EBNA antigenic determinant. They may thus be used in a system to assay EBNA.

Individual inocula were prepared with CFA or IFA as follows: An amount of conjugate sufficient to provide the desired amount of polypeptide per inoculation (e.g., 1 mg) was dissolved in PBS (at about 0.5 ml) at pH 7.2. Equal volumes of CFA or IFA were then mixed with the conjugate solutions to provide an inoculum containing conjugate, water and adjuvant in which the water to oil ratio was 1:1. The mixture was thereafter homogenized to provide the inocula. The volume of an inoculum so prepared was typically greater than 1 ml, and some of the conjugate, PBS and adjuvant was lost during the emulsification. Substantially all of the emulsion that could be recovered was placed into a syringe, and then was introduced into the rabbits as discussed before. The amount of inoculum introduced into the rabbits is believed to have been about 90 percent of that present prior to the emulsification step.

The above inocula stock solutions are illustrative of the inocula of this invention. As demonstrated herein, they may be used to produce receptor molecules that immunoreact with EBNA.

I. Immunofluorescense Procedures

Another illustrative method for assaying EBNA in a body sample uses receptor molecules of this invention and a fluorochromatic indicating means to detect the product of a receptor-EBNA immunoreaction.

In the present study, $2 \times 10^4$ WI-L2 cells, grown as described above, were spread on a plain microscope slide using a cytocentrifuge (CYTOSPIN, Shandon Southern, Astmoor, Runcorn, Chesire, England). After air drying for 5 minutes at 20° C., the cells were fixed in acetone for 2 minutes, then air dried for 2 minutes at 20° C. The slides were stored at −20° C. until used.

The fixed WI-L2 cells were assayed for EBNA using rabbit anti-polypeptide antibodies (receptors of this invention) raised to polypeptides P27, P60, P62 and P89. Fifty ul of each rabbit antiserum, diluted 1:10 in VBS buffer (120 mMbarbitol pH 7.3, 144 mMNaCl, 2.5 mM $MgCl_2$ and 0.75 mM $CaCl_2$) were incubated (contacted and maintained in contact with the fixed cells) at 20° C. on a slide for a predetermined period of time (e.g. 30 minutes) sufficient for the antibodies and EBNA to immunoreact. A negative control slide was treated in identical manner with normal rabbit serum.

During the above incubation, a portion of the anti-polypeptide antibodies immunoreacted with EBNA present in the fixed WI-L2 cells. Unbound antibodies were removed by washing with VBS, leaving only the EBNA-receptor immunoreaction product on the slide.

Anti-polypeptide antibodies bound to EBNA were detected by first incubating 50 ul of guinea pig complement (Tago, Burlingame, Calif.) diluted 1:10 in VBS on each slide for a period of time (30 minutes) sufficient for the complement to bind to the receptors. The slides were then washed with VBS to remove any complement not bound to the rabbit anti-polypeptide IgG.

Fluorescein labeled goat anti-guinea pig $C_3$ (labeled anti-complement antibodies, Cappel Laboratories, Cochranville, Pa.) was used to detect the antigen-antibody-complement complexes. Fifty ul of the indicating antiserum, diluted 1:20 in VBS, were incubated as above on each slide for 30 minutes at 20° C. Unbound goat anti-guinea pig $C_3$ was washed off the slide with VBS. Immunoreaction products were then visualized by fluorescent microscopy.

J. Circular Dichroism Spectroscopy

Figure 1:
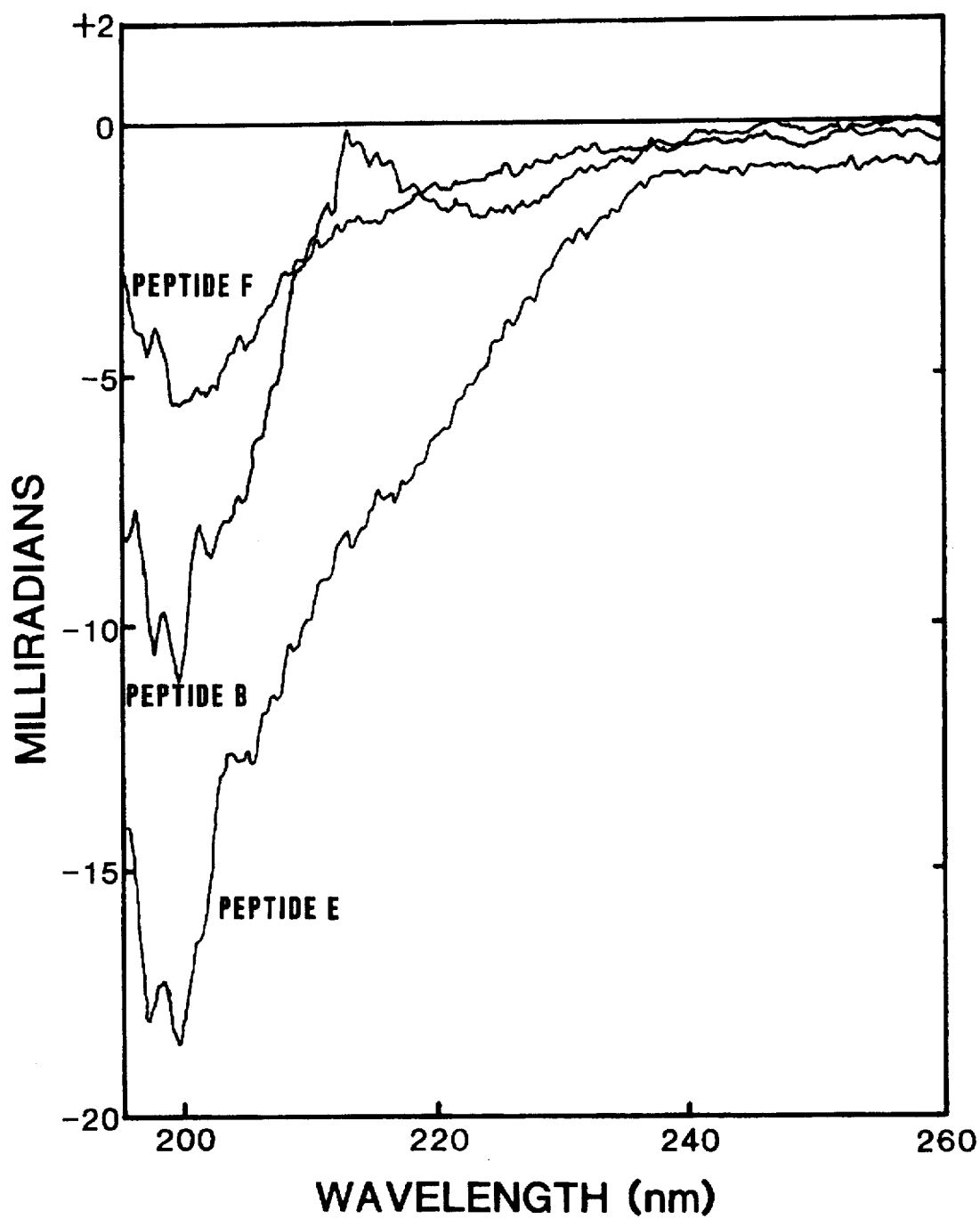
FIG. 1 is a plot of the circular dichroism spectra of polypeptides (F), (B) and (E). These polypeptides are also referred to herein as polypeptides F13, F62 and F12, respectively. Each spectrum is the average of 10 successive scans of a polypeptide in physiological solution (phosphate buffered saline) at a concentration of 1 milligram/milliliter (mg/ml). The optical rotation is expressed as milliradians and is plotted against the polarized light wavelength, expressed in nanometers (nm). The relatively featureless plot for polypeptide F (F13) is indicative of a random conformation that is the usual result obtained with peptides of this size. The trough and peaks spectrum demonstrated by polypeptide B (P62) is characteristic of a relatively stable secondary structure or conformation, probably beta-pleat. Although the data are not shown, the polypeptides P27, P60, F14 and F15 have very similar spectra indicating that the more preferred polypeptides of this invention exist as similar stable conformations in physiological solution. The spectrum of polypeptide E (F12) indicates partial assumption of such conformation.

The conformational properties of the polypeptides were investigated to elucidate any secondary structure that might be necessary for polypeptide immunoreaction with human anti-EBNA antibodies. The polypeptides were dissolved at a concentration of 1 mg/ml in phosphate-buffered saline (PBS). Spectra were taken using 1 ml samples in a Cary 61 spectropolarimeter (Cary Instruments, Applied Physics Corp., Monrovia, Calif.) interfaced and automated with a Digital Equipment Corporation 11/02 computer (Digital Equipment Corporation, Maynard, Mass.). The average of 10 successive scans for each polypeptide was plotted as shown in FIG. 1.

K. Specimen Sources and Serology

Serum samples used herein were obtained from a variety of sources. One set of sera for these studies were obtained from 13 patients with EBV-induced IM. Heterophil antibodies specific for IM had previously been identified in 10 of 13 patients by using a horse-cell differential-adsorption tube test. Heterophil antibodies were not detected in two patients despite testing by a variety of methods. One individual had nondiagnostic low levels of horse-cell agglutinins that were detected in only a single specimen drawn during the acute phase of her illness. This patient was considered to be heterophil-negative for the purposes of this study. Serological data showed evidence of ongoing primary EBV infections from the three heterophil-negative patients.

The data from two of the 10 heterophil-positive and two of the three heterophil-negative patients have been published previously [Horwitz et al., *Am. J. Med.* 63:947–957 (1977)]. For the present study, the EBV serological tests were performed on previously frozen serum samples by indirect immunofluorescence with commercially available tests for IgG and IgM antibodies to VCA (Litton Bionetics, Inc., Charleston, S.C.).

Another group of sera was used for the EBV-IM and CMV-IM studies. In that group of samples, one patient (D.B.) had a typical episode of heterophil-positive EBV-IM followed by an uneventful clinical recovery. During the acute phase of illness, he developed high titers of antibodies to VCA (IgM=1:80 and VCA-IgG 1:1280) without accompanying antibodies to anti-EBNA (1:2). By 174 days after onset, IgM anti-VCA antibodies were no longer detectable, whereas anti-EBNA had evolved between 76 and 111 days. Antibodies to CMV were not detected in serial sera by complement fixation (1:8). A second patient (D.S.) had an initial active, probable primary cytomegalovirus (CMV) infection (CMV-IM) that was followed four months later by a primary EBV infection. This patient demonstrated CMV macroglobulins (1:256), a four-fold rise in antibodies to anti-CMV by complement fixation (CMV-CF), and no antibody responses to any EBV-related antigens. During his second illness, beginning 124 days after the onset of the first, a primary EBV infection occurred characterized by IgM anti-VCA (1:320) and an initial absence (1:2), but later evolution of antibodies to EBNA. The IgM antibodies to VCA disappeared with serial testing. During his second illness (EBV-IM), CMV macroglobulins (CMV-IgM) were no longer detectable, whereas complement-fixing antibodies to CMV were still present at stable levels of 1:128.

Sera were also available from ten other patients drawn during the various phases of CMV-induced mononucleosis. Their acute phase sera demonstrated significant titers (=1:32) of CMV macroglobulins and anti-CMV (CF) in all cases. Four-fold titer rises or falls were noted by complement fixation in six of the ten (6/10) serially sampled patients. All ten patients demonstrated serological evidence of old EBV infections with moderate constant levels of anti-VCA (IgG) anti-EBNA (1:10) and no antibodies to anti-VCA-(IgM). Some data from the latter eleven patients were included in an earlier report [Horwitz et al., *Medicine*, 65:124–133 (1986)].

Assays for EBV-related antibodies to VCA (IgM and IgG), early antigens (EA), and EBNA, as well as CMV macroglobulins (CMV-IgM), were performed by standard indirect immunofluorescent (IFA) procedures [Horwitz et al., *Medicine*, 65:124–133 (1986] and Henle et al., *Human Pathology*, 5:551–565 (1974)]. Anti-CMV was also detected by complement fixation using the AD-169 strain of virus (Microbiological Associates, Bethesda, Md.).

The foregoing is intended as illustrative of the present invention but not limiting. Numerous variations and modifications may be effected without departing from the true spirit and scope of the novel concepts of the invention. It is to be understood that no limitation with respect to the specific polypeptides, antibodies, their compositions and uses illustrated herein is intended or should be inferred.

What is claimed is:

1. A CMV-related polypeptide that consists of an amino acid residue sequence selected from the group consisting of:

a) Ala—Gly—Gly—Gly—Gly—Gly—Gly—Gly—Ala—
      Gly—Gly—Gly—Gly—Gly—Gly—Gly—Gly—Ser—
      Gly—Gly, b) Ser—Ser—Ser—Ser—Ala—Gly—Gly—Gly—Gly—
      Gly—Gly—Gly—Ala—Gly—Gly—Gly—Gly—Gly—
      Gly—Gly—Gly—Ser—Gly—Gly and c) Ser—Ser—Ser—Ser—Ala—Gly—Gly—Gly—Gly—
      Gly—Gly—Gly—Ala—Gly—Gly—Gly—Gly—Gly—
      Gly—Gly—Gly—Ser—Gly—Gly—Cys, and pharmaceutically acceptable salts thereof, wherein said polypeptide immunoreacts with anti-EBNA antibodies.

2. A polypeptide having from 20 to 40 amino acid residues wherein said polypeptide has an amino acid residue sequence corresponding to the amino acid residue sequence of CMV-encoded polypeptide antigen as follows:

---

MET ASP LEU PRO THR THR VAL VAL ARG LYS TYR TRP THR PHE ALA ASN
PRO ASN ARG ILE LEU HIS GLN SER VAL ASN GLN THR PHE ASP VAL ARG
GLN PHE VAL PHE ASP THR ALA ARG LEU VAL ASN CYS VAL ASP GLY ASP
GLY LYS VAL LEU HIS LEU ASN LYS GLY TRP LEU CYS ALA THR ILE MET
GLN HIS GLY GLU ALA SER ALA GLY ALA LYS THR GLN GLN GLY PHE MET
SER ILE ASP ILE THR GLY ASP GLY GLU LEU GLN GLU HIS LEU PHE VAL
ARG GLY GLY ILE VAL PHE ASN LYS SER VAL SER SER VAL VAL GLY SER
SER GLY PRO ASN GLU SER ALA LEU LEU THR MET ILE SER GLU ASN GLY
ASN LEU GLN VAL THR TYR VAL ARG HIS TYR LEU LYS ASN HIS GLY GLU
SER SER SER GLY GLY GLY GLY CYS GLY ALA ALA SER THR ALA SER ALA
VAL CYS VAL SER SER LEU GLY GLY SER GLY GLY THR ARG ASP GLY PRO
SER ALA GLU GLU GLN GLN ARG ARG ARG GLN GLU GLN ARG HIS GLU GLU
ARG ARG LYS LYS SER SER SER SER ALA GLY GLY GLY GLY GLY GLY GLY
ALA GLY GLY GLY GLY GLY GLY GLY GLY SER GLY GLY GLN HIS SER SER
ASP SER ALA ASN GLY LEU LEU ARG ASP PRO ARG LEU MET ASN ARG GLN
LYS GLU ARG ARG PRO PRO PRC SER SER GLU ASN ASP,

--- wherein said polypeptide includes a sequence selected from the group consisting of:

a)  —Ala—Gly—Gly—Gly—Gly—Gly—Gly—Gly—Ala—
       Gly—Gly—Gly—Gly—Gly—Gly—Gly—Gly—Ser—
       Gly—Gly— and b)  —Ser—Ser—Ser—Ser—Ala—Gly—Gly—Gly—Gly—
       Gly—Gly—Gly—Ala—Gly—Gly—Gly—Gly—Gly—
       Gly—Gly—Gly—Ser—Gly—Gly—, and pharmaceutically acceptable salts thereof, wherein said polypeptide immunoreacts with anti-EBNA antibodies.

* * * * *